(12) United States Patent
Komander et al.

(10) Patent No.: US 8,765,406 B2
(45) Date of Patent: Jul. 1, 2014

(54) ENGINEERED E2 FOR INCREASING THE CONTENT OF FREE LYS11-LINKED UBIQUITIN

(71) Applicants: David Komander, Cambridge (GB); Anja Bremm, Cambridge (GB)

(72) Inventors: David Komander, Cambridge (GB); Anja Bremm, Cambridge (GB)

(73) Assignee: Medical Research Council, Swindon (GB)

( * ) Notice: Subject to any disclaimer, the term of this patent is extended or adjusted under 35 U.S.C. 154(b) by 0 days.

(21) Appl. No.: 13/670,594

(22) Filed: Nov. 7, 2012

(65) Prior Publication Data

US 2013/0065273 A1 Mar. 14, 2013

Related U.S. Application Data

(63) Continuation-in-part of application No. PCT/GB2011/000704, filed on May 6, 2011.

(60) Provisional application No. 61/333,145, filed on May 10, 2010.

(30) Foreign Application Priority Data

May 7, 2010 (GB) .................... 1007704.8

(51) Int. Cl.
*C12N 9/48* (2006.01)

(52) U.S. Cl.
USPC ........................................ 435/68.1

(58) Field of Classification Search
USPC .......................... 435/7.2, 61.2, 188
See application file for complete search history.

(56) References Cited

FOREIGN PATENT DOCUMENTS

GB PCT/GB2011/000704 * 5/2010 ................. 435/68.1

OTHER PUBLICATIONS

Schwartz et al., The ubiquitin-proteasome pathway and pathogenesis of human diseases. Annual Rev. Med. 50: 57-74, 1999.*
Reyes-Turcu et al., The Ubiquitin Binding Domain ZnF UBP Recognizes the C-Terminal Diglycine Motif of Unanchored Ubiquitin. Cell. 124: 1197-1208, 2006.*
Olga V. Baboshina, et al., Novel Multiubiquitin Chain Linkages Catalyzed by the Conjugating Enzymes $E2_{EPF}$ and RAD6 Are Recognized by 26 S Proteasome Subunit 5, The Journal of Biological Chemistry (1996) vol. 271, No. 5, p. 2823-2831.
Anja Bremm, et al., Lys11-Linked Ubiquitin Chains Adopt Compact Conformations and Are Preferentially Hydrolyzed by the Deubiquitinase Cezanne, Nature Structural & Molecular Biology (2010) vol. 17, No. 8, p. 939-947.
David Komander, The Emerging Complexity of Protein Ubiquitination, Biochemical Society Transactions (2009) vol. 37, p. 937-953.
Yihong Ye, et al., Building Ubiquitin Chains: E2 Enzymes At Work, Nature Reviews Molecular Cell Biology (2009) vol. 10, p. 753-763.

* cited by examiner

*Primary Examiner* — Tekchand Saidha
*Assistant Examiner* — Rama P Ramanujam
(74) *Attorney, Agent, or Firm* — Vedder Price P.C.; Thomas J. Kowalski; Deborah L. Lu

(57) ABSTRACT

The invention provides a chimeric E2 enzyme comprising a Ubc domain fused to a heterologous ubiquitin binding domain (UBD). The chimeric enzymes of the invention may be useful in producing elevated levels of free polyubiquitin.

18 Claims, 18 Drawing Sheets a
K11-linked diUb b
Position of the Ile44 surface patch c
K11 interface d
Extended hydrophobic patch

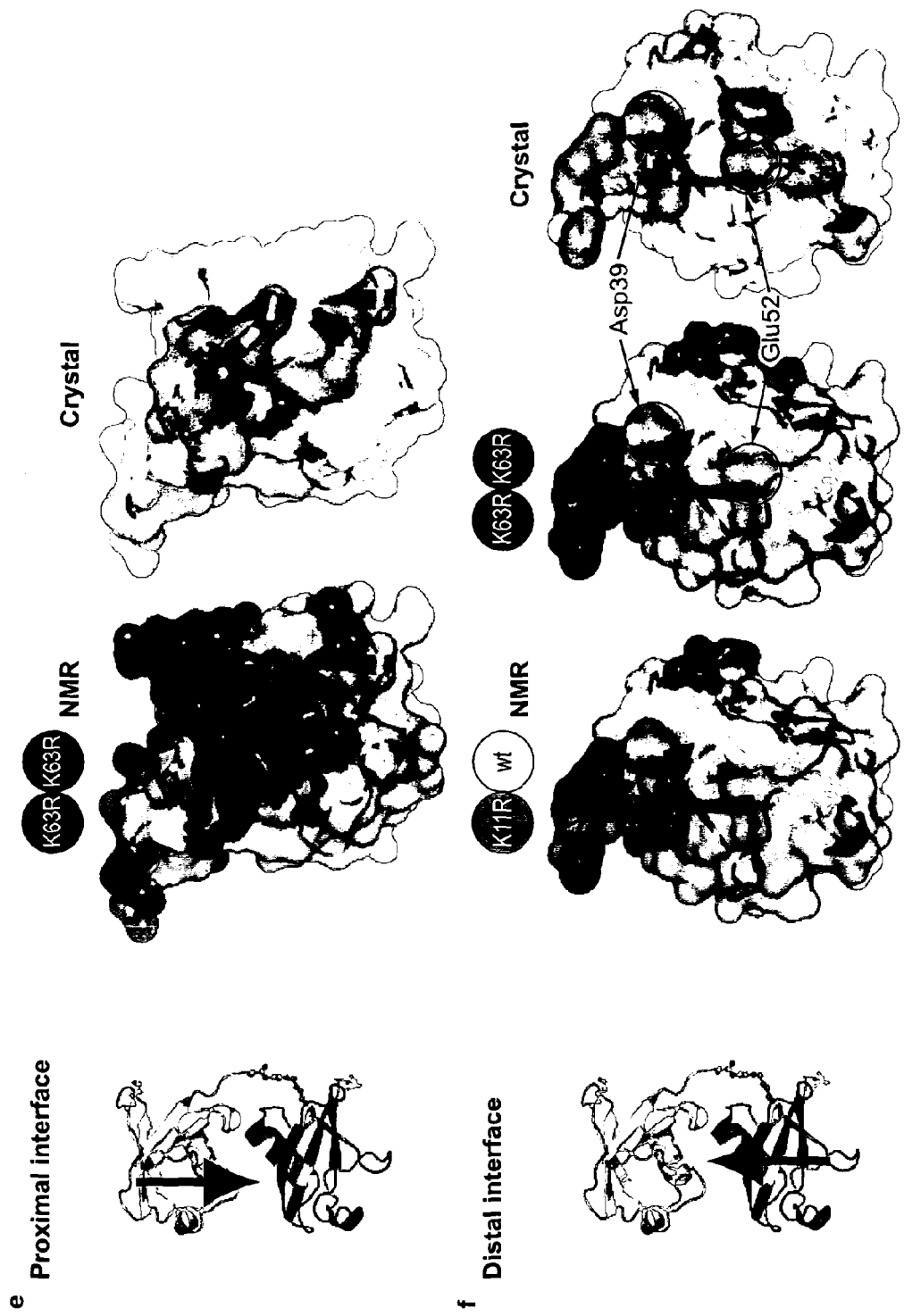

ated (DUBs) (reviewed in Komander, 2009). This information is currently lacking for atypical ubiquitin chains.

ENGINEERED E2 FOR INCREASING THE CONTENT OF FREE LYS11-LINKED UBIQUITIN

RELATED APPLICATIONS AND INCORPORATION BY REFERENCE

This application is a continuation-in-part application of international patent application Serial No. PCT/GB2011/000704 filed 6 May 2011, which published as PCT Publication No. WO 2011/138593 on 10 Nov. 2011, which claims benefit of GB patent application Serial No. 1007704.8 filed 7 May 2010 and U.S. provisional patent application Ser. No. 61/333,145 filed 10 May 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to engineered E2 ubiquitin conjugating enzymes. In particular, the invention relates to chimeric E2 enzymes which are fused to a ubiquitin binding domain (UBD). The fusion is engineered by replacing the c-terminal tail of a class II E2 enzyme with a UBD, such that the Ubiquitin conjugating (Ubc) catalytic domain is fused to the UBD. This modification increases the efficiency of ubiquitin polymerisation by E2 enzymes, and facilitates isolation of specific forms of polyubiquitin.

BACKGROUND OF THE INVENTION

Protein ubiquitination is a versatile posttranslational modification with roles in protein degradation, cell signaling, intracellular trafficking and the DNA damage response (Chen and Sun, 2009; Komander, 2009). Ubiquitin polymers are linked through one of seven internal lysine (K) residues or through the N-terminal amino group. Importantly, the type of ubiquitin linkage determines the functional outcome of the modification (Komander, 2009). The best-studied ubiquitin polymers, K48- and K63-linked chains, have degradative and non-degradative roles, respectively (Chen and Sun, 2009; Hershko and Ciechanover, 1998). However, recent data has revealed an unexpected high abundance of so-called atypical ubiquitin chains; for example, K11 linkages have been found to be as abundant as K48-linkages in *S. cerevisiae* (Peng et al., 2003; Xu et al., 2009).

Polyubiquitin chains are assembled on substrates through the concerted action of a three-step enzymatic cascade, involving an E1 ubiquitin activating enzyme, an E2 ubiquitin conjugating enzyme, and E3 ubiquitin ligases (Dye and Schulman, 2007). While E3 ligases attach polyubiquitin chains to a target and thus confer substrate specificity, E2 enzymes are thought to determine the type of chain linkage in polyubiquitin chains. K48- and K63-specific E2 enzymes have been identified (Chen and Pickart, 1990; Hofmann and Pickart, 1999), which allowed structural analysis of these chain types as well as a detailed understanding of specificity of ubiquitin binding domains (UBDs) and deubiquitinases (DUBs) (reviewed in Komander, 2009). This information is currently lacking for atypical ubiquitin chains.

Several recent reports have implicated K11-linked ubiquitin chains in distinct biological processes. Early data indicated that K11-linked chains are proteasomal degradation signals (Baboshina and Haas, 1996). An E2 enzyme, UBE2S/E2-EPF, was identified that assembled K11 linkages in vitro (Baboshina and Haas, 1996). The human anaphase promoting complex (APC/C) was found to assemble K11 linkages using the E2 enzyme UBE2C/UbcH10, on proteins that need to be degraded for cell cycle progression (Jin et al., 2008). A yeast proteomics study, apart from having revealed the high abundance of K11 linkages, also implicated this chain type with endoplasmic reticulum-associated degradation (ERAD), and identified yeast Ubc6 as an E2 enzyme involved in synthesis of K11-linked chains (Xu et al., 2009). In mammalian cells, K11 linkages were found to be enriched in UBA/UBX protein complexes, which interact with the key ERAD regulator p97/cdc48 (Alexandru et al., 2008). Hence, K11-linked chains seem to regulate numerous important cellular processes, and may act as a distinct proteasomal degradation signal. However, cellular mechanisms of assembly and disassembly of K11 linkages, as well as structural determinants for K11 linkage recognition, are unknown.

The structure of E2 enzymes is well characterised. All E2 enzymes comprise a conserved domain of about 16 kD (the Ubc domain) which contains the Ubc motif, [FYWLS]-H-[PC]-[NH]-[LIV]-x(3,4)-G-x-[LIV]-C-[LIV]-x-[LIV]. The Ubc domain contains a conserved cysteine residue, which accepts ubiquitin from the ubiquitin-activating enzyme E1 to form a thiol ester. Substitution of the conserved cysteine abolishes E2 activity. A suggested motif rich in basic residues is found at the N-terminus of the UBC domain which may be involved in E1 binding.

E2 enzymes can be classified on the basis of their structure into three classes.

Class I: these proteins comprise simply the "Ubc" catalytic domain. In vitro these enzymes are very poor at transferring ubiquitin to proteins on their own, and probably require an E3 to aid this in vivo. UBC 4 and 5 of *S. cerevisiae*, UBC1 of *Arabidopsis thaliana*, and human UBE2D1, UBE2D2, UBE2D3 or UBE2D4 are examples of this class of E2, and are known to be important in the ubiquitination of many short-lived and abnormal proteins prior to degradation.

Class II: these enzymes contain a C-terminal tail attached to the Ubc domain. The tails are different in type but very acidic tails, as found in Ubc2 (also known as Rad6) of *S. cerevisiae*, appear to mediate inteaction with protein substrates, in this case with the basic histones. Ubc2/Rad6 will ubiquitinate histones in vitro, which requires the C-terminal tail and is known to be involved in DNA repair. This may be a form of ubiquitination that results in protein modification but not degradation. Other C-terminal tails appear to be involved in E2 localisation. Ubc6 of *S. cerevisiae* is found anchored to the ER membrane with the active site facing the cytosol. The 95 residue C-terminal tail of Ubc6 includes a hydrophobic signal-anchor sequence.

Class III: N-terminal extensions are present in this class of E2s. Several enzymes of this class have been identified but the function of the extensions is unknown.

Ubiquitin binding domains are modular protein elements that bind non-covalently to ubiquitin. They are typically small, being 20 to 150 amino acids in length, and independently-folded, making their isolation straight forward. They are based on a number of different ubiquitin binding motifs. The Ubc of E2 enzymes is one class of ubiquitin binding domain (UBD). Other classes include α-helical domains, zinc finger domains (ZnFs) and plekstrin homology (PH) domains. See, for example, Dikic et al., 2009. Many UBDs are known in the art; for example, see Table 1 in Dikic et al., page 663.

Isopeptidase T (IsoT, or USP5) contains a ZnF-type UBD (known as ZnF UBP or PAZ domain) between amino acid positions 163 and 291 (see Reyes-Turcu et al., 2006). HDAC6 (Boyault et al., 2006) also contains a ZnF UBP domain. Other zinc finger ubiquitin binding domains include UBZ domains, as contained in polymerase-h and polymerase-k; NZF and A20-like ZnF domains.

Alpha-helical types of domains include, for example, UBA domains, found in Rad23 and R23A proteins, or ubiquitin interacting motifs (UIM, MIU or dUIM); see Dikic et al., 2009.

The study of the ubiquitin system requires the ability to produce unattached polymeric ubiquitin in solution, for structural and functional analysis. As noted above, ubiquitin chains vary according to which of the 7 internal Lys residues is used for concatenation of the ubiquitin molecules. In absence of a E3 ubiquitin ligase, most E2 enzymes fail to assemble polyubiquitin. Class II E2 enzymes can assemble polyubiquitin chains on their own C-terminal tails. Very few E2 enzymes, including UBE2R2/cdc34, UBE2K and UBE2S produce free, i.e. unattached, polyubiquitin in solution. For instance, UBE2S, which assembles K-11 linked polyubiquitin, is inefficient at producing free ubiquitin multimers in solution, producing only small amounts of free ubiquitin dimers. There is a need, therefore, for improved E2 enzymes that can be used to produce free polyubiquitin in solution.

Citation or identification of any document in this application is not an admission that such document is available as prior art to the present invention.

SUMMARY OF THE INVENTION

Applicants have analyzed the K11-specific E2 enzyme UBE2S that assembles K11-linked chains on its own C-terminal tail in vitro, and also generates limited amounts of free, i.e. unattached, K11-linked diubiquitin. By removing the C-terminal tail, Applicants have engineered an E2 enzyme that produces free K-11 linked diubiquitin. Furthermore, by replacing the C-terminal tail of the E2 with a UBD, Applicants have engineered a UBE2S fusion protein that synthesizes free K11-linked polymers, including trimers and tetramers, with markedly increased efficiency, allowing high-level purification of K11-linked ubiquitin dimers, trimers and tetramers, and facilitating structural studies.

In a first aspect, therefore, there is provided an E2 enzyme comprising a Ubc domain, from which an N-terminal or a C-terminal tail has been removed.

In a preferred embodiment, the Ubc domain is fused to a heterologous ubiquitin binding domain (UBD).

Preferably, the UBD is C-terminal to the Ubc domain. In class II E2 enzymes, a C-terminal amino acid extension is present, which is partly replaced by the UBD. Some E2 enzymes, such as class III enzymes, have an N-terminal tail which may be removed and optionally at least partly replaced with a UBD.

UBDs are known in the art, and exemplary UBDs may be of the α-helical, zinc finger or plekstrin homology domain classes.

For example, the UBD is a domain selected from the group consisting of UIM, IUIM (MIU), DUIM, UBM, UBA. GAT, CUE, VHS, UBZ, NZF, ZnF A20, ZnF UBP (PAZ), PRU, GLUE, UEV, UBC, SH3, PFU and Jab1/MNP domains.

Preferably, the UBD is a ZnF UBP domain, such as the UBD derived from Isopeptidase T. It advantageously may comprise the sequence from about position 163 to about position 291 of Isopeptidase T, which may comprise the UBD. For example, it may comprise residues 173-289 of Isopeptidase T.

Alternative UBDs include UBA, UIM and NZF domains. ZnF and NZF domains are particularly preferred.

The Ubc will determine the specificity of linkages used in the polyubiquitin chains. Ubc domains may be derived from E2 enzymes. Referring to human E2 enzymes, the Ubc domain may be derived from an E2 enzyme selected from the group consisting of UBE2A, UBE2B, UBE2C, UBE2D1, UBE2D2, UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2NL, UBE2O, UBE2Q1, UBE2Q2, UBE2R1, UBE2R2, UBE2S, UBE2T, UBE2U, UBE2W, UBE2Z, and BIRC6. The foregoing are human E2 enzymes. Of course, mammalian, yeast or other E2 enzymes may be used, preferably those enzymes which are equivalent to the foregoing human enzymes.

Preferably, the Ubc domain is derived from UBE2S. The Ubc domain is comprised in residues 1 to 156 of UBE2S, and advantageously these residues are incorporated into the chimeric E2 enzyme. Residues 196-222 of UBE2S comprise the C-terminal extension; these residues are removed and/or replaced with a UBD.

The invention provides a method for increasing the capacity of an E2 enzyme to produce free polyubiquitin dimers, comprising removing a C-terminal tail from said E2 enzyme. In a further aspect, the invention provides a method for increasing the capacity of an E2 enzyme to produce free polyubiquitin chains containing more than two ubiquitin monomers in solution, comprising conjugating the Ubc domain of said E2 enzyme to a UBD.

Preferably, the polyubiquitin chains comprise trimers or tetramers of ubiquitin monomers.

In a further aspect, the invention provides a method for producing free polyubiquitin chains linked through a desired lysine residue, comprising the steps of: (a) selecting an E2 enzyme which possesses the desired specificity for ubiquitin lysine residues; (b) fusing the Ubc catalytic domain of said E2 enzyme to a UBD ubiquitin binding domain; and incubating the resulting chimeric protein with an E1 ubiquitin activating enzyme and monomeric ubiquitin.

In a preferred embodiment, the incidence of undesired lysine linkages is reduced by including a linkage-specific deubiquitinase in the incubation mixture. Such enzymes preferentially degrade polymers having a specific lysine linkage; thus, if the product of the chimeric E2 is contaminated with undesired linkage polymers, the contaminants may be specifically removed.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
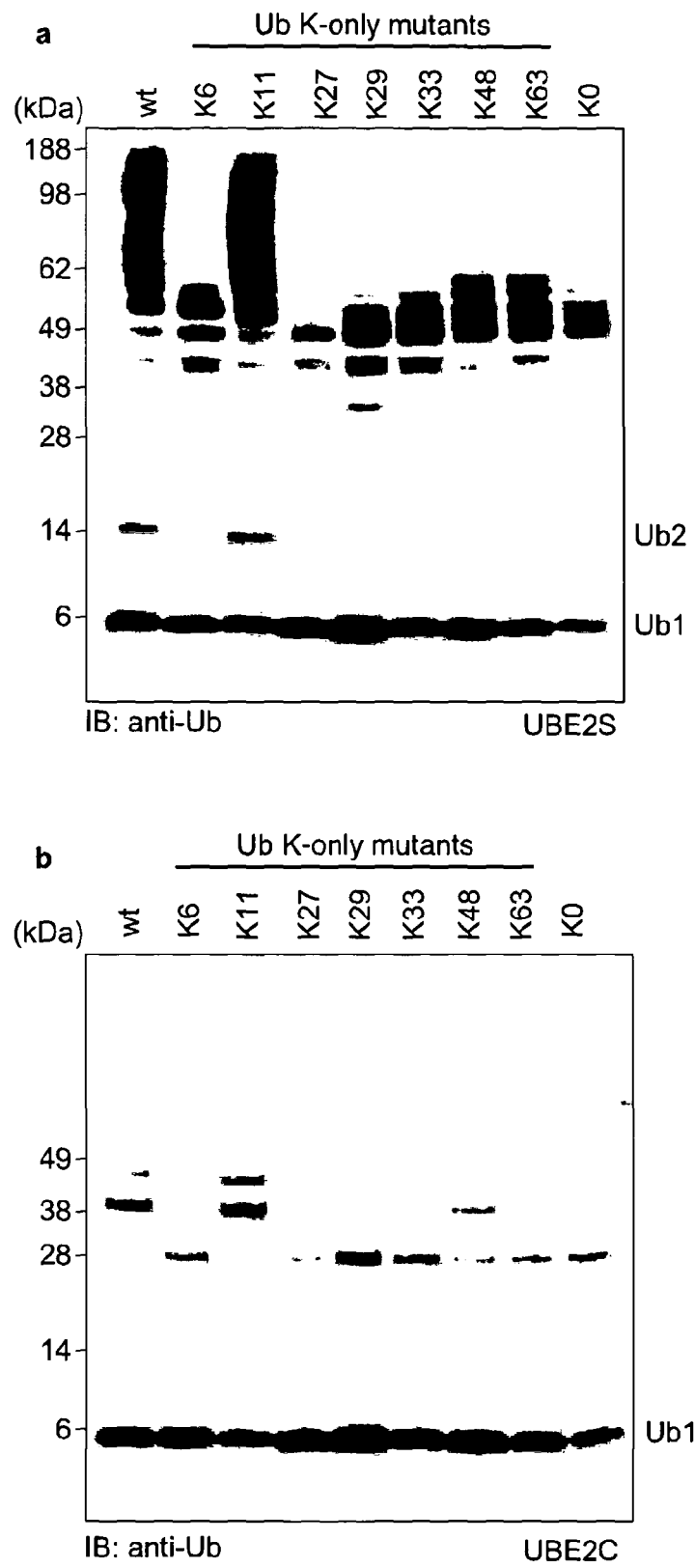
FIG. 1: UBE2S is a KU-specific E2 enzyme. (a) UBE2S and (b) UBE2C were analyzed in autoubiquitination assays in the presence of E1, ubiquitin and Mg•ATP. The panel of single-Lys ubiquitin mutants reveals the intrinsic linkage specificity. Autoubiquitination is visualized with a polyclonal anti-ubiquitin antibody. UBE2S, but not UBE2C, autoubiquitinates and also assembles unattached KU-linked ubiquitin chains. (c) Time course assay for autoubiquitination by UBE2S. The reaction for wild-type (wt) and K11-only ubiquitin leads to similar high-molecular weight conjugates, while for the Lysless (K0) and K63-only ubiquitin an equivalent pattern of multimonoubiquitination is observed.
Figure 1:
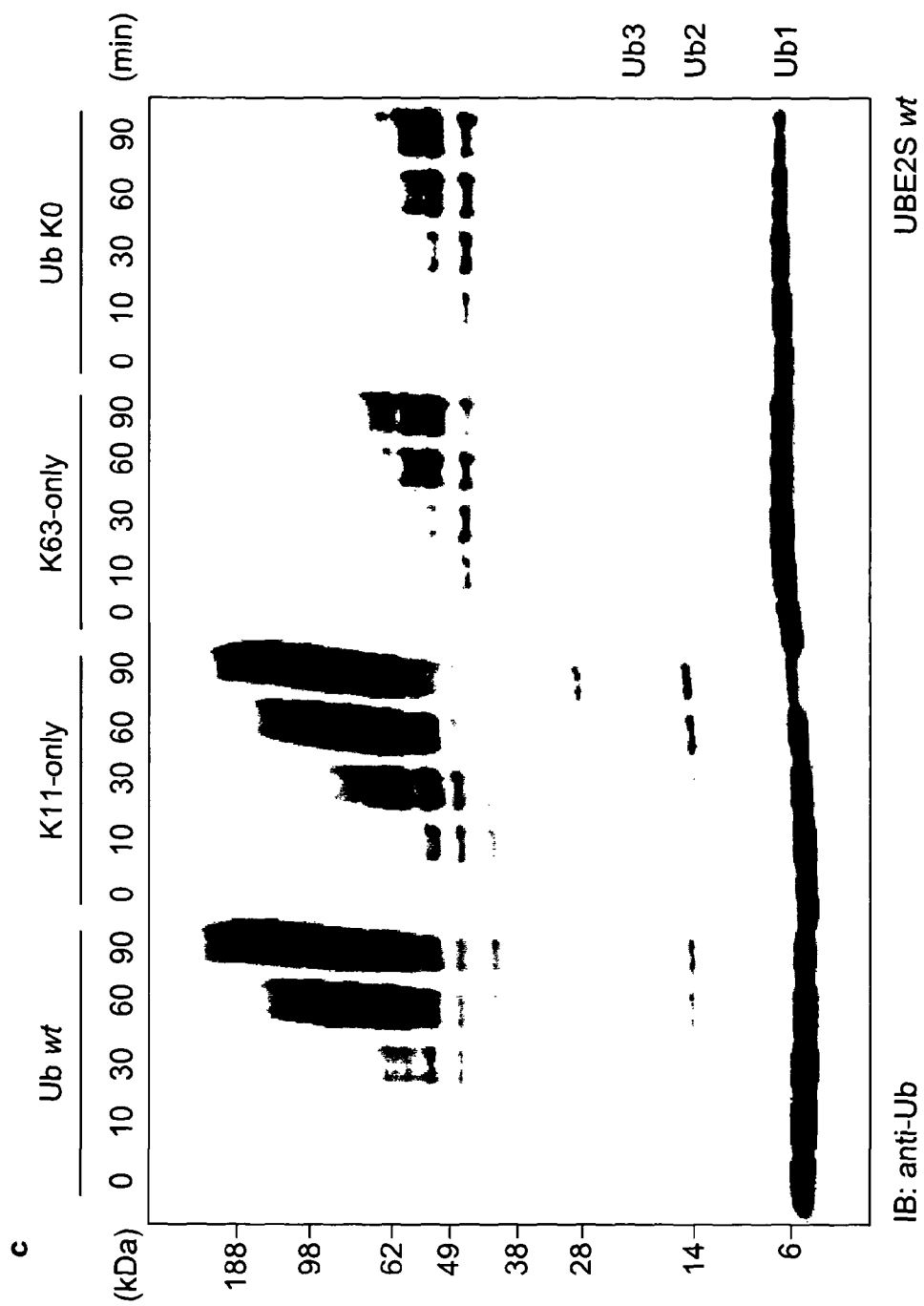

Unless defined otherwise, all technical scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.). All publications cited herein are incorporated herein by reference in their entirety for the purpose of describing and disclosing the methodologies, reagents, and tools reported in the publications that might be used in connection with the invention.

E2 enzymes, as referred to herein, are variously known as ubiquitin carrier proteins, ubiquitin conjugating enzymes or Ubcs. In many instances, E2 enzymes are thought to determine linkage specificity in polyubiquitin. 38 E2 enzymes have been identified in humans, as described in Ye and Rape, 2009. As noted above, they may be subdivided into three classes, of which class II enzymes have a C-terminal extension or tail attached to the Ubc catalytic domain (also referred to as the UBCc catalytic domain). This domain is recognised as a conserved domain, and is identifiable in any E2 enzyme.

Ubiquitin binding domains, or UBDs, are modular protein domains which bind non-covalently to ubiquitin. As noted above, UBDs are divisible into a number of different categories, including α-helical, zinc finger and pleckstrin homology domains, which are structurally diverse. Preferably, a UBD is a UBD as described in Dikic et al., 2009. Other UBDs may become recognised, and it is anticipated that these too will be useful in the present invention. In one embodiment, a UBD is a ZnF UBD, for example UBZ, NZF, A20-like ZnF or ZnF UBP, as described in Dikic et al., 2009.

A chimeric protein may be constructed by fusing a Ubc domain to a UBD, according to techniques known in the art. For example, polypeptide fusions may be created by ligating nucleic acids encoding the respective domains in-frame, and expressing the coding sequence thus created. The domains may be fused directly to one another, or may be separated by one or several additional amino acids, referred to as a linker. Where a linker separates the domains, said linker advantageously does not negatively influence the three-dimensional alignment of the domains in such a way that their functional cooperation is sterically hindered. The UBD is preferably C-terminal to the Ubc domain, effectively replacing the C-terminal extension in a Class II E2.

A chimeric enzyme is an enzyme that may comprise at least two heterologous domains. In this context, heterologous signifies that the domains are not found in the same position in a single polypeptide in vivo. Normally, this means that the domains are derived from two different proteins. The proteins themselves may be found in the same organism—for example, the proteins may both be human proteins.

The term "fusion protein" refers to a protein or polypeptide that has an amino acid sequence derived from two or more proteins, for example two heterologous domains as indicated above. The fusion protein may also include linking regions of amino acids between amino acid portions derived from separate proteins. Unrelated proteins or polypeptides may also be included in the fusion, for example immunoglobulin peptides, dimerising polypeptides, stabilizing polypeptides, amphiphilic peptides, or polypeptides which may comprise amino acid sequences that provide "tags" for targeting or purification of the protein.

In one embodiment, a chimeric enzyme may also be an enzyme in which the positioning, spacing or function of two endogenous domains has been changed, by manipulation, with respect to the wild-type enzyme. For example, a C-terminal extension in a class II E2 may be repositioned by adding or removing amino acids between it and the Ubc domain. Alternatively, the amino acid sequence of the C-terminal extension itself may be mutated, to introduce desired properties. Typically, such properties include the ability to bind ubiquitin.

A protein domain, as referred to herein, is a protein or fragment of a protein which is capable of independent folding to create a defined three-dimensional structure that imparts a property to the domain. Typically, the domain is identified by its amino acid sequence, usually by identifying certain limits in a protein structure which define the domain. Domains may be identified using domain databases such as, but not limited to PFAM, PRODOM, PROSITE, BLOCKS, PRINTS, SBASE, ISREC PROFILES, SAMRT, and PROCLASS. It will be understood that the precise limits of the domain, as defined by the amino acid sequence, may vary. For example, including extra amino acids which are not normally considered to be part of the domain is unlikely to affect the function of the domain. The use of interdomain linkers is commonplace in the art to link protein domains, both in nature and in artificial protein constructs. Such linkers typically comprise sequences present upstream or downstream of the joined domains in their natural context. Moreover, removing one or more amino acids from one end of a domain may be permissible, as long as a substantial part of the domain remains which is still able to fold in the correct manner to mediate the desired function. In one embodiment, therefore, a domain is a minimal independently-folding segment of a protein which possesses the desired functional characteristic. In the case of the Ubc domain, this function is the polymerisation of ubiquitin using the desired lysine linkage. In the case of the UBD, the function is to promote the formation of free ubiquitin polymers.

In one embodiment, the entire sequence of a domain as defined by primary amino acid sequence is used. In another embodiment, a sequence shortened by 1, 2, 3, 4, 5, 6, 7, 8, 9, 10, 15, 20 or more amino acids at the N and/or C terminus may be used.

The present invention increases the amount of free polyubiquitin produced by E2 enzymes, making the polyubiquitin available for any desired purpose. In this context, the production of free polyubiquitin may be increased by 10%, 15%, 20%, 25%, 50%, 75%, 100% or more. Free polyubiquitin refers to polyubiquitin chains, for example dimers, trimers, tetramers or longer chains, released into solution by the E2 enzyme rather than attached to a target.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

Ubc (UBCc) domains of E2 proteins share a consensus sequence, 141 amino acids in length. Comparison of Ubc domains suggests a consensus sequence SKRLQKELKDLKKDPPSGIS AEPVEENLLEWHGTIR GPPDTPYEGGIFKLDIEFP EDYPFKPPKVRFVTKI YHPPNVDENGKICLSI LKTHGWSPAY TLRTV-LLSLQSLLN EPNPSDPLNAEAAK LYKEN-REEFKKKAREWT [SEQ ID no 19]. The Ubc motif, [FY-WLS]-H-[PC]-[NH]-[LIV]-x(3,4)-G-x-[LIV]-C-[LIV]-x-[LIV], is underlined [SEQ ID no 20]. Preferably, the Ubc domain used in the present invention conforms to the consensus sequence, allowing for conservative amino acid substitutions. Substitutions to the conserved sequence may also be made which reflect deviation from the consensus seen in naturally-occurring Ubc domains. Therefore, the Ubc domain used in the present invention may be naturally occurring or synthetic. Synthetic domains may be designed according to the above consensus and constraints.

Naturally-occurring Ubc domains may be derived from proteins other than E2 enzymes.

Conservative amino acid substitutions generally follow the following scheme:

| Side chain | Members |
| --- | --- |
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

In the above table, amino acids identified in the same row are considered to have similar side-chains and may be substituted for each other with the least impact on protein structure and function.

A list of known E2 enzymes, identified by human gene names together with yeast homologue names, appears in Table 51 in the supplementary information supplied with Ye & Rape, 2009. In the context of the present invention, E2 enzymes may be selected from this list, and Ubc domains derived therefrom for use in constructing chimeric E2 enzymes.

For example, in order to improve the production of free Lys-11 conjugated polyubiquitin, UBE2C or UBE2S should be employed. In UBE2C the Ubc domain extends from residue 33 to residue 170 of the amino acid sequence.

In order to produce Lys-48 chains, UBE2G1, UBE2G2, UBE2K, UBE2R1 or UBE2R2 may be used. In UBE2G1, for example, the Ubc domain is located between residues 74 and 216 of the amino acid sequence.

Other E2 enzymes, and reported chain specificities, are set forth in Ye and Rape, 2009, as mentioned above.

Table 1 shows Seq IDs 1 to 13, which set forth exemplary nucleotide and amino acid sequences of human E2 enzymes, and identify the Ubc (UBCc) domains therein. Other sequences are available in databases, such as SWISSPROT, TrEMBL, NCBI, and the like.

TABLE 1

| Name | SEQ ID | UBCc position |
| --- | --- | --- |
| UBE2C | 1 | 33-170 |
| UBE2D1 | 2 | 4-142 |
| UBE2D2 | 3 | 4-142 |
| UBE2D3 | 4 | 4-142 |
| UBE2E2 | 5 | 59-196 |
| UBE2E3 | 6 | 65-202 |
| UBE2F | 7 | 35-180 |
| UBE2J1 | 8 | 12-119 |
| UBE2J2 | 9 | 14-127 |
| UBE2M | 10 | 33-166 |
| UBE2N | 11 | 5-144 |
| UBE2O | 12 | 958-1108 |
| UBE2S | 13 | 13-152 |

Ubc domains may be obtained from the sequences set forth above, or other E2 sequences known in the art, and covalently linked to UBD domains to create a chimeric protein. Alternatively, nucleic acids encoding domains suitable for generating chimeric E2 enzymes may be produced, for example, by restriction enzyme digestion of nucleic acids encoding the desired E2 enzyme, or by PCR amplification of a desired nucleic acid sequence using primers that flank the Ubc domain. Nucleic acids encoding E2 enzymes are known in the art and sequences therefore widely available in databases such as GENBANK. Restriction enzyme cutting sites and suitable primers may be identified using suitable software, or by eye.

The invention contemplates the use of natural Ubc domains that have been mutated. Mutation may be at the nucleic acid level, that is changes may be effected to the nucleic acid encoding a Ubc domain without changing the structure of the Ubc domain itself, as a result of redundancy in the genetic code. Such changes may, for example, confer improved expression in heterologous host cells by employing preferred codon usage patterns.

Other mutations will change the amino acid sequence of the Ubc domain. As noted above, this may take the form of additions to or deletions from the N and C termini of the domain. Moreover, changes may be made within the sequence of the Ubc domain, for example through substitution, addition or deletion of one or more amino acids. Conservative amino acid substitutions are preferred, as set forth above. For example, 1, 2, 3, 4, 5, 6, 7, 8, 9, 10, 15, 20 or more amino acids are added, deleted and/or substituted by other amino acids.

In a preferred embodiment, the naturally occurring Ubc sequence is used.

Expression of nucleic acids encoding chimeric E2 enzymes may be carried out in any suitable expression system. Expression systems are known in the art and may be obtained commercially or according to instructions provided in laboratory manuals.

More than 20 families of UBD have been identified. The first UBD to be identified was from S5a, a proteasome subunit, and this sequence was used in bioinformatic analyses to identify further domains, which were then shown to be bonafide UBDs. A pattern was identified, known as the ubiquiting-interacting motif (UIM). A second motif, the Ubiquitin-Associated domain (UBA), was first identified as a domain common to proteins involved in ubiquitin metabolism. This domain too was shown to bind ubiquitin. Further domains have been discovered, including CUE domains, which are associated with Endoplasmic Reticulum targeting, and the zinc finger NZF or PAZ domains, VHS and GLUE domains.

The UEV domain is a pleckstrin homology UBD which resembles s Ubc domain, but lacks the catalytic cysteine residue. For a description of UBD domains, see Hicke et al., 2005, and Dikic et al., 2009, especially Table 1 in the latter document.

UBDs useful in the present invention may be obtained from naturally-occurring polypeptides, or may be mutated forms of domains present in such polypeptides. As noted above, mutant proteins may be created by inserting, deleting or substituting nucleic acid residues in a gene encoding the protein. The foregoing guidelines for mutation of Ubc domains may be applied to UBDs.

Zinc finger UBOs are known, for instance, in HDAC6, where the UBD is located between residues 1133 and 1204 (SEQ ID No. 14); in RABEX5, wherein A20-like ZnF and MIU UBDs are located between amino acids 1 and 74 (SEQ ID No. 15); in NPL4, where it is between positions 104 and 246 (SEQ ID No. 16); in TAB2, where it lies between residues 663 and 693 (SEQ ID No. 17); and in IsoT, where it lies between residues 173 and 289 (SEQ ID No 18).

When selecting a UBD for fusing to an Ubc, it is preferred that the lysine specificity of the Ubc should be compatible with the binding of the UBD to ubiquitin. For example, if Lys-11 is the preferred linkage residue of the Ubc, the UBO preferably binds ubiquitin in such a manner as to leave Lys-11 accessible for chain extension with ubiquitin molecules.

A chimeric protein in accordance with the invention may comprise a Ubc domain fused to a UBO. The UBO is preferably C-terminal in the fusion, although N-terminal fusions are contemplated. Fusions may be created by covalent linkage of polypeptide domains, or ligation of nucleic acids encoding such domains in the form of restriction fragments, amplification fragments or both. Moreover, synthetic nucleic acids may be used to create synthetic or partially synthetic nucleic acids encoding a fusion protein in accordance with the invention.

Fusions useful in the present invention include UBE2S and UBE2C fusions, for the production of Lys-11 linked polyubiquitin. The Ubc domains of UBE2S and UBE2C may be ligated to UBDs from a variety of proteins. For example, zinc finger UBDs may be used, such as the domains derived from polymerase-h or polymerase-k, Tax1BP1, NPL4, Vps63, TAB2, TA83, RABEXS, A20, IsopeptidaseT (IsoT) and HDAC6.

Preferred combinations include the Ubc of UBE2S and the ZnF UBP domain of IsopeptidaseT, as well as the Ubc of UBE2S and the NZF of TAB2.

For example, the engineered UBE2S-UBD fusion protein is constructed making use of a naturally occurring NcoI restriction site in the human UBE2S sequence just before the Lys-rich tail (residue 196), and cloned into a vector such as pGEX6P1 (Amersham). The IsoT(USP5) ZnF UBP domain (residues 173-289) are amplified from cDNA with primers UBP-FW 5'-CCAAGGTT<u>CCATGG</u>TACGGCAGGTGTC-TAAGCATGCC-3' [SEQ ID No 21] and UBP-RV 5'-GCCTA<u>GCGGCCGC</u>TTATGTCTTCTGCATCTTCAGCAT-GTCG-ATG-3') [SEQ ID No 22]. The amplified fragment is ligated into the NcoI/NotI restriction sites present in the pGEX6P1-UBE2S expression plasmid. The protein is expressed in *E. coli* and purified.

The TAB2 NZF domain (Amino Acids 663-693; Nucleotides 1988-2079+STOP) is amplified using primers NZFfus663FW: CCAAGGTTCCATGGATGAGG-GAGCTC-AGTGGAATTG [SEQ ID No 23] and NZFfus693RV: GCCTAGCGGCCGCTTATC-AGAAAT-GCCTTGGCATCTC [SEQ ID No 24]. As with the ZnF domain, the amplified fragment is restriction digested and ligated into the NcoI/NotI restriction sites present in the pGEX6P1-UBE2S expression plasmid.

A similar technique may be employed for making Ubc-UBD fusions of choice.

A wide variety of expression systems are available for the production of chimeric polypeptides. For example, expression systems of both prokaryotic and eukaryotic origin may be used for the production of E2 fusion proteins.

Nucleic acid vectors are commonly used for protein expression. The term "vector" refers to a nucleic acid molecule that may be used to transport a second nucleic acid molecule into a cell, and/or express it therein. In one embodiment, the vector allows for replication of DNA sequences inserted into the vector. The vector may comprise a promoter to enhance expression of the nucleic acid molecule in at least some host cells. Vectors may replicate autonomously (extrachromosomal) or may be integrated into a host cell chromosome. In one embodiment, the vector may comprise an expression vector capable of producing a fusion protein derived from at least part of a nucleic acid sequence inserted into the vector.

A cloning vector may be a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An expression vector typically may comprise a transcription promoter, a gene, and a transcription terminator. Expression vectors may be autonomously replicating, or integrated into the host genome. Gene expression is usually placed under the control of a promoter, and such a gene is said to be operably linked to the promoter. Similarly, a regulatory element and a core promoter are operably linked if the regulatory element modulates the activity of the core promoter. The nucleic acid encoding the chimeric enzyme according to the invention is typically expressed under the control of a promoter in an expression vector.

To express a gene, a nucleic acid molecule encoding the protein must be operably linked to regulatory sequences that control transcriptional expression and then, introduced into a host cell. In addition to transcriptional regulatory sequences, such as promoters and enhancers, expression vectors may include transcriptional and translational regulatory sequences. The sequences used will be appropriate to the host, which may be prokaryotic or eukaryotic. The transcriptional and translational regulatory signals suitable for a mammalian host may be derived from viral sources, such as adenovirus, bovine papilloma virus, simian virus, or the like, in which the regulatory signals are associated with a particular gene that has a high level of expression. Suitable transcriptional and translational regulatory sequences also may be obtained from mammalian genes, such as actin, collagen, myosin, and metallothionein genes. Prokaryotic regulatory sequences may similarly be derived from viral genes, and are known in the art.

The inclusion of an affinity tag is useful for the identification or selection of cells expressing the fusion protein. Examples of affinity tags include polyHistidine tags (which have an affinity for nickel-chelating resin), c-myc tags, which are detected with anti-myc antibodies, calmodulin binding protein (isolated with calmodulin affinity chromatography), substance P, the RYIRS tag (which binds with anti-RYIRS antibodies), a hemagglutinin A epitope tag, which is detected with an antibody, the Glu-Glu tag, and the FLAG tag (which binds with anti-FLAG antibodies). Nucleic acid molecules encoding such peptide tags are available, for example, from Sigma-Aldrich Corporation (St. Louis, Mo., USA).

The gram-negative bacterium *E. coli* is widely used as a host for heterologous gene expression. Although large amounts of heterologous protein may accumulate inside the cell, this expression system is effective in the context of the present invention. Suitable strains of *E. coli* include BL21 (DE3), BL21(DE3)pLysS, BL21(DE3)pLysE, DH1, DH41, DH5, DH51, DH51F', DH51MCR, DH10B, DH10B/p3, DH11S, C600, HB101, JM101, JM105, JM109, JM110, K38, RR1, Y1088, Y1089, CSH18, ER1451, and ER1647.

Bacteria from the genus *Bacillus* are also suitable as heterologous hosts, and have capability to secrete proteins into the culture medium. Other bacteria suitable as hosts are those from the genera *Streptomyces* and *Pseudomonas*. Suitable strains of *Bacillus subtilus* include BR151, YB886, M1119, M1120, and B170 (see, for example, Hardy, "*Bacillus* Cloning Methods," in DNA Cloning: A Practical Approach, Glover (ed.) (IRL Press 1985)). Standard techniques for propagating vectors in prokaryotic hosts are well-known to those of skill in the art (see, for example, Ausubel 1995; Wu et al., Methods in Gene Biotechnology (CRC Press, Inc. 1997)).

Eukaryotic hosts such as yeasts or other fungi may be used. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable eukaryotic host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products.

In some embodiments, the fusion proteins may be expressed as GST fusions. For example, the pGEX vector system employs a GST fusion. Use of GST as a fusion partner provides an inducible expressions system which facilitates the production of proteins in the *E. coli* system. Proteins expressed using this system may be isolated using a glutathione capture resin.

For example, recombinant GST-UBE2S constructs are expressed in Rosetta 2 (DE3) placI cels (Novagen). 1 L cultures of cells are induced at $OD_{600}$ of 0.6 with 250 µM IPTG and proteins are expressed at 20° C. overnight. Cells are harvested and flash-frozen. 30 ml lysis buffer containing 270 mM sucrose, 50 mM Tris (pH 8.0), 50 mM NaF, 1 protease inhibitor cocktail tablet (Roche) (0.1% v/v (3-mercaptoethanol, 1 mg/ml lysozyme and 0.1 mg/ml DNase) are added per liter of culture. After sonication, cell lysates are cleared using a Sorvall SS-34 rotor (18,000 rpm, 30 min, 4° C.) and supernatants are incubated with Glutathione Sepharose 4B (GE Healthcare) for 1 h to immobilize soluble GST fusion proteins. Subsequently, the sepharose beads are washed with 500 ml high salt buffer [500 mM NaCl, 25 mM Tris (pH 8.5), 5 mM DTT] and 300 ml low salt buffer [150 mM NaCl, 25 mM Tris (pH 8.5), 5 mM DTT]. For site-specific cleavage of the GST tag, immobilized fusion proteins are incubated with 30 mM PreScission protease (GE Healthcare) overnight. Cleaved proteins are eluted with low salt buffer and flash-frozen in liquid nitrogen. All samples are >95% pure after purification.

The chimeric E2 enzymes of the invention produce enhanced levels of free polyubiquitin, compared to naturally occurring E2. Assays for ubiquitination are known in the art; for instance, a description of such assays, and relevant background, is set forth, for example, in WO2009134897, US2006088901 and WO2004020674. Ubiquitination assays kits are available commercially, for instance from Cisbio, Bedford, Mass., USA; Invitrogen, Carlsbad, Calif., USA; and Enzo Lifesciences, Plymouth Meeting, Pa., USA.

In general, an assay for the production of free ubiquitin requires the incubation of E1 enzyme, the chimeric E2 according to the invention and monomeric ubiquitin in the presence of ATP in a buffer solution.

E1 enzymes are available commercially, for instance from Enzo Lifesciences. A list of E1 enzymes is set forth in Table 1 of WO2004020674.

In one embodiment, ubiquitin may be labelled, to facilitate its subsequent detection or isolation.

In one embodiment, 30 µl reactions may be carried out at 37° C. containing 25 ng ubiquitin-activating enzyme (E1), 2 µg ubiquitin conjugating enzyme (E2), 5 µg ubiquitin, 10 mM ATP, 40 mM Tris (pH 7.5), 10 mM $MgCl_2$ and 0.6 mM DTT. After 1 h the reaction is stopped by addition of 10 p14×LDS sample buffer (Invitrogen), resolved by SDS-PAGE on 4-12% precast gels and subjected to Western analysis using rabbit polyclonal anti-ubiquitin antibody (Upstate).

The scale of the reactions may be increased, if necessary. Performing the reaction with naturally occurring E2S does not result in the formation of significant amounts of polyubiquitin. However, using a chimeric E2 according to the invention, polyubiquitin chains may be isolated and purified.

In one embodiment, ubiquitin dimers are synthesized by incubating 16 µg E1 enzyme, 100 µg UBE2SAC, 12.5 mg ubiquitin, 10 mM ATP, 40 mM Tris (pH 7.5), 10 mM $MgCl_2$ and 0.6 mM DTT at 37° C. overnight. Subsequently, 50 mM DTT is added to the reaction before further dilution with 14 ml of 50 mM ammonium acetate (pH 4.5).

K11-finked diubiquitin may be purified by cation exchange using a MonoS column (GE Healthcare) and concentrated to 5 mg/ml. Crystals are formed after 1 day from 3 M NaCl and 0.1 M citric acid (pH 3.5). Crystals may be soaked in mother liquor containing 15% ethylene glycol before freezing in liquid nitrogen.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Analysis of E2 Enzymes Involved in K11 Chain Formation

For the assembly of free K48- and K63-linked ubiquitin chains, specific E2 enzymes have been described, and the biology of these posttranslational modifications is now known in great detail. In order to study the elusive K11 linkage, Applicants analyzed the in vitro properties of two human E2 conjugating enzymes that have been associated with this chain type, namely UBE2C/UbcH10 (Jin et al., 2008) and UBE2S/E2-EPF (Baboshina & Haas, 1996). Applicants tested whether UBE2S and UBE2C would assemble unattached polyubiquitin chains in vitro in absence of an E3 ligase. Analytical assays were carried out in 30 µl reactions at 37° C. containing 250 nM ubiquitin-activating enzyme (E1), 2.8 µM (UBE2S) or 3.4 µM (UBE2C) ubiquitin conjugating enzyme (E2), 19.5 µM ubiquitin, 10 mM ATP, 40 mM Tris (pH 7.5), 10 mM $MgCl_2$ and 0.6 mM OTT. After 1 h the reaction was stopped by addition of 10 µl 4×LDS sample buffer (Invitrogen), resolved by SDS-PAGE on 4-12% precast gels and subjected to Western analysis using rabbit polyclonal anti-ubiquitin antibody (Upstate). Applicants found that UBE2S generated small amounts of free diubiquitin, as judged by the appearance of ubiquitin dimers on reducing SDS PAGE gels (FIG. 1*a*), while UBE2C did not assemble unattached ubiquitin chains (FIG. 1*b*). UBE2S, but not UBE2C, also underwent autoubiquitination, resulting in the appearance of high molecular weight species of UBE2S (FIG. 1*a*). Linkage type analysis using single-Lys ubiquitin mutants (K6-only, K11-only etc.) revealed that UBE2S assembled K11 linkages specifically (FIG. 1*a*), since ubiquitin dimers as well as high molecular weight forms of UBE2S were only observed with the KU-only ubiquitin mutant (FIG. 1a). UBE2S autoubiquitinated several of its 17 Lys residues, however with ubiquitin mutants lacking K11, these monoubiquitin modifications were not extended (FIG. 1a, c), and autoubiquitination with Lysless (K0) and K63-only ubiquitin followed similar kinetics resulting in 6-7 distinct multi-monoubiquitinated bands of UBE2S (FIG. 1c). To verify that UBE2S was K11-specific also with wild-type ubiquitin, Applicants performed LC-MS/MS analysis of trypsinized diubiquitin.

LC-MS/MS was carried out by nanoflow reverse phase liquid chromatography (using a U3000 from Dionex) coupled online to a Linear Ion Trap (LTQ)-Orbitrap XL mass spectrometer (Thermo Scientific). Briefly, the LC separation was performed using a C18 PepMap capillary column (75 µm ID×150 mm; Dionex) and the peptides were eluted using a linear gradient from 5% B to 50% B over 40 minutes at a flow rate of 200 mL/min (solvent A: 98% $H_2O$; 2% acetonitrile in 0.1% formic acid; solvent B: 90% acetonitrile in 0.1% formic acid). The eluted peptides were electrosprayed into the mass spectrometer via a nanoelectrospray source fitted with a PicoTip emitter (New Objective). A cycle of one full FT scan mass spectrum (350-2000 m/z, resolution of 60 000 at m/z 400) was followed by 6 data-dependent MS/MS acquired in the linear ion trap with normalized collision energy (setting of 35%). Target ions already selected for MS/MS were dynamically excluded for 60 s. Peptides were identified from MS/MS spectra by searching against a Swissprot database using the Mascot search algorithm (matrixscience.com) and Proteome Discoverer (Thermo Fisher Scientific). Oxidation of methionine, GlyGly and LeuArgGlyGly addition on Lysine residues were used as variable modifications. Initial mass tolerance was set to 10 ppm for peptide parent mass, 0.8 Da for fragment masses and enzyme restriction was set to trypsin specificity with 2 missed cleavages.

Applicants detected peptides derived from K11-linked diubiquitin, and with significantly less intensity also from K48- and K63-linked diubiquitin. Other linkages were not detected. Applicants focused on UBE2S and set out to harness its capability to produce free K11-linked ubiquitin chains.

Figure 2:
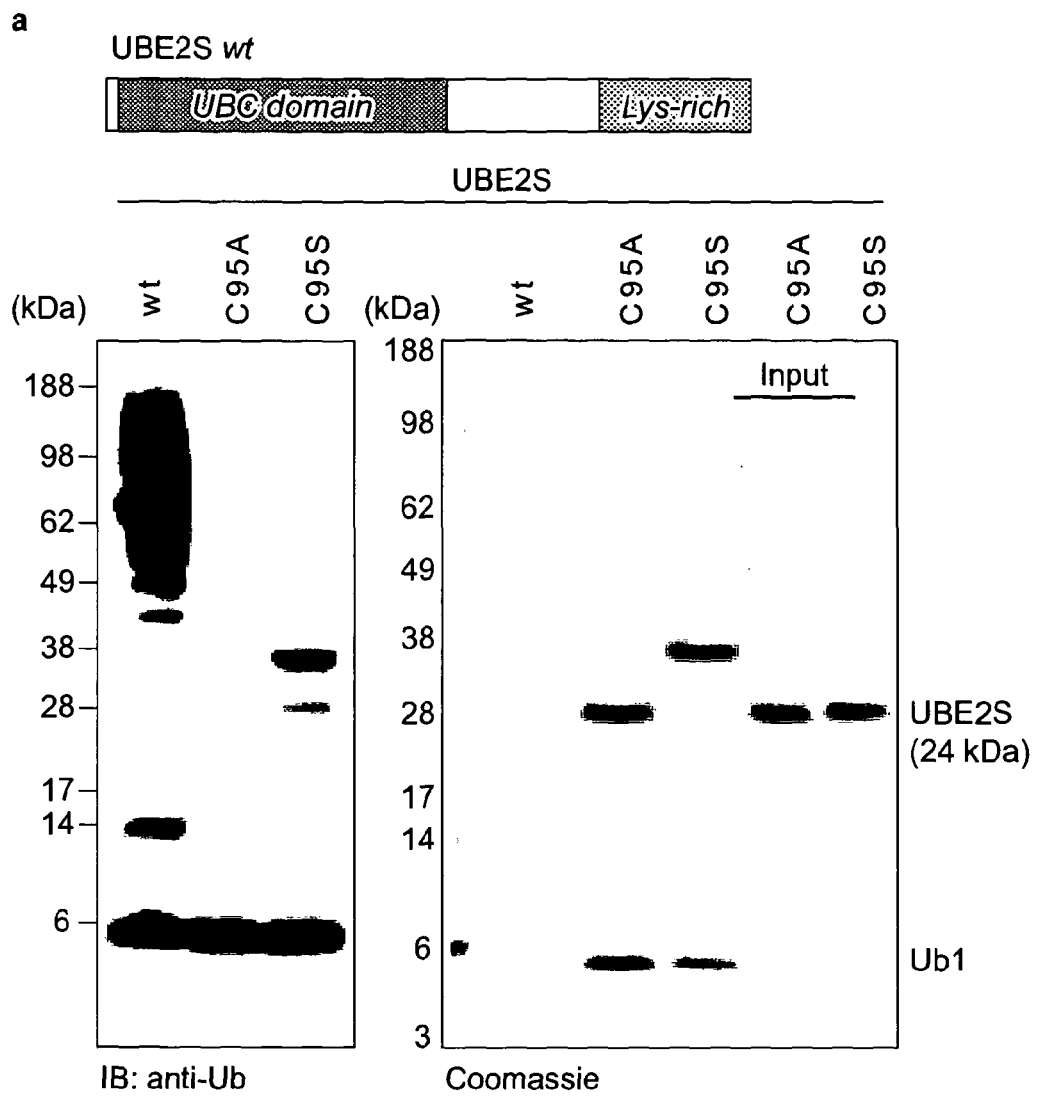
FIG. 2: Assembly of K11-linked diubiquitin. (a) Domain structure of UBE2S, and autoubiquitination reactions with UBE2S wild-type and catalytic mutants. (b) UBE2S autoubiquitination occurs in cis. Wild-type UBE2S was mixed with GST-tagged inactive UBE2S$^{C95A}$, and after precipitation of the GST-tagged protein, ubiquitination in supernatant (left) and precipitate (right) is analyzed. (c) Removal of the Lys-rich tail of UBE2S decreases autoubiquitination while preserving K11 specificity. (d) Purification of K11-linked diubiquitin by cation exchange chromatography. The integrated peak area (mAU*ml) is indicated. A gel showing protein-containing fractions is shown as an inset.
Figure 2:
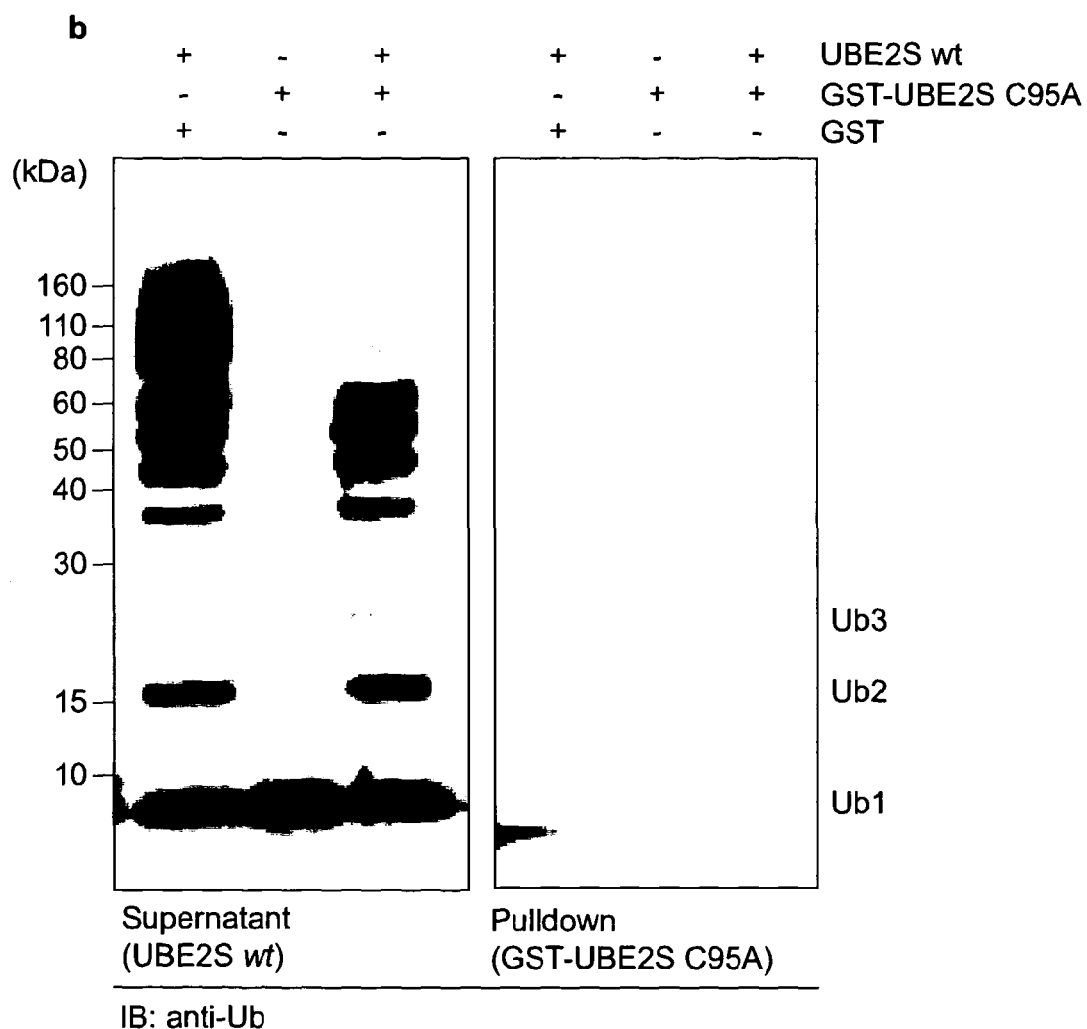
Figure 2:
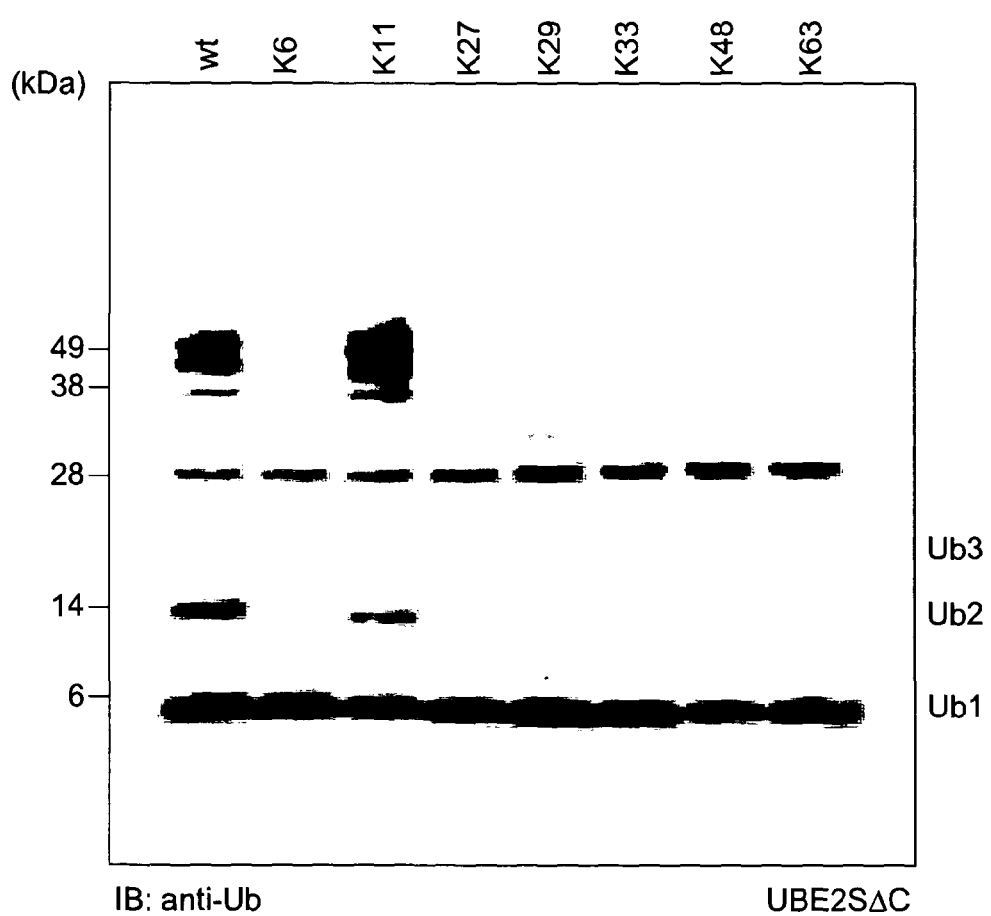
Figure 2:
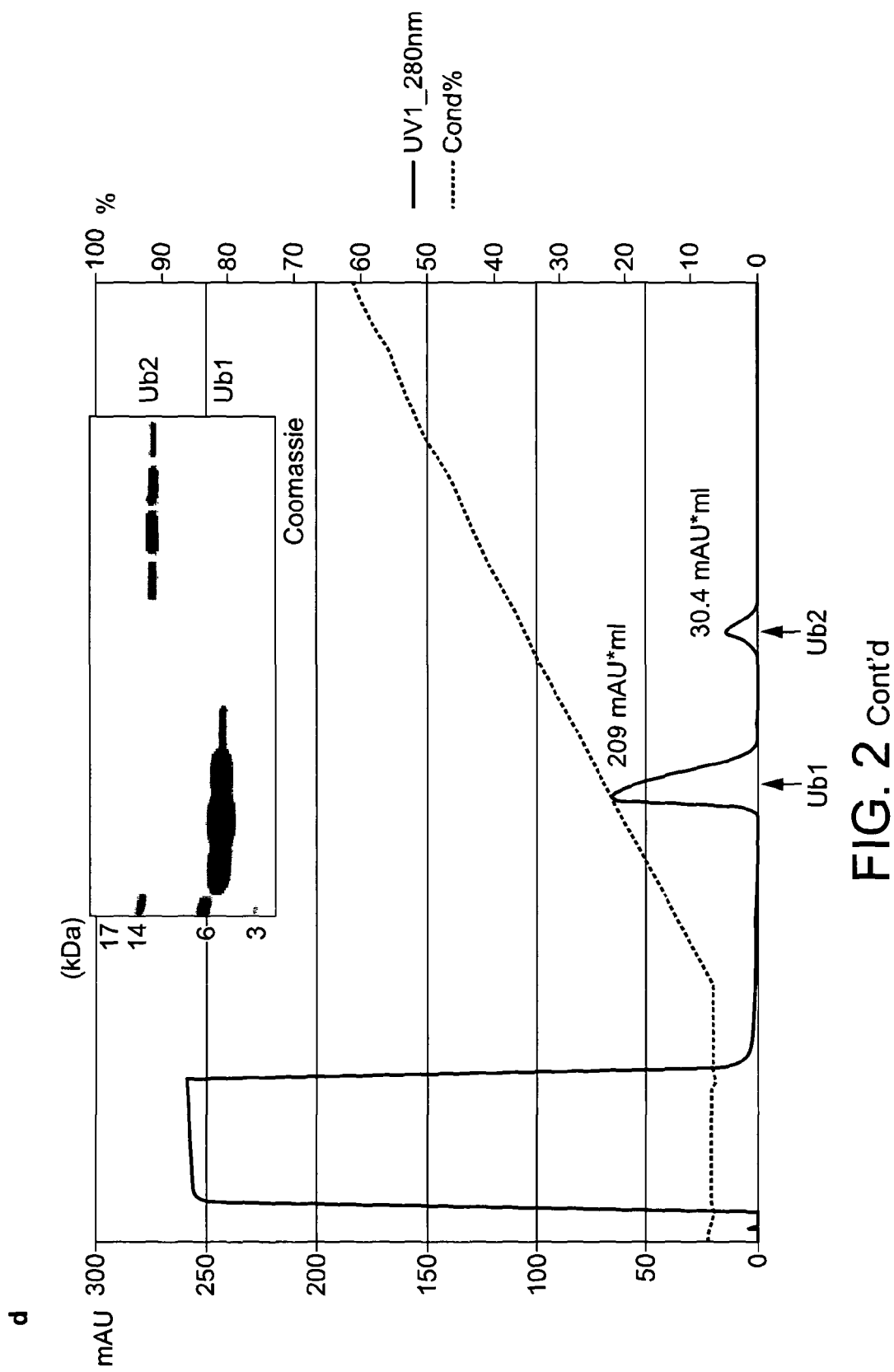

Human UBE2S may comprise 222 residues with an N-terminal conserved catalytic Ubc domain spanning residues 1-156. The very C-terminal 25 residues of UBE2S encompass nine Lys residues that are conserved in UBE2S homologs (ensembl.org), while the remaining 40 residues form a non-conserved Lys-free linker (FIG. 2a). Mutation of the catalytic Cys residue in the Ubc domain to Ala (UBE2S$^{C95A}$) rendered UBE2S inactive, while mutation to Ser (UBE2S$^{C95S}$) acted as a ubiquitin-trapping mutant, in which the Ser residue was still charged with ubiquitin by the E1 enzyme, but failed to discharge efficiently, similar to what has been reported for UBE2N/Ubc1317 (FIG. 2a).

Autoubiquitination of UBE2S occurred in cis, as wild-type UBE2S was unable to ubiquitinate GST-tagged UBE2S$^{C95A}$ in trans, despite being able to autoubiquitinate itself (FIG. 2b). The autoubiquitination of UBE2S appeared to be favored compared to formation of free K11-linked chains, and free chain production is inefficient. The Lys-rich tail of UBE2S is a likely target for autoubiquitination. Removal of the last 25 residues (UBE2SAC) reduced autoubiquitination (FIG. 2c), increased formation of free diubiquitin (data not shown), and the enzyme remained specific for K11 linkages (FIG. 2c). From 25 mg input ubiquitin, ~1 mg K11-linked diubiquitin could be purified by cation exchange (FIG. 2d).

Example 2

Generation of K11-Linked Ubiquitin Tetramers

In order to increase the yields of K11-linked dimers and to obtain longer polymers, Applicants reverted to protein engineering to create an UBE2S variant with increased capability to form free ubiquitin chains. Having established that the Lys-rich tail of UBE2S is polyubiquitinated by UBE2S in a cis reaction, Applicants replaced this tail (residues 196-222) with the ubiquitin binding ZnF-UBP domain of human USP5/IsoT (residues 173-289) (Reyes-Turcu et al., 2006; FIG. 3a). This UBD has two advantageous features: it binds ubiquitin with nanomolar affinity, and interacts with the free C-terminal tail of ubiquitin leaving the Lys11 side chain accessible for chain elongation. The UBE2S-UBD fusion protein was significantly more efficient in producing ubiquitin dimers, trimers, and tetramers.

Figure 3:
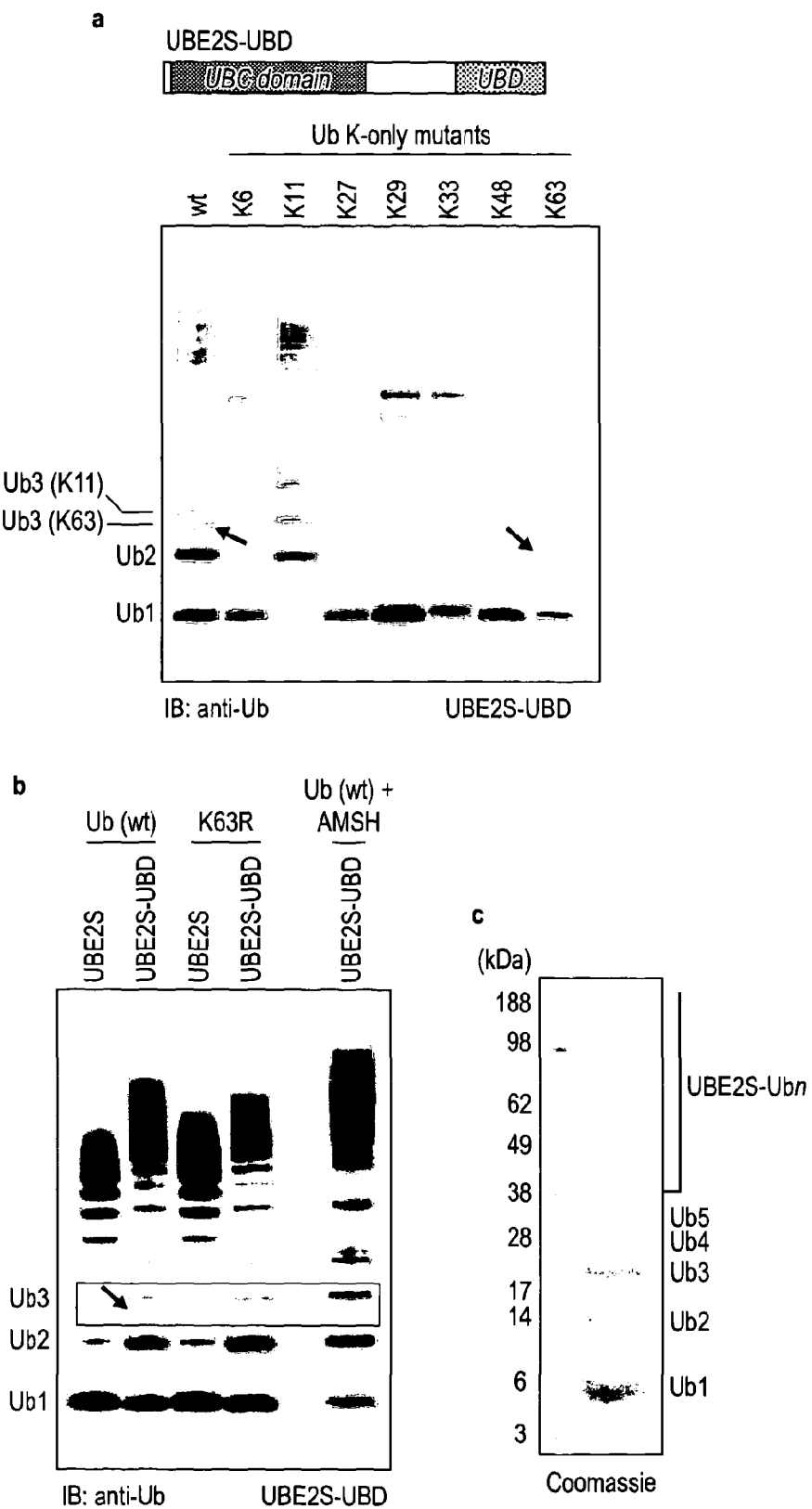
FIG. 3: Assembly of K11-linked tetraubiquitin. (a) UBE2S engineering to increase yields of free K11-linked ubiquitin chains. The C-terminal tail was replaced with the ZnF-UBP domain of USP5/IsoT. The fusion protein assembles free chains of up to five ubiquitin molecules, yet it is less specific and also incorporates K63-linkages with wild-type and K63-only ubiquitin (indicated by arrows). (b) Incorporation of K63-linkages may be counteracted by using a K63R ubiquitin mutant, or by including the K63-specific DUB AMSH in the reaction, as observed by disappearance of the faster migrating K63-linkage contamination. (c) 5 μl aliquot of a 1 ml chain assembly reaction using 25 mg ubiquitin shows that di-, tri- and tetraubiquitin is generated in milligram quantities. (d) Cation exchange chromatography was used to purify K11-linked ubiquitin chains. The integrated peak area (mAU*ml) is specified. A gel showing protein-containing fractions is shown as an inset. (e) Purified ubiquitin tetramers of K11, K48, K63 and linear linkages have different electrophoretic mobility on 4-12% SDS-PAGE gels.
Figure 3:
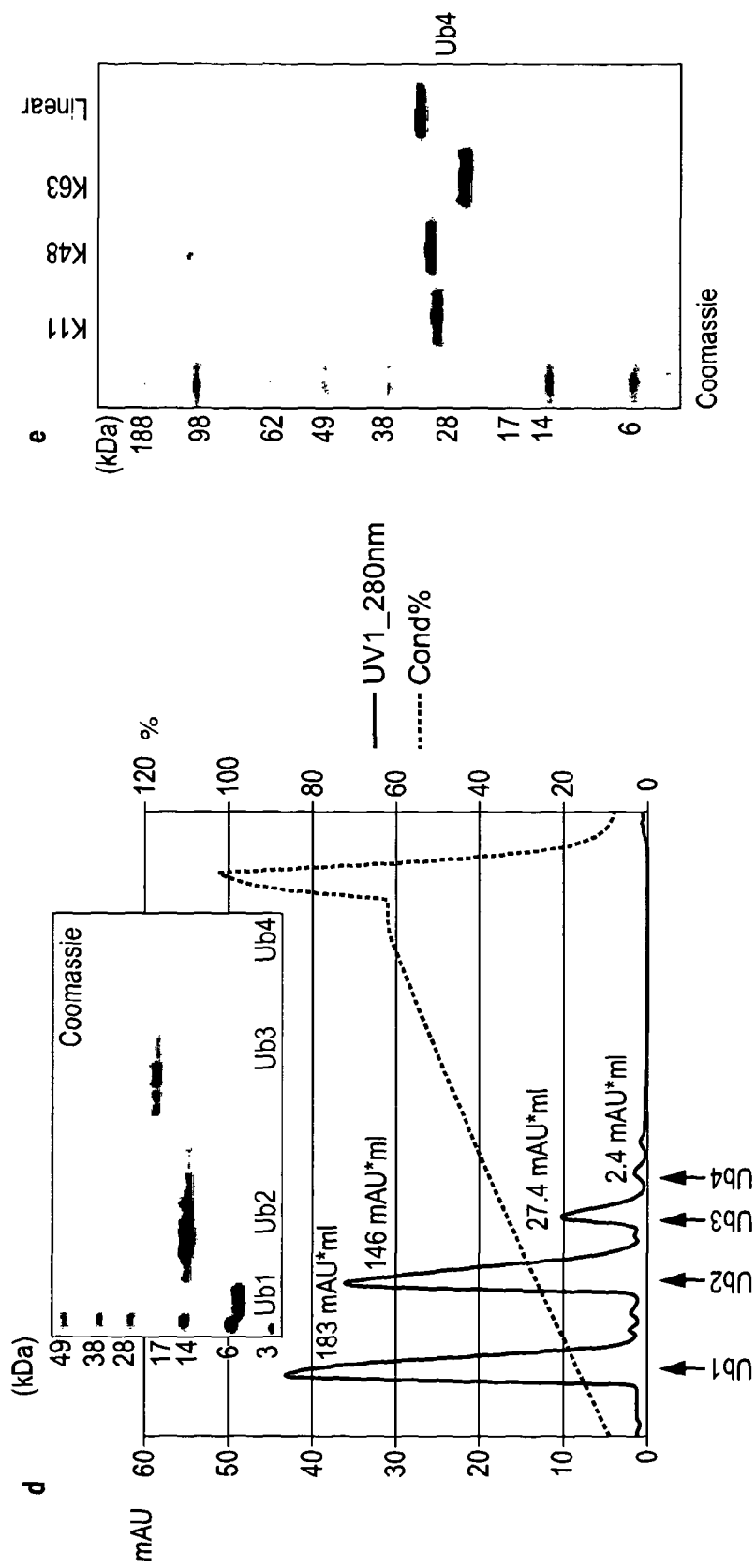

Ubiquitin tetramers were synthesized by incubating 250 nM E1 enzyme, 4.8 µM UBE2S-UBD, 2.9 mM ubiquitin, 400 nM AMSH, 10 mM ATP, 40 mM Tris (pH 7.5), 10 mM $MgCl_2$ and 0.6 mM DTT in a 1 ml reaction at 37° C. After 1.5 hours 400 nM AMSH was added again to counteract the formation of K63-linked ubiquitin chains. After 3 hours, 50 mM DTT was added to the reaction before further dilution with 14 ml of 50 mM ammonium acetate (pH 4.5). K11-linked di-, tri- and tetraubiquitin were purified by cation exchange using a MonoS column (GE Healthcare) (FIG. 3). It was also possible to use K11-linked diubiquitin as input material to obtain tetraubiquitin.

Specificity analysis showed that UBE2S-UBD also incorporated K63-linkages in these oligomers (see K63-only mutant in FIG. 3a). Two distinct trimer bands were observed in reactions using wild-type ubiquitin, but not with the K11-only ubiquitin mutant, indicating alternating or branched linkages with wild-type ubiquitin, since differently linked ubiquitin chains have distinct electrophoretic mobility (FIG. 3a, b). Two linkage types (K11 and K63) in the wild-type ubiquitin reaction were further confirmed by LC-MS/MS analysis.

Formation of K63-linkages could be counteracted by either using the ubiquitin K63R mutant, or by incubation with the K63-specific deubiquitinase AMSH (McCullough et al., 2004; FIG. 3b). Indeed, AMSH removed only the faster migrating of the two triubiquitin bands, showing that a chain with alternate linkages had been created by UBE2S-UBD (FIG. 3b). When Applicants included AMSH directly in the assembly reactions, Applicants were able to remove the contaminating K63 linkages in situ (FIG. 3b). This protocol allowed large scale generation and purification of K11-linked di-, tri- and tetraubiquitin (FIG. 3c, d, e) with improved yields. Almost 50% of the input ubiquitin was converted into K11-linked oligomers using UBE2S-UBD, while UBE2SAC only assembled 15% of input ubiquitin into K11-linked dimers (FIG. 3b, compare integrated peak area in FIGS. 2d and 3d).

Example 3

Structure of K11-Linked Polyubiquitin

Generation of K11-linked ubiquitin chains in large quantities allowed detailed structural analysis of this chain type.

Large-scale ubiquitin chain assembly was carried out in 1 ml reactions. Ubiquitin dimers were synthesized by incubating 250 nM E1 enzyme, 4.8 µM UBE2SAC, 1.5 mM ubiquitin, 10 mM ATP, 40 mM Tris (pH 7.5), 10 mM $MgCl_2$ and 0.6 mM DTT at 37° C. overnight. Subsequently, 50 mM DTT was added to the reaction before further dilution with 14 ml of 50 mM ammonium acetate (pH 4.5) to precipitate enzymes. The solution was filtered through a 0.2 μm syringe filter and K11-linked diubiquitin was purified by cation exchange using a MonoS column (GE Healthcare) and concentrated to 5 mg/ml. Crystals formed after 1 day from 3M NaCl and 0.1 M citric acid (pH 3.5). Before freezing in liquid nitrogen, crystals were soaked in mother liquor containing 15% ethylene glycol.

Figure 5:
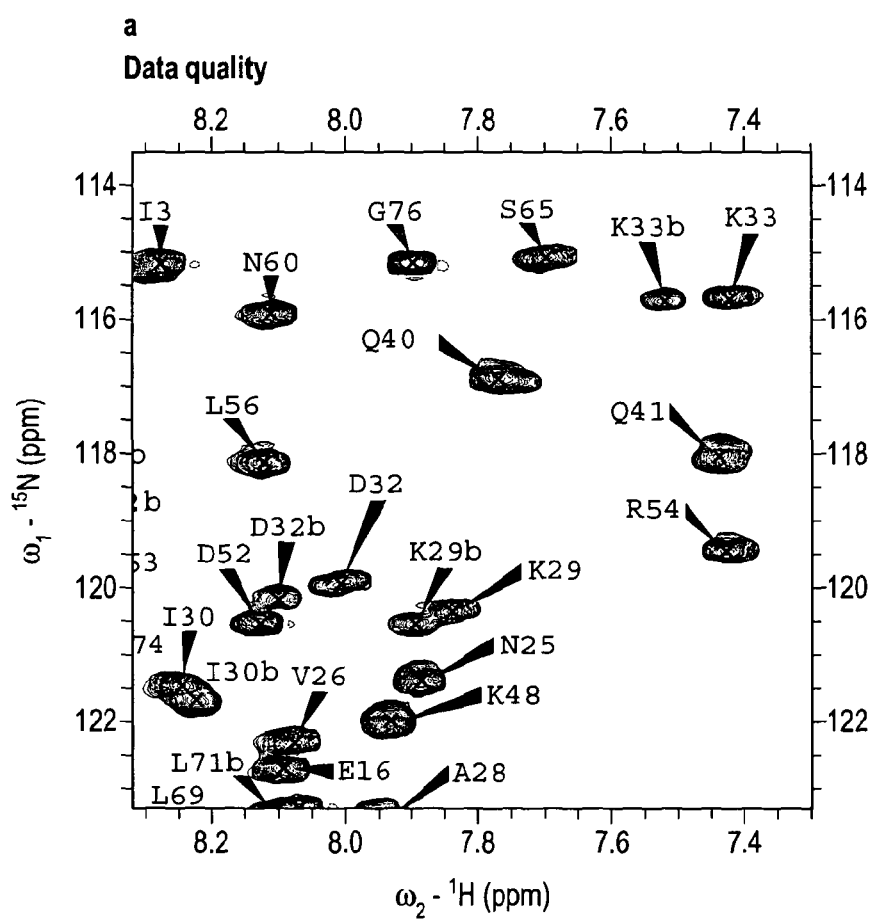
FIG. 5: NMR Solution studies of K11-linked diubiquitin. (a) Overlay of 15N, 1H HSQC spectra of ubiquitin K63R (red) onto K11-linked diubiquitin K63R (blue). The expansion illustrates the doubling of peaks observed for Lys29, Ile30, Asp32 and Lys33. The signal for Asp52 is unperturbed. (b, c) Weighted chemical shift perturbation according to residue number for K11-linked diubiquitin with both molecules $^{13}$C, $^{15}$N-labeled (blue, K63R ubiquitin mutant) or only labeled distally (orange, K11R ubiquitin mutant). Shown are chemical shift perturbations observed for doubled peaks calculated as the weighted difference between the chemical shift position in the K11-linked diubiquitin mutants and their respective monoubiquitin counterparts at pH7.4 (b) and pH 3.5 (c). Stars (*) indicate exchange-broadened residues, and arrows indicate K29 and K33. (d) Combined chemical shift perturbation differences for K48- and K63-linked diubiquitin (Tenno et al., 2004). (e) Comparison of the proximal K11-linked diubiquitin interface in a view indicated by the arrow (left). Surface map of interacting residues from NMR (middle, orange, with shifting residues in blue, and Pro residues in yellow) and from the crystal interaction (right, yellow with interface resides in marine, according to the PISA server, ebi.ac.uk/pdbe/prot_int/pistart.html). (f) Comparison of the distal K11 diubiquitin interface, coloured as in (c), as viewed indicated by the arrow in the left picture. The 2nd image shows perturbed residues obtained from the distally labeled sample, and the third image from the fully labeled diubiquitin. The fourth image corresponds to the crystal structure interface. Asp39 and Glu52, which form part of the crystallographic interface but are not perturbed in solution, are circled. A white surface indicates exchange-broadened residues.
Figure 5:
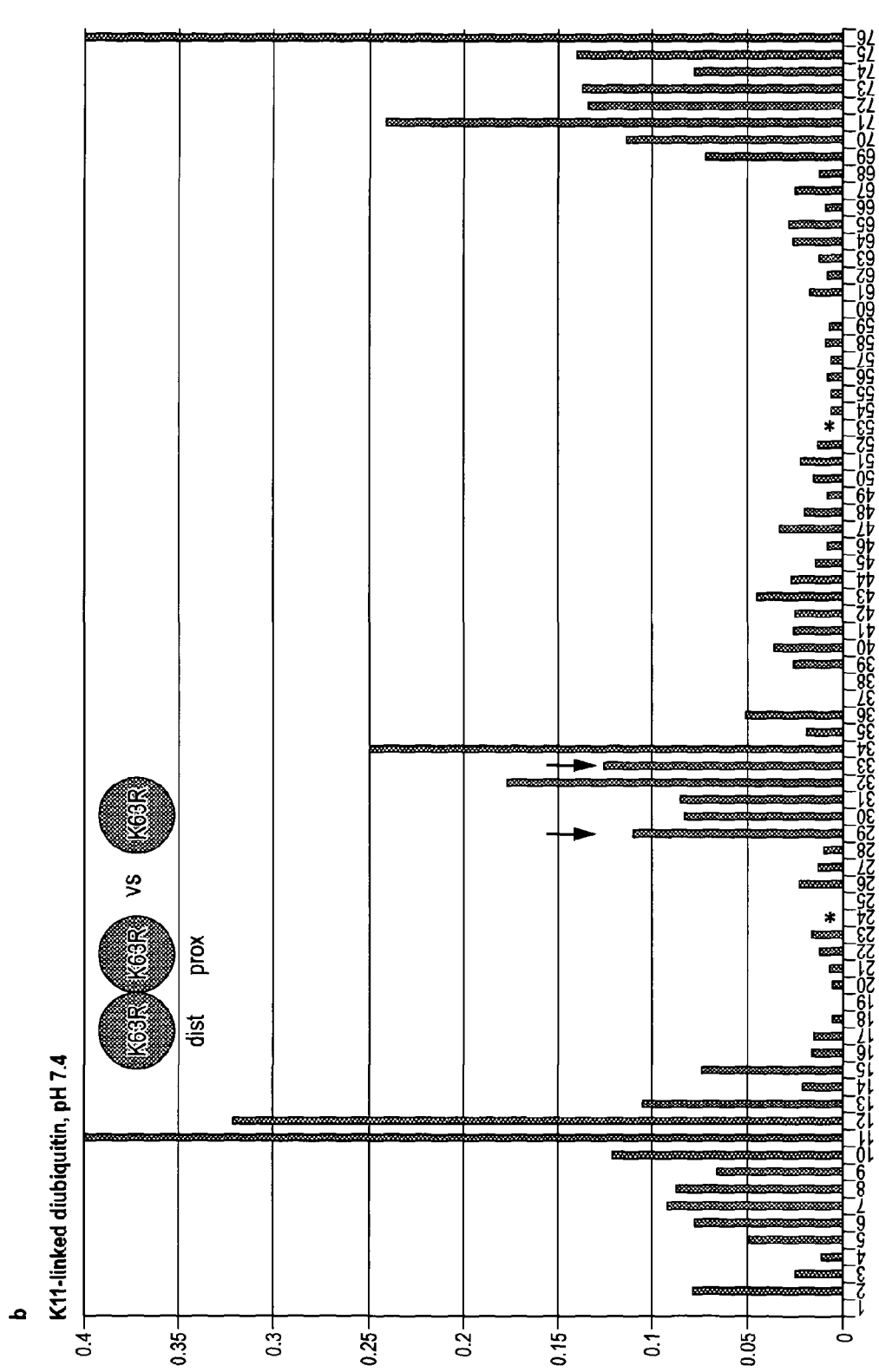
Figure 5:
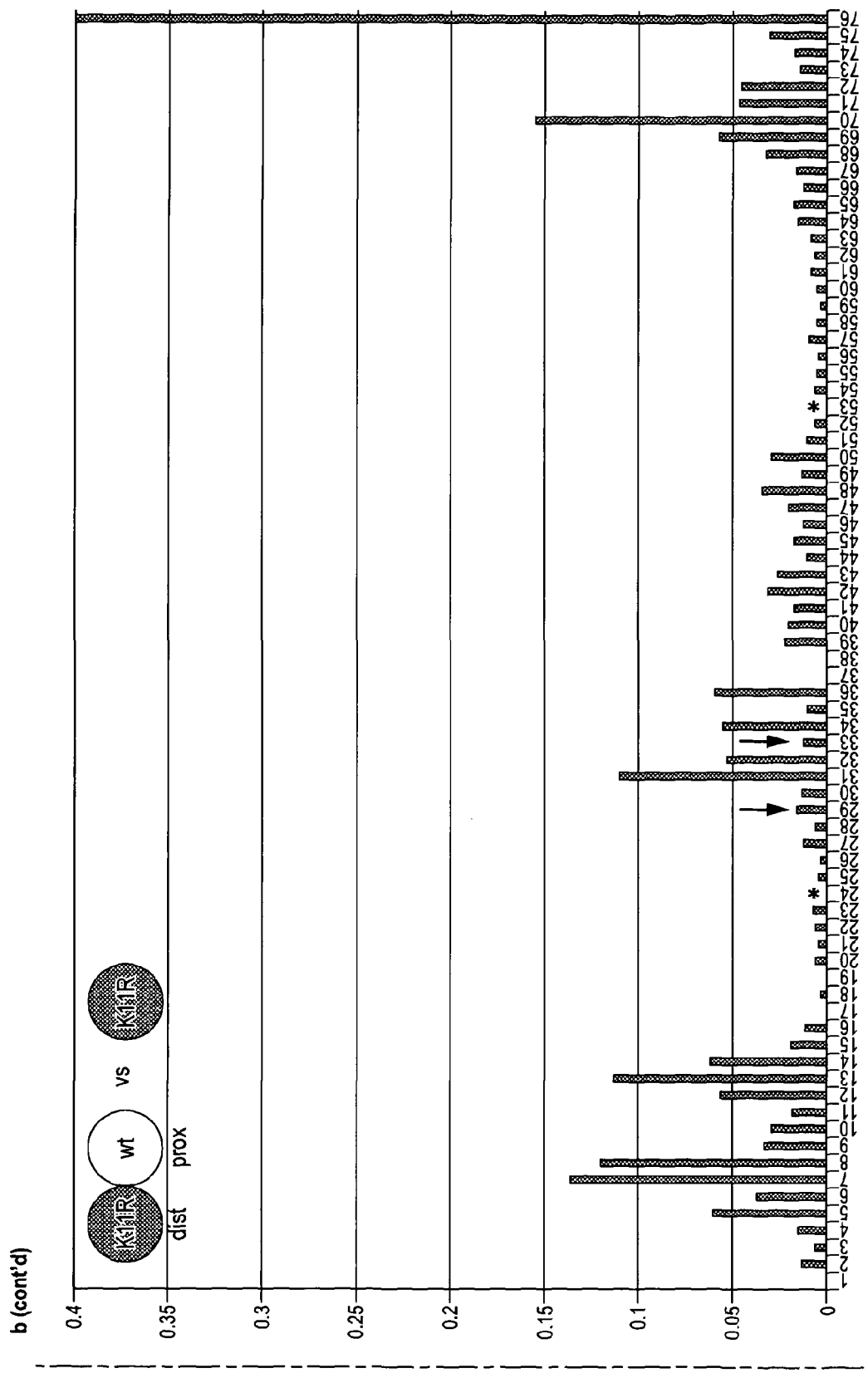
Figure 5:
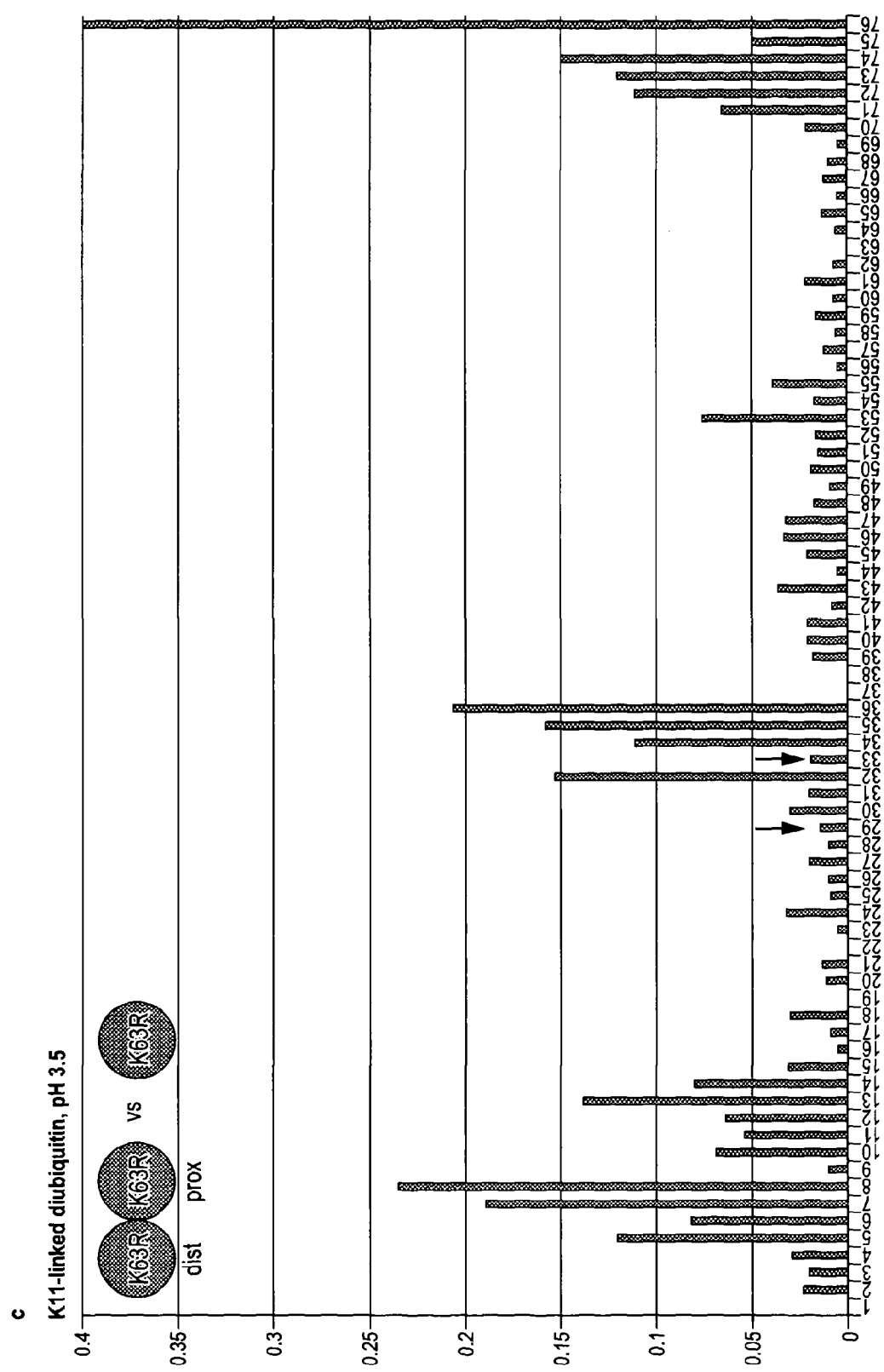
Figure 5:
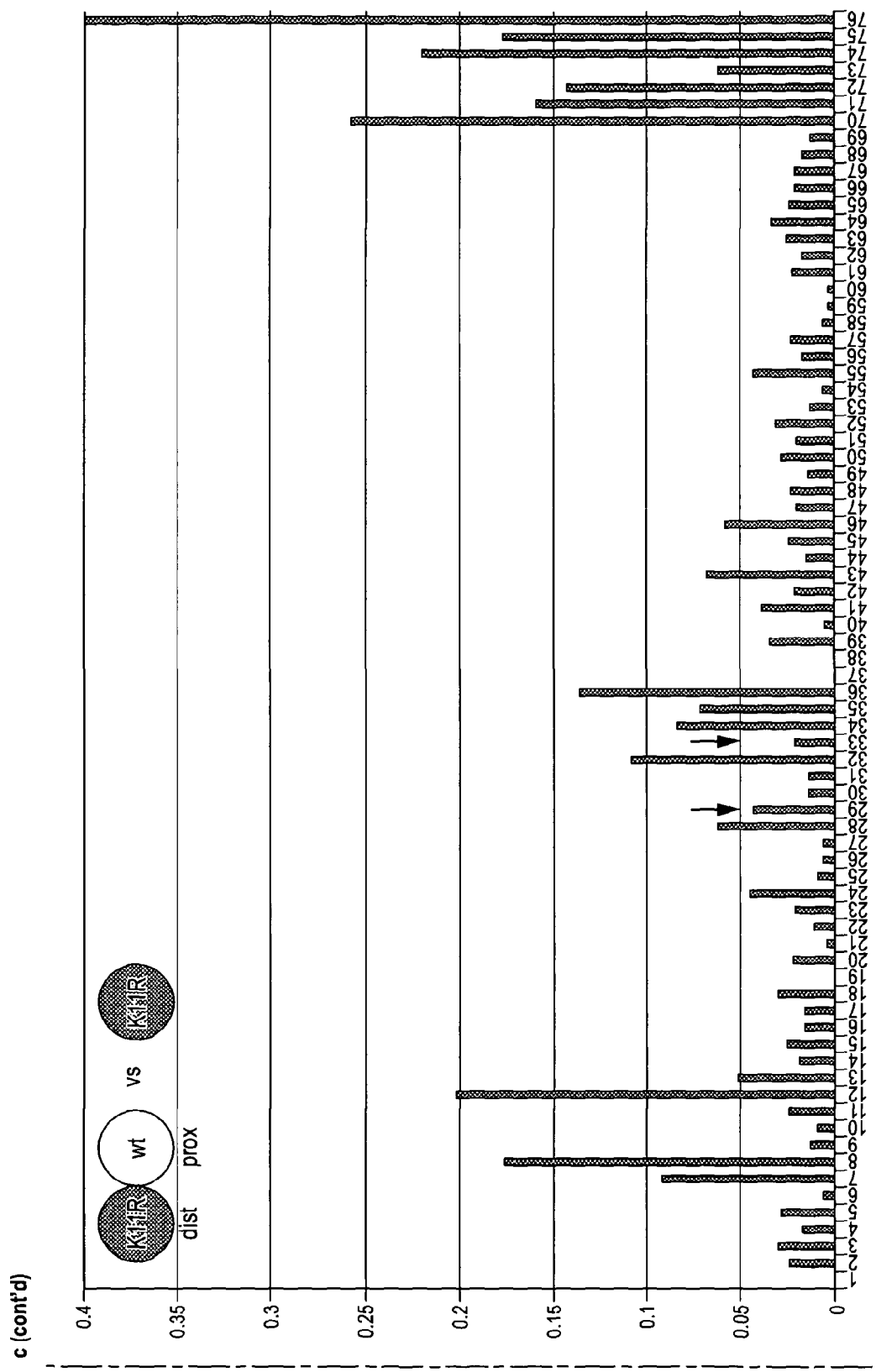
Figure 5:
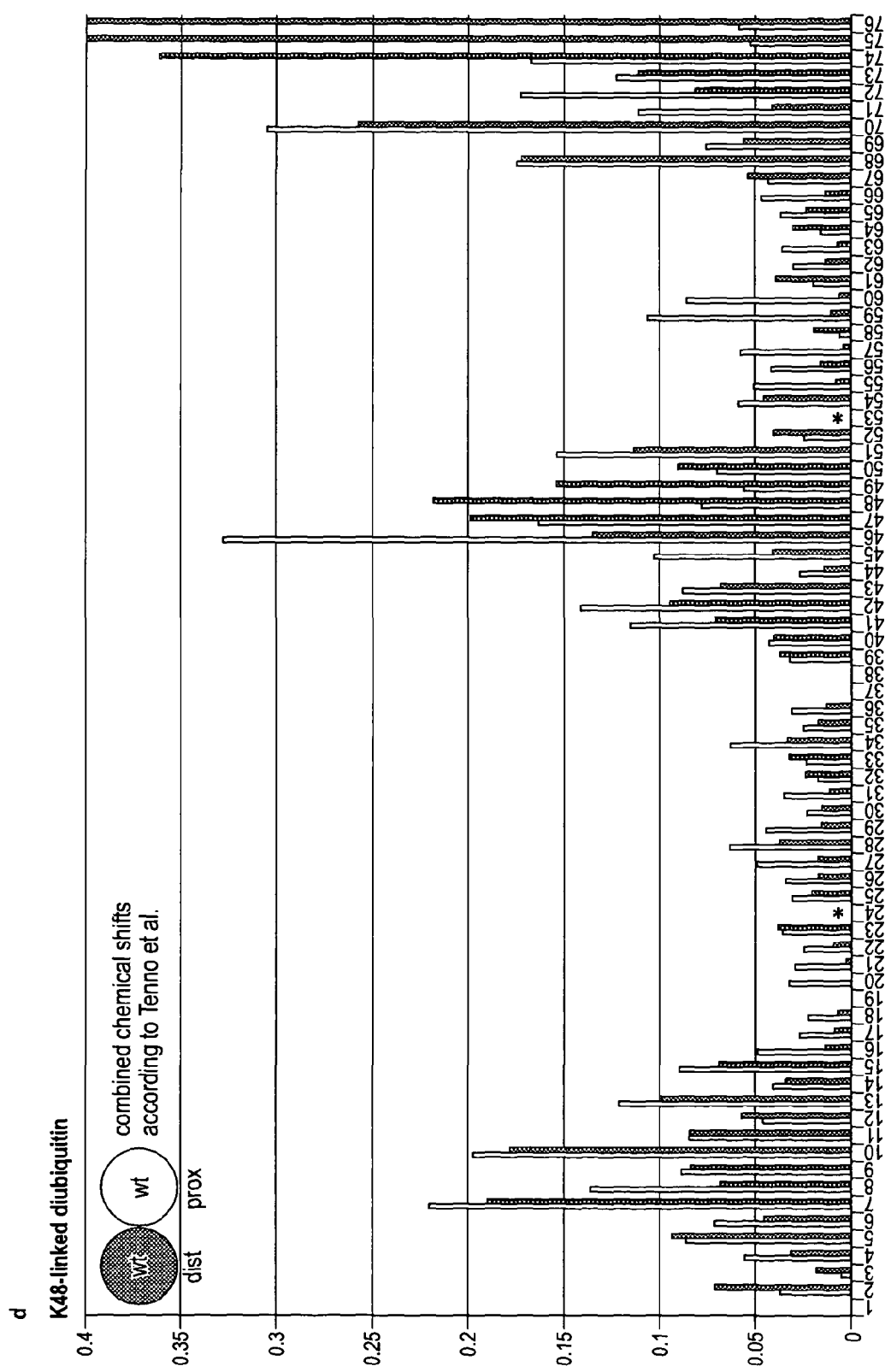
Figure 5:
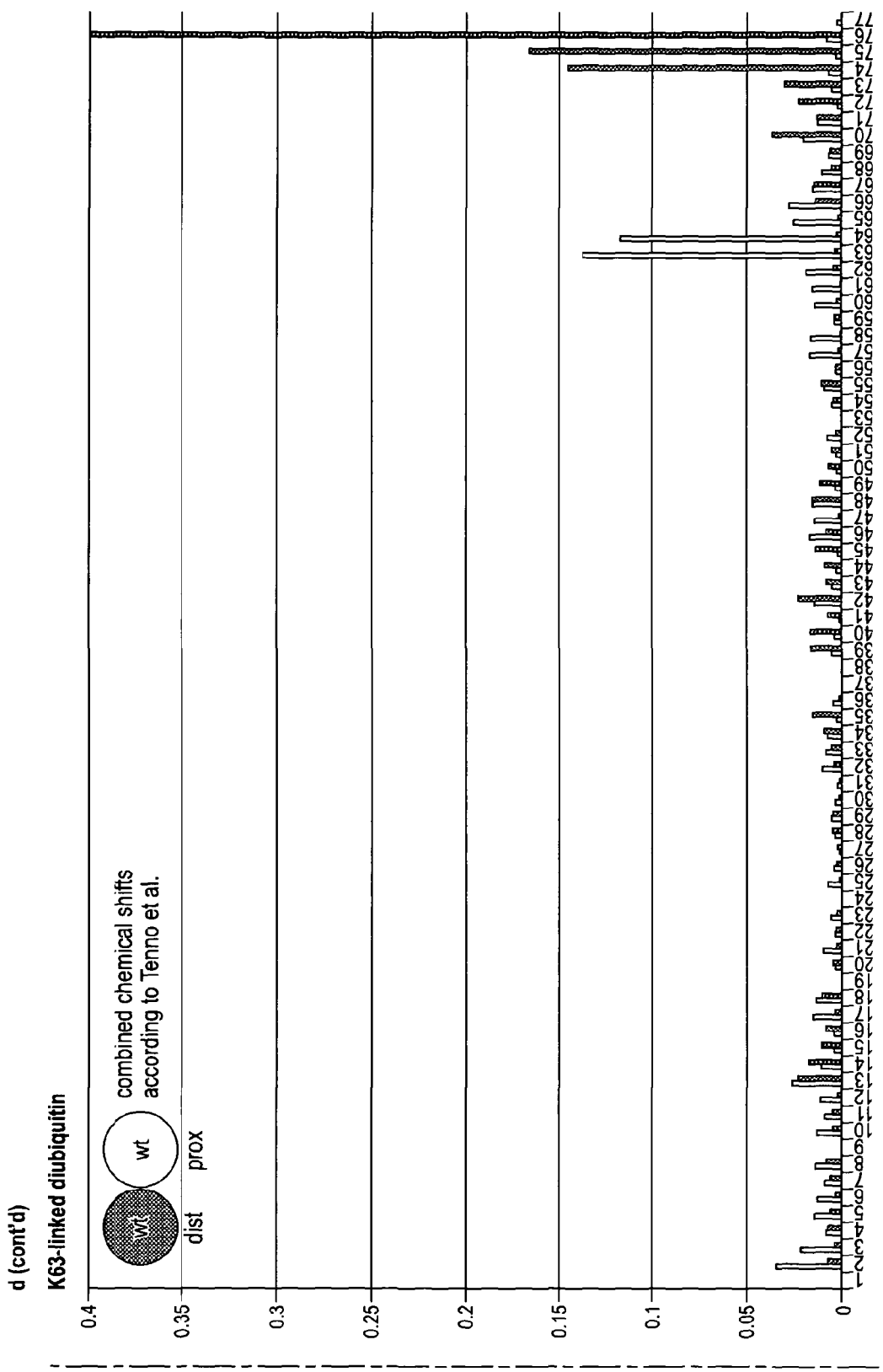

Diffraction data on crystals of KU-linked diubiquitin were collected on ESRF beamline ID14-EH2 (Grenoble). The crystals diffracted to a maximum resolution of 2.2 Å and displayed an orthorhombic space group that Pointless (Evans et al., 2006) identified to be most likely $P222_1$. The structure was solved by molecular replacement in MolRep (Vagin & Teplyakov, 2000), which identified 12 ubiquitin molecules from using monoubiquitin as a search model. The 12 molecules were related by translational symmetry, and formed two equivalent tetraubiquitin complexes with linkage ambiguity (FIG. 5), and another two diubiquitin molecules in which a two-fold axis generated the remaining dimers to form similar tetrameric assemblies. The structure was built in coot (Emsley & Cowtan, 2004) from the molecular replacement model, and refined in Phenix (Adams et al., 2002) using NCS, simulated annealing (initially) and TLS B-factor refinement at later stages of the refinement. Restraints for the isopeptide linkage were generated using phenix.elbow. Data collection and refinement statistics may be found in Table 2.

TABLE 2

Data collection and refinement statistics

| | K11-linked diubiquitin |
|---|---|
| Data collection | |
| Space group | $P222_1$ |
| Cell dimansions | |
| a, b, c (Å) | 79.23, 79.96, 231.23 |
| abg(°) | 90, 90, 90 |
| Resolution (Å) | 24.92-2.20 (2.32-2.20)* |
| $R_{sym}$ or $R_{merge}$ | 0.108 (0.485) |
| I/sI | 6.0 (2.0) |
| Completeness (%) | 98.3 (99.7) |
| Redundancy | 3.1 (3.0) |
| Refinement | |
| Resolution (Å) | 24.92-2.20 |
| No. reflections | 65088 |
| $R_{work}/R_{see}$ | 0.205/0.252 |
| No. atoms | |
| Protein | 7256 (12 ubiquitin molecules) |
| Ligand/ion | 111 |
| Water | 654 |
| B-factors | |
| Protein | 30.1 |
| Ligand/ion | 41.8 |
| Water | 34.4 |
| R.m.s. deviations | |
| Bond lengths (Å) | 0.005 |
| Bond angles (°) | 0.978 |

*Values in parentheses are for highest-resolution shelf.

Figure 4:
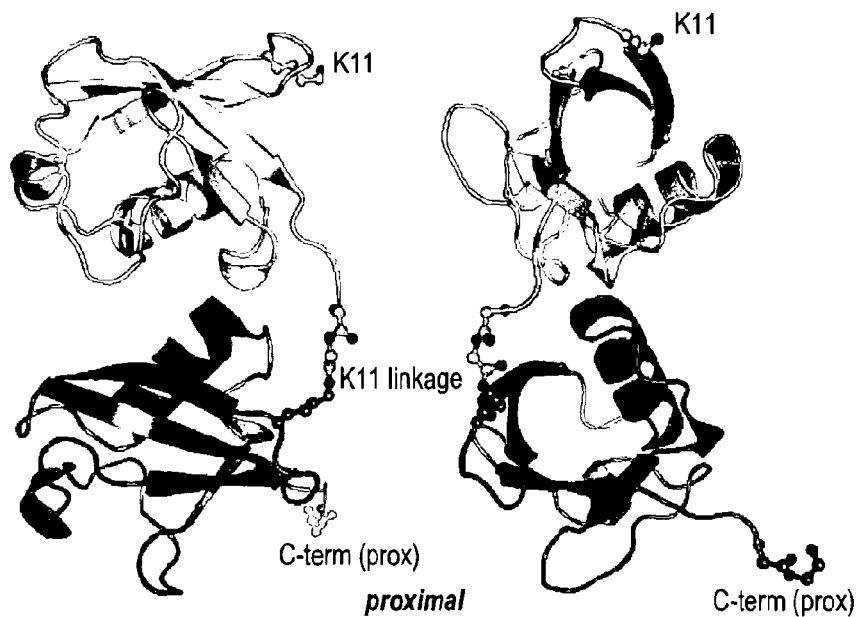
FIG. 4: Crystal structure of K11-linked diubiquitin. (a) The crystal structure of K11-linked diubiquitin in two orientations. The proximal (orange) and distal (yellow) molecules interact through the ubiquitin helix, and the isopeptide linkage (shown in ball-and-stick representation, with red oxygen and blue nitrogen atoms) is at the surface of the dimer. (b) A semitransparent surface coloured blue for residues Ile44, Leu8 and Val70 shows that the hydrophobic patch is not involved in the interface. (c) Residues at the interface are shown in stick representation, and polar interactions of <3.5 Å are shown with dotted lines. Water molecules are shown as purple spheres. (d) The hydrophobic surface in K11-linked chains is extended by Leu71 and Leu73, which are exposed as Arg72/Arg74 participate in the interface.
Figure 4:
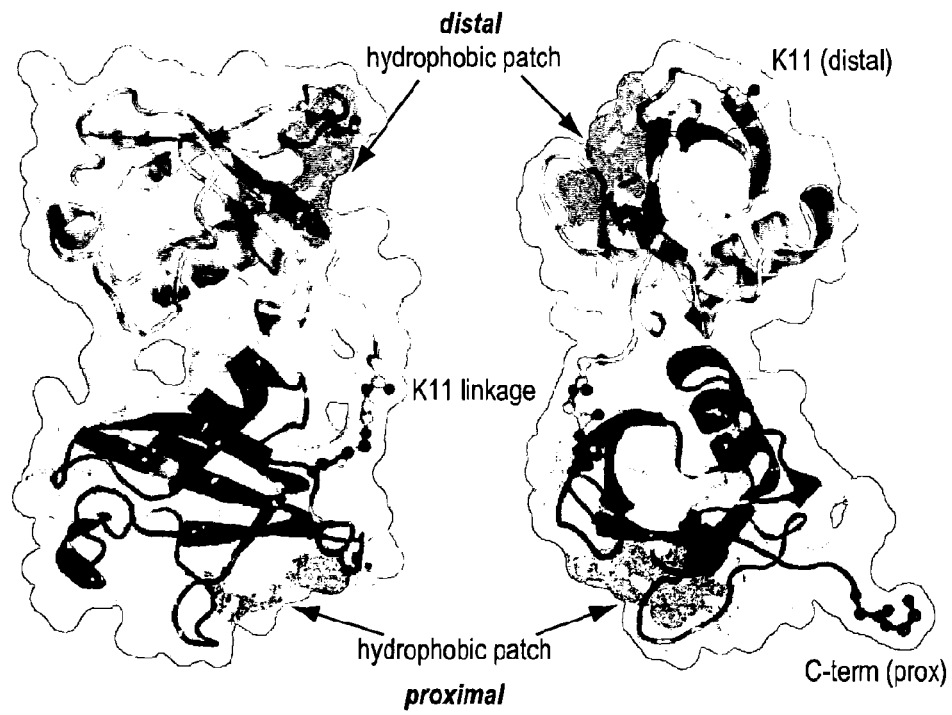
Figure 4:
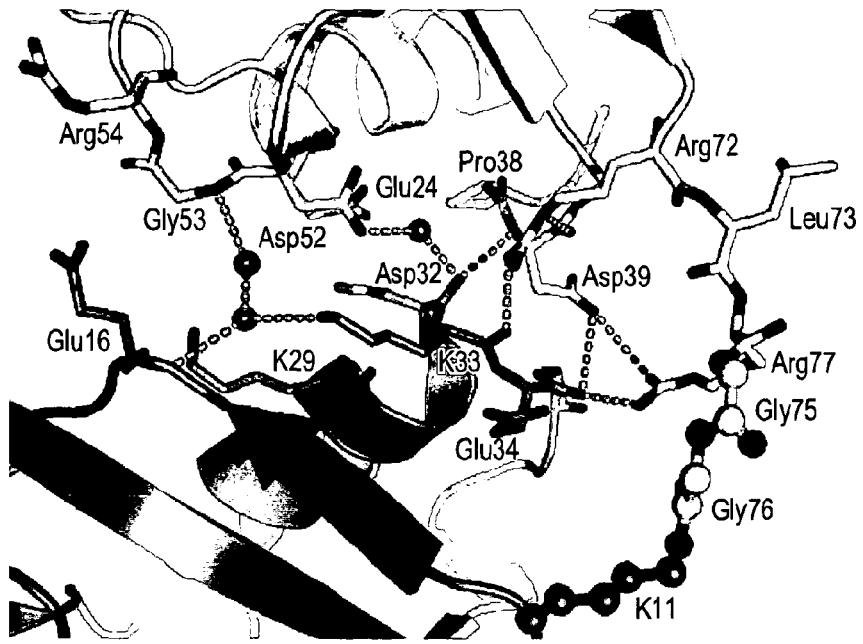
Figure 4:
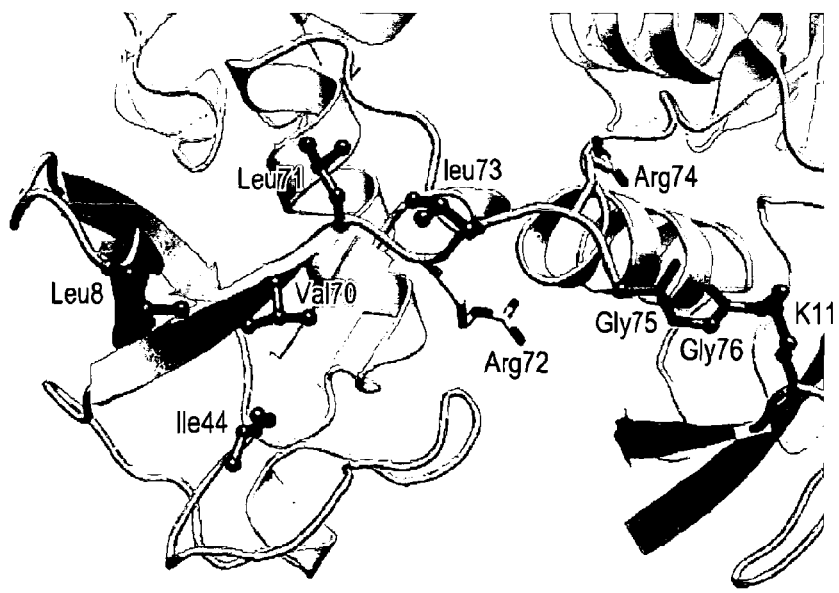

K11-linked diubiquitin adopts a compact conformation distinct from any other ubiquitin chain structure observed to date (FIG. 4a). Contacts between ubiquitin moieties are entirely polar and do not involve the hydrophobic ubiquitin surface patch (Ile44, Leu8, Val70), which is the most common ubiquitin interaction site (FIG. 4b). The interface instead forms between a surface centered on Glu24 of the distal ubiquitin, and a surface around Lys29 and Lys33 of the proximal ubiquitin. Several direct and water-mediated interactions are formed, including $Arg74^{dist}$-$Glu34^{prox, \, backbone \, (bb)}$, $Arg72^{dist}$-$Glu34^{prox, \, bb}$, $Asp39^{dist, \, bb}$-$Asp32^{prox, \, bb}$ (FIG. 4c). The crystal structure was obtained at pH 3.5 in presence of 3 M sodium chloride. These conditions may mask additional charged interactions, for example $Lys33^{prox}$-$Asp52^{dist}$, which are in close proximity but do not seem to interact in any of the dimer interfaces.

A striking feature of the crystal structure is the exposed location of the ubiquitin hydrophobic patch (FIG. 4b). In the crystal, eight of the twelve hydrophobic patches are not involved in crystal contacts but point towards solvent channels. Furthermore, the hydrophobic patch is extended by Leu71 and Leu73 from the C-terminal tail of ubiquitin (FIG. 4d). Since Arg72 and Arg74 are integral residues of the polar K11-diubiquitin interface, Leu71/Leu73 point outwards and are restrained unlike in monoubiquitin where the C-terminal tail is more mobile. Leu71/Leu73 therefore effectively increase the hydrophobic Ile44-surface (FIG. 4c, d). With this larger hydrophobic patch, interaction of K11-linked chains with UBDs is likely to result in new interaction modes. In particular, proteins with tandem UBDs may be well suited to interact with adjacent hydrophobic patches in K11-linked polyubiquitin. Alternatively, novel classes of UBDs may recognize the unique structural features of K11-linked chains.

Ubiquitin chains are dynamic entities and may adopt multiple conformations in solution. The solution properties of K11-linked ubiquitin chains were studied with Nuclear Magnetic Resonance (NMR) spectroscopy.

$^{13}C$, $^{15}N$-labeled ubiquitin K63R or K11R mutant was expressed from a pET17b plasmid in Rosetta2 (DE3) pLacl cells. A 100 ml overnight culture grown in LB medium was pelleted and resuspended in modified K-MOPS minimal media (Neidhardt et al., 1974), lacking nitrogen and carbon sources. This was used to inoculate 3 L modified K-MOPS media supplemented with $^{13}C$ glucose/$^{15}N$ ammonium chloride. Protein expression was induced after 16 hrs growth at 30° C. with 0.4 mM IPTG, and cells were harvested after a further 4 hrs. Mutant ubiquitin was purified according to Pickart & Rassi, 2005. To obtain only distally labeled K11-linked diubiquitin, wild-type ubiquitin was mixed with $^{13}C$, $^{15}N$-labeled ubiquitin K11R mutant in a 1:2 ration in a chain assembly reaction. Prior to data acquisition, samples were dialyzed either against phosphate buffered saline (150 mM NaCl, 18 mM $Na_2HPO_4$, 7 mM $NaH_2PO_4 \times 2H_2O$, pH 7.4) or against 150 mM NaCl, 50 mM $NH_4Ac$ (pH 3.5) in 3 kDa cut-off Slide-A-Lyzer dialysis cassettes (Thermo Scientific).

NMR experiments were acquired on Bruker DRX600 MHz and AV2+ 700 MHz spectrometers equipped with cryogenic triple resonance TCI probes and at a temperature of 298K; all data were processed in Topspin 2.1 (Bruker, Karlsruhe) and analyzed in Sparky (Goddard & Kneller, UCSF). Weighted chemical shift perturbations were measured in $^{15}N$ fast HSQC experiments (Mori et al., 1995) and defined as $((D^1H)^2)^{0.5}+((D^{15}N/5)^2)^{0.5}$ [ppm] (Hadjuk et al., 1997). Standard triple resonance experiments (HNCACB, CBCA(CO)NH and HNCA) were used to assign all mono- and di-ubiquitin K63R or K11R species and confirm the identity of shifted and doubled resonances.

$^1H$, $^{15}N$-heteronuclear correlation spectra (HSQC) provide a fingerprint of the local environment of individual residues. These so-called chemical shifts report on the resonance frequencies of all backbone amide protons and nitrogens, and chemical shift perturbations as a consequence of e.g. the formation of an interface are highly specific.

Applicants assembled uniformly labeled K11 diubiquitin from $^{13}$C, $^{15}$N-labeled K63R mutant ubiquitin. To subsequently deconvolute the contribution from both parts of the interface, in a second species only the distal moiety of K11-linked diubiquitin was $^{13}$C, $^{15}$N-labeled. To achieve this, assembly reactions with $^{13}$C, $^{15}$N-labeled K11R and unlabeled wild-type ubiquitin were performed, in which the K11R mutant serves as a distal chain terminator. To minimize buffer effects, the two labelled diubiquitin species, as well as labelled K63R, and K11R monoubiquitin (all at 100 μM) were dialyzed simultaneously against neutral (pH 7.4) or acidic (pH 3.5) buffer also containing 150 mM NaCl to mask nonspecific interactions. Relaxation experiments and measurements at different concentrations confirmed monodispersity, and allowed to exclude aggregation effects for all species at the chosen experimental conditions. Applicants assigned and confirmed the chemical shift positions in all species with standard tripleresonance experiments (Supp. FIG. 4a). To generate chemical shift perturbation maps, Applicants compared uniformly labeled K11-linked diubiquitin to K63R monoubiquitin, and distally labeled K11-linked diubiquitin to K11R monoubiquitin. To assess the effect of K63R and K11R mutations Applicants compared the labeled monoubiquitin species to find perturbation differences of <0.1 ppm, with exception of the flexible loop region in ubiquitin near K11 that is slightly more perturbed.

Immediately apparent was the doubling of a defined subset of resonances in the spectra of uniformly labeled K11-linked diubiquitin, associated with the formation of a non-symmetric interface (FIG. 5a). As expected, the resonances for Lys11 and Gly76 involved in the K11-linkage were significantly shifted compared to monoubiquitin (FIG. 5b). The chemical shift perturbation map of this species contains contributions of both sides of the interface (FIG. 5b). To deconvolute the individual contributions, Applicants analyzed chemical shift perturbations of distally labeled K11-linked diubiquitin in comparison to K11R monoubiquitin (FIG. 5b). This revealed the set of perturbed resonances that correspond to the interface on the distal moiety. Importantly, all resonances that were found to be perturbed in the distally labelled K11-linked diubiquitin have equivalent or similar perturbations in the uniformly labelled K11-linked diubiquitin. However, Applicants cannot exclude or quantify contributions to these perturbations from the proximal moiety in this case.

This analysis shows that K11-linked dimers have a defined pattern of perturbed resonances in solution, which is distinct from the pattern observed for K48-, or K63-linked diubiquitin (Varadan et al., 2004; Varadan et al., 2002; Tenno et al., 2004; FIG. 5d), reflecting (a) unique conformation(s) of KU-linked diubiquitin. Consistent with the crystallographic analysis, the backbone resonances corresponding to residues 41-51 of ubiquitin (including Ile44) are not perturbed, suggesting that this region which is involved in the K48 diubiquitin interface (Varadan et al., 2002; Tenno et al., 2004; FIG. 5d) and in most ubiquitin-UBD interactions (Zhang et al., 2009; Varadan et al., 2005; Raasi et al, 2005), is not involved in the dimer interface in K11-linkages. Instead, the chemical shift perturbations indicate three regions of the ubiquitin surface that contribute to the interface and/or are affected by the K11 isopeptide bond: The flexible β-hairpin loop spanning residues 5-15, possibly as a consequence of the isopeptide bond at K11; residues 29-36 that include the C-terminal part of the ubiquitin helix; and the C-terminal residues from 69-76 (FIG. 5b). Mapping of these residues onto the surface of ubiquitin reveals that the perturbed resonances correspond to a surface that is almost identical to the proximal interaction interface observed in the crystal structure (FIG. 5e). A corresponding distal interface however appears to be more distinct when compared to the crystal structure (FIG. 5f). At this interface, two residues, Gly53 and Asp24, remain exchange broadened as in monomeric ubiquitin (white in FIG. 5f), indicating that this region of the interface is dynamic and may adopt multiple conformations. Similar observations of exchange broadening in interface residues have been made in the case of K48-linked diubiquitin molecules (Varadan et al., 2002). However, two further residues that reside on the distal interface of the crystal structure, Asp39 and 10 Asp52 are also unperturbed (circled in FIG. 5f), indicating that in solution, the distal ubiquitin may rotate or move slightly, adjusting the interface.

To further distinguish between interface residues and residues perturbed as a result of forming the isopeptide linkage, Applicants analyzed chemical shift perturbations also at low pH. It has previously been shown for K48-linked diubiquitin that low pH 'opens' the compact conformation of this chain type resulting in a more transient interface21. If a similar interface 'opening' also occurred for KU-linkages, this may allow to define interface residues more confidently. Although at pH 3.5 Applicants observe fewer perturbations compared to pH 7.4, several residues remain perturbed (FIG. 5c). On the other hand, K29 and K33 are perturbed only at pH 7.4 but do not show significant perturbation at pH 3.5 (indicated by arrows in FIG. 5b,c). This suggests that these residues are located at an interface at pH 7.4.

In summary, the crystal structure represents most likely a more compact conformation compared to the conformation(s) of K11-linked diubiquitin in solution. However, solution studies also reveal significant perturbations indicative of an interface and hence a compact conformation of K11-linked diubiquitin. The distinct perturbation pattern suggests that K29 and K33 reside at the diubiquitin interface, which would result in a unique conformation compared to K48- and K63-linked diubiquitin. The data also highlight the dynamic nature of KU-linked ubiquitin chains. Further analysis will be required to analyze preferred domain orientations in K11-linked ubiquitin chains in solution. Taken together, the unique structural features of K11-linked diubiquitin highlight the conformational variability of differently linked ubiquitin chains (FIG. 5b,d).

REFERENCES

Komander, D. The emerging complexity of protein ubiquitination. *Biochem Soc Trans* 37, 937-53 (2009).

Chen, Z. J. & Sun, L. J. Nonproteolytic functions of ubiquitin in cell signaling. *Mol Cell* 33, 275-86 (2009).

Hershko, A. & Ciechanover, A. The ubiquitin system. *Annu Rev Biochem* 67, 425-79 (1998).

Xu, P. et al. Quantitative proteomics reveals the function of unconventional ubiquitin chains in proteasomal degradation. *Cell* 137, 133-45 (2009).

Peng, J. et al. A proteomics approach to understanding protein ubiquitination. *Nat Biotechnol* 21, 921-6 (2003).

Dye, B. T. & Schulman, B. A. Structural mechanisms underlying posttranslational modification by ubiquitin-like proteins. *Annu Rev Biophys Biomol Struct* 36, 131-50 (2007).

Ye, Y. & Rape, M. Building ubiquitin chains: E2 enzymes at work. *Nat Rev Mol Cell Biol* 10, 755-64 (2009).

Hofmann, R. M. & Pickart, C. M. Noncanonical MMS2-encoded ubiquitin-conjugating enzyme functions in assembly of novel polyubiquitin chains for DNA repair. *Cell* 96, 645-53 (1999).

Chen, Z. & Pickart, C. M. A 25-kilodalton ubiquitin carrier protein (E2) catalyzes multi-ubiquitin chain synthesis via lysine 48 of ubiquitin. *J Biol Chem* 265, 21835-42 (1990).

Baboshina, O. V. & Haas, A. L. Novel multiubiquitin chain linkages catalyzed by the conjugating enzymes E2EPF and RAD6 are recognized by 26 S proteasome subunit 5. *J Biol Chem* 271, 2823-31 (1996).

Jin, L., Williamson, A., Banerjee, s., Philipp, I. & Rape, M. Mechanism of ubiquitin-chain formation by the human anaphase-promoting complex. *Cell* 133, 653-65 (2008).

Alexandru, G. et al. UBXD7 binds multiple ubiquitin ligases and implicates p97 in HIF1alpha turnover. *Cell* 134, 804-16 (2008).

Reyes-Turcu, F. E. et al. The ubiquitin binding domain ZnF UBP recognizes the C-terminal diglycine motif of unanchored ubiquitin. *Cell* 124, 1197-208 (2006).

McCullough, J., Clague, M. J. & Urbe, S. AMSH is an endosome-associated ubiquitin isopeptidase. *J Cell Biol* 166, 487-92 (2004).

Varadan, R. et al. Solution conformation of Lys63-linked di-ubiquitin chain provides clues to functional diversity of polyubiquitin signaling. *J Biol Chem* 279, 7055-63 (2004).

Varadan, R., Walker, O., Pickart, C. & Fushman, D. Structural properties of polyubiquitin chains in solution. *J Mol Biol* 324, 637-47 (2002).

Tenno, T. et al. Structural basis for distinct roles of Lys63- and Lys48-linked polyubiquitin chains. *Genes Cells* 9, 865-75 (2004).

Zhang, N. et al. Structure of the s5a:k48-linked diubiquitin complex and its interactions with rpn13. *Mol Cell* 35, 280-90 (2009).

Varadan, R., Assfalg, M., Raasi, S., Pickart, C. & Fushman, D. Structural determinants for selective recognition of a Lys48-linked polyubiquitin chain by a UBA domain. *Mol Cell* 18, 687-98 (2005).

Raasi, S., Varadan, R., Fushman, D. & Pickart, C. M. Diverse polyubiquitin interaction properties of ubiquitin-associated domains. *Nat Struct Mol Biol* 12, 708-14 (2005).

Evans, P. Scaling and assessment of data quality. *Acta Crystalogr D Biol Crystallogr* 62, 72-82 (2006).

Vagin, A. & Teplyakov, A. An approach to multi-copy search in molecular replacement. *Acta Crystallogr D Biol Crystallogr* 56, 1622-4 (2000).

Emsley, P. & Cowtan, K. Coot: model-building tools for molecular graphics. *Acta Crystallogr D Biol Crystallogr* 60, 2126-32 (2004).

Adams, P. D. et al. PHENIX: building new software for automated crystallographic structure determination. *Acta Crystallogr D Biol Crystallogr* 58, 1948-54 (2002).

Neidhardt, F. C., Bloch, P. L. □ & Smith, D. F. Culture medium for enterobacteria. *J Bacteriol* 119, 736-47 (1974).

Pickart, C. M. & Raasi, S. Controlled synthesis of polyubiquitin chains. *Methods Enzymol* 399, 21-36 (2005).

Mori, S., Abeygunawardana, C., Johnson, M. O. & van Zijl, P. C. Improved sensitivity of HSQC spectra of exchanging protons at short interscan delays using a new fast HSQC (FHSQC) detection scheme that avoids water saturation. *J Magn Reson B* 108, 94-8 (1995).

Hajduk, P. J. et al. NMR-based discovery of lead inhibitors that block DNA binding of the human papillomavirus E2 protein. *J Med Chem* 40, 3144-50 (1997).

Dikic, et al., Ubiquitin-binding domains—from structures to functions. *Nat Rev Mol Biol* 10:659-671, 2009

Hicke et al., *Nat Rev Cell Biol* 6:610-621, 2005

The invention is further described by the following numbered paragraphs:

1. An E2 enzyme comprising a Ubc domain, from which an N-terminal tail or a C-terminal tail has been removed.

2. An E2 enzyme according to paragraph 1, which is a chimeric enzyme wherein the Ubc is fused to a heterologous ubiquitin-binding domain (UBD).

3. A chimeric E2 enzyme according to paragraph 2, wherein the UBD is C-terminal to the Ubc domain.

4. A chimeric E2 enzyme according to paragraph 2 or paragraph 3, wherein the UBD is an α-helical, zinc finger or pleckstrin homology domain.

5. A chimeric E2 enzyme according to paragraph 2 or paragraph 3, wherein the UBD is a domain selected from the group consisting of UIM, IUIM (MIU), DUIM, UBM, UBA, GAT, CUE, VHS, UBZ, NZF, ZnF A20, ZnF UBP (PAZ), PRU, GLUE, UEV, UBC, SH3, PFU and Jab1/MNP domains.

6. A chimeric E2 enzyme according to paragraph 4 or paragraph 5, wherein the UBD is derived from Isopeptidase T.

7. A chimeric E2 enzyme according to paragraph 6, wherein the UBD comprises the sequence from about position 163 to about position 291 of Isopeptidase T.

8. A chimeric E2 enzyme according to paragraph 4 or paragraph 5, wherein the UBD is a UBA, UIM, ZnF or NZF domain.

9. An E2 enzyme according to any preceding paragraph, wherein the Ubc domain is derived from an E2 enzyme selected from the group consisting of UBE2A, UBE2B, UBE2C, UBE2D1, UBE2D2, UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2NL, UBE2O, UBE2Q1, UBE2Q2, UBE2R1, UBE2R2, UBE2S, UBE2T, UBE2U, UBE2W, UBE2Z and BIRC6.

10. An E2 enzyme according to paragraph 9, wherein the E2 enzyme is a class II E2 enzyme.

11. An E2 enzyme according to paragraph 10, wherein an N-terminal or a C-terminal amino acid tail on the class II E2 enzyme is replaced by the UBD.

12. An E2 enzyme according to paragraph 10 or paragraph 11, wherein the Ubc domain is derived from UBE2S.

13. An E2 enzyme according to paragraph 12, wherein the Ubc domain comprises residues 1 to 156 of UBE2S.

14. A method for increasing the capacity of an E2 enzyme to produce free polyubiquitin chains in solution, comprising conjugating fusing the Ubc domain of said E2 enzyme to a UBD.

15. A method according to paragraph 14, wherein the E2 enzyme is selected from the group consisting of UBE2A, UBE2B, UBE2C, UBE2D1, UBE2D2, UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2NL, UBE2O, UBE2Q1, UBE2Q2, UBE2R1, UBE2R2, UBE2S, UBE2T, UBE2U, UBE2V1, UBE2V2, UBE2V3, UBE2W, UBE2Z, AKTIP and BIRC6 and the UBD is a domain selected from the group consisting of UIM, IUIM (MIU), DUIM, UBM, UBA, GAT, CUE, VHS, UBZ, NZF, A20-like ZnF, ZnF UBP (PAZ), PRU, GLUE, UEV, UBC, SH3, PFU and Jab1/MNP domains.

16. A method according to paragraph 15, wherein the E2 enzyme is UBE2S.

17. A method according to any one of paragraphs 14 to 16, wherein the UBD is a ZnF UBP domain.

18. A method for producing free polyubiquitin chains linked through a desired lysine residue, comprising the steps of: (a) selecting an E2 enzyme which possesses the desired lysine residue specificity; (b) fusing the Ubc catalytic domain of said E2 enzyme to a UBD ubiquitin binding domain; and incubating the resulting chimeric protein with an E1 ubiquitin activating enzyme and monomeric ubiquitin.

19. A method according to paragraph 18, wherein the incidence of undesired lysine linkages is reduced by including a linkage-specific deubiquitinase in the incubation.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A chimeric enzyme comprising a UBE2S ubiquitin conjugating enzyme (E2) having a ubiquitin conjugating (Ubc) domain, from which an N-terminal tail or a C-terminal tail has been removed, fused to a heterologous ubiquitin-binding domain (UBD).

2. A chimeric enzyme according to claim 1, comprising a UBE2S E2 enzyme having a Ubc domain, from which an N-terminal tail or a C-terminal tail has been removed, fused to a heterologous Isopeptidase T ubiquitin-binding domain (UBD).

3. A chimeric enzyme according to claim 1, wherein the UBD is C-terminal to the Ubc domain.

4. A chimeric enzyme according to claim 1, wherein the UBD is an α-helical, zinc finger or pleckstrin homology domain.

5. A chimeric enzyme according to claim 1, wherein the UBD is a domain selected from the group consisting of ubiquitin interacting motifs (UIM, MIU, dUIM), alpha-helical domains (UBA), entoplasmic reticulum targeting domains (CUE), VHS, polymerase-h or polymerase-k domains (UBZ), zinc finger (ZnF) domains (NZF, PAZ, A20, UBP), pleckstrin homology domains (UEV), and UBC domains.

6. A chimeric enzyme according to claim 2, wherein the UBD is C-terminal to the Ubc domain.

7. A chimeric enzyme according to claim 2, wherein the UBD comprises the zinc finger (ZnF UBP or PAZ) domain of Isopeptidase T.

8. A chimeric enzyme according to claim 5, wherein the UBD is a UBA, UIM, ZnF or NZF domain.

9. A chimeric enzyme according to claim 1, wherein an N-terminal or a C-terminal amino acid tail on the E2 enzyme is replaced by the UBD.

10. A chimeric enzyme according to claim 2, wherein an N-terminal or a C-terminal amino acid tail on the E2 enzyme is replaced by the UBD.

11. A chimeric enzyme according to claim 1 or 2, wherein the UBE2S E2 enzyme has the C-terminal extension residues thereof removed or replaced with the UBD.

12. A method for increasing the capacity of an E2 enzyme to produce free polyubiquitin chains in solution, comprising the chimeric enzyme of claim 1.

13. A method according to claim 12, comprising fusing a UBE2S E2 enzyme having a Ubc domain, from which an N-terminal tail or a C-terminal tail has been removed, to a heterologous Isopeptidase T ubiquitin-binding domain (UBD).

14. A method according to claim 12, wherein the UBD is a domain selected from the group consisting of ubiquitin interacting motifs (UIM, MIU, dUIM), alpha-helical domains (UBA), entoplasmic reticulum targeting domains (CUE), VHS, polymerase-h or polymerase-k domains (UBZ), zinc finger (ZnF) domains (NZF, PAZ, A20, UBP), pleckstrin homology domains (UEV), and UBC domains.

15. A method according to claim 13, wherein the UBD is a zinc finger (ZnF UBP or PAZ) domain of Isopeptidase T.

16. A method for producing free polyubiquitin chains linked through a desired lysine residue, comprising fusing a UBE2S ubiquitin conjugating enzyme (E2) having a ubiquitin conjugating (Ubc) domain, from which an N-terminal tail or a C-terminal tail has been removed to a heterologous ubiquitin-binding domain (UBD); and incubating the resulting chimeric protein with an E1 ubiquitin activating enzyme and monomeric ubiquitin.

17. A method according to claim 16 for producing free polyubiquitin chains linked through a desired lysine residue, comprising fusing a UBE2S E2 enzyme having a Ubc domain, from which an N-terminal tail or G-terminal tail has been removed to a heterologous Isopeptidase T ubiquitin-binding domain (UBD); and incubating the resulting chimeric protein with an E1 ubiquitin activating enzyme and monomeric ubiquitin.

18. A method according to claim 16 or 17, wherein the incidence of undesired lysine linkages is reduced by including a linkage-specific deubiquitinase in the incubation.

* * * * *

SEQUENCE LISTING

```
<160> NUMBER OF SEQ ID NOS: 38

<210> SEQ ID NO 1
<211> LENGTH: 179
<212> TYPE: PRT
<213> ORGANISM: Homo sapiens

<400> SEQUENCE: 1

Met Ala Ser Gln Asn Arg Asp Pro Ala Ala Thr Ser Val Ala Ala Ala
1               5                   10                  15

Arg Lys Gly Ala Glu Pro Ser Gly Gly Ala Ala Arg Gly Pro Val Gly
            20                  25                  30

Lys Arg Leu Gln Gln Glu Leu Met Thr Leu Met Met Ser Gly Asp Lys
        35                  40                  45

Gly Ile Ser Ala Phe Pro Glu Ser Asp Asn Leu Phe Lys Trp Val Gly
    50                  55                  60

Thr Ile His Gly Ala Ala Gly Thr Val Tyr Glu Asp Leu Arg Tyr Lys
65                  70                  75                  80

Leu Ser Leu Glu Phe Pro Ser Gly Tyr Pro Tyr Asn Ala Pro Thr Val
                85                  90                  95

Lys Phe Leu Thr Pro Cys Tyr His Pro Asn Val Asp Thr Gln Gly Asn
            100                 105                 110

Ile Cys Leu Asp Ile Leu Lys Glu Lys Trp Ser Ala Leu Tyr Asp Val
        115                 120                 125

Arg Thr Ile Leu Leu Ser Ile Gln Ser Leu Leu Gly Glu Pro Asn Ile
    130                 135                 140

Asp Ser Pro Leu Asn Thr His Ala Ala Glu Leu Trp Lys Asn Pro Thr
145                 150                 155                 160

Ala Phe Lys Lys Tyr Leu Gln Glu Thr Tyr Ser Lys Gln Val Thr Ser
                165                 170                 175

Gln Glu Pro

<210> SEQ ID NO 2
<211> LENGTH: 147
<212> TYPE: PRT
<213> ORGANISM: Homo sapiens

<400> SEQUENCE: 2

Met Ala Leu Lys Arg Ile Gln Lys Glu Leu Ser Asp Leu Gln Arg Asp
1               5                   10                  15

Pro Pro Ala His Cys Ser Ala Gly Pro Val Gly Asp Asp Leu Phe His
            20                  25                  30

Trp Gln Ala Thr Ile Met Gly Pro Pro Asp Ser Ala Tyr Gln Gly Gly
        35                  40                  45
```

Val Phe Phe Leu Thr Val His Phe Pro Thr Asp Tyr Pro Phe Lys Pro
    50                  55                  60

Pro Lys Ile Ala Phe Thr Thr Lys Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Val Ser Lys Val Leu Leu Ser Ile Cys Ser Leu Leu Cys Asp
            100                 105                 110

Pro Asn Pro Asp Asp Pro Leu Val Pro Asp Ile Ala Gln Ile Tyr Lys
            115                 120                 125

Ser Asp Lys Glu Lys Tyr Asn Arg His Ala Arg Glu Trp Thr Gln Lys
130                 135                 140

Tyr Ala Met
145

<210> SEQ ID NO 3
<211> LENGTH: 118
<212> TYPE: PRT
<213> ORGANISM: Homo sapiens

<400> SEQUENCE: 3

Met Phe His Trp Gln Ala Thr Ile Met Gly Pro Asn Asp Ser Pro Tyr
1               5                   10                  15

Gln Gly Gly Val Phe Phe Leu Thr Ile His Phe Pro Thr Asp Tyr Pro
                20                  25                  30

Phe Lys Pro Pro Lys Val Ala Phe Thr Thr Arg Ile Tyr His Pro Asn
            35                  40                  45

Ile Asn Ser Asn Gly Ser Ile Cys Leu Asp Ile Leu Arg Ser Gln Trp
50                  55                  60

Ser Pro Ala Leu Thr Ile Ser Lys Val Leu Leu Ser Ile Cys Ser Leu
65                  70                  75                  80

Leu Cys Asp Pro Asn Pro Asp Asp Pro Leu Val Pro Glu Ile Ala Arg
                85                  90                  95

Ile Tyr Lys Thr Asp Arg Glu Lys Tyr Asn Arg Ile Ala Arg Glu Trp
            100                 105                 110

Thr Gln Lys Tyr Ala Met
            115

<210> SEQ ID NO 4
<211> LENGTH: 149
<212> TYPE: PRT
<213> ORGANISM: Homo sapiens

<400> SEQUENCE: 4

Met Leu Ser Asn Arg Lys Cys Leu Ser Lys Glu Leu Ser Asp Leu Ala
1               5                   10                  15

Arg Asp Pro Pro Ala Gln Cys Ser Ala Gly Pro Val Gly Asp Asp Met
                20                  25                  30

Phe His Trp Gln Ala Thr Ile Met Gly Pro Asn Asp Ser Pro Tyr Gln
            35                  40                  45

Gly Gly Val Phe Phe Leu Thr Ile His Phe Pro Thr Asp Tyr Pro Phe
50                  55                  60

Lys Pro Pro Lys Val Ala Phe Thr Thr Arg Ile Tyr His Pro Asn Ile
65                  70                  75                  80

Asn Ser Asn Gly Ser Ile Cys Leu Asp Ile Leu Arg Ser Gln Trp Ser
                85                  90                  95

```
Pro Ala Leu Thr Ile Ser Lys Val Leu Ser Ile Cys Ser Leu Leu
            100                 105                 110

Cys Asp Pro Asn Pro Asp Pro Leu Val Pro Glu Ile Ala Arg Ile
            115                 120                 125

Tyr Lys Thr Asp Arg Asp Lys Tyr Asn Arg Ile Ser Arg Glu Trp Thr
        130                 135                 140

Gln Lys Tyr Ala Met
145

<210> SEQ ID NO 5
<211> LENGTH: 201
<212> TYPE: PRT
<213> ORGANISM: Homo sapiens

<400> SEQUENCE: 5

Met Ser Thr Glu Ala Gln Arg Val Asp Asp Ser Pro Thr Ser Gly
1               5                   10                  15

Gly Ser Ser Asp Gly Asp Gln Arg Glu Ser Val Gln Gln Glu Pro Glu
            20                  25                  30

Arg Glu Gln Val Gln Pro Lys Lys Glu Gly Lys Ile Ser Ser Lys
        35                  40                  45

Thr Ala Ala Lys Leu Ser Thr Ser Ala Lys Arg Ile Gln Lys Glu Leu
50                  55                  60

Ala Glu Ile Thr Leu Asp Pro Pro Asn Cys Ser Ala Gly Pro Lys
65                  70                  75                  80

Gly Asp Asn Ile Tyr Glu Trp Arg Ser Thr Ile Leu Gly Pro Pro Gly
            85                  90                  95

Ser Val Tyr Glu Gly Gly Val Phe Phe Leu Asp Ile Thr Phe Ser Pro
            100                 105                 110

Asp Tyr Pro Phe Lys Pro Pro Lys Val Thr Phe Arg Thr Arg Ile Tyr
            115                 120                 125

His Cys Asn Ile Asn Ser Gln Gly Val Ile Cys Leu Asp Ile Leu Lys
            130                 135                 140

Asp Asn Trp Ser Pro Ala Leu Thr Ile Ser Lys Val Leu Leu Ser Ile
145                 150                 155                 160

Cys Ser Leu Leu Thr Asp Cys Asn Pro Ala Asp Pro Leu Val Gly Ser
            165                 170                 175

Ile Ala Thr Gln Tyr Met Thr Asn Arg Ala Glu His Asp Arg Met Ala
            180                 185                 190

Arg Gln Trp Thr Lys Arg Tyr Ala Thr
        195                 200

<210> SEQ ID NO 6
<211> LENGTH: 207
<212> TYPE: PRT
<213> ORGANISM: Homo sapiens

<400> SEQUENCE: 6

Met Ser Ser Asp Arg Gln Arg Ser Asp Asp Glu Ser Pro Ser Thr Ser
1               5                   10                  15

Ser Gly Ser Ser Asp Ala Asp Gln Arg Asp Pro Ala Ala Pro Glu Pro
            20                  25                  30

Glu Glu Gln Glu Glu Arg Lys Pro Ser Ala Thr Gln Gln Lys Lys Asn
        35                  40                  45

Thr Lys Leu Ser Ser Lys Thr Thr Ala Lys Leu Ser Thr Ser Ala Lys
50                  55                  60
```

Arg Ile Gln Lys Glu Leu Ala Glu Ile Thr Leu Asp Pro Pro Asn
65                  70                  75                  80

Cys Ser Ala Gly Pro Lys Gly Asp Asn Ile Tyr Glu Trp Arg Ser Thr
                85                  90                  95

Ile Leu Gly Pro Pro Gly Ser Val Tyr Glu Gly Gly Val Phe Phe Leu
            100                 105                 110

Asp Ile Thr Phe Ser Ser Asp Tyr Pro Phe Lys Pro Pro Lys Val Thr
            115                 120                 125

Phe Arg Thr Arg Ile Tyr His Cys Asn Ile Asn Ser Gln Gly Val Ile
130                 135                 140

Cys Leu Asp Ile Leu Lys Asp Asn Trp Ser Pro Ala Leu Thr Ile Ser
145                 150                 155                 160

Lys Val Leu Leu Ser Ile Cys Ser Leu Leu Thr Asp Cys Asn Pro Ala
                165                 170                 175

Asp Pro Leu Val Gly Ser Ile Ala Thr Gln Tyr Leu Thr Asn Arg Ala
            180                 185                 190

Glu His Asp Arg Ile Ala Arg Gln Trp Thr Lys Arg Tyr Ala Thr
            195                 200                 205

<210> SEQ ID NO 7
<211> LENGTH: 185
<212> TYPE: PRT
<213> ORGANISM: Homo sapiens

<400> SEQUENCE: 7

Met Leu Thr Leu Ala Ser Lys Leu Lys Arg Asp Asp Gly Leu Lys Gly
1               5                   10                  15

Ser Arg Thr Ala Ala Thr Ala Ser Asp Ser Thr Arg Arg Val Ser Val
                20                  25                  30

Arg Asp Lys Leu Leu Val Lys Glu Val Ala Glu Leu Glu Ala Asn Leu
            35                  40                  45

Pro Cys Thr Cys Lys Val His Phe Pro Asp Pro Asn Lys Leu His Cys
50                  55                  60

Phe Gln Leu Thr Val Thr Pro Asp Glu Gly Tyr Tyr Gln Gly Gly Lys
65                  70                  75                  80

Phe Gln Phe Glu Thr Glu Val Pro Asp Ala Tyr Asn Met Val Pro Pro
                85                  90                  95

Lys Val Lys Cys Leu Thr Lys Ile Trp His Pro Asn Ile Thr Glu Thr
            100                 105                 110

Gly Glu Ile Cys Leu Ser Leu Leu Arg Glu His Ser Ile Asp Gly Thr
            115                 120                 125

Gly Trp Ala Pro Thr Arg Thr Leu Lys Asp Val Val Trp Gly Leu Asn
130                 135                 140

Ser Leu Phe Thr Asp Leu Leu Asn Phe Asp Asp Pro Leu Asn Ile Glu
145                 150                 155                 160

Ala Ala Glu His His Leu Arg Asp Lys Glu Asp Phe Arg Asn Lys Val
                165                 170                 175

Asp Asp Tyr Ile Lys Arg Tyr Ala Arg
            180                 185

<210> SEQ ID NO 8
<211> LENGTH: 318
<212> TYPE: PRT
<213> ORGANISM: Homo sapiens

<400> SEQUENCE: 8

```
Met Glu Thr Arg Tyr Asn Leu Lys Ser Pro Ala Val Lys Arg Leu Met
1               5                   10                  15

Lys Glu Ala Ala Glu Leu Lys Asp Pro Thr Asp His Tyr His Ala Gln
            20                  25                  30

Pro Leu Glu Asp Asn Leu Phe Glu Trp His Phe Thr Val Arg Gly Pro
        35                  40                  45

Pro Asp Ser Asp Phe Asp Gly Val Tyr His Gly Arg Ile Val Leu
50                  55                  60

Pro Pro Glu Tyr Pro Met Lys Pro Pro Ser Ile Ile Leu Leu Thr Ala
65              70                  75                  80

Asn Gly Arg Phe Glu Val Gly Lys Lys Ile Cys Leu Ser Ile Ser Gly
                85                  90                  95

His His Pro Glu Thr Trp Gln Pro Ser Trp Ser Ile Arg Thr Ala Leu
            100                 105                 110

Leu Ala Ile Ile Gly Phe Met Pro Thr Lys Gly Glu Gly Ala Ile Gly
            115                 120                 125

Ser Leu Asp Tyr Thr Pro Glu Glu Arg Arg Ala Leu Ala Lys Lys Ser
            130                 135                 140

Gln Asp Phe Cys Cys Glu Gly Cys Gly Ser Ala Met Lys Asp Val Leu
145                 150                 155                 160

Leu Pro Leu Lys Ser Gly Ser Asp Ser Ser Gln Ala Asp Gln Glu Ala
                165                 170                 175

Lys Glu Leu Ala Arg Gln Ile Ser Phe Lys Ala Glu Val Asn Ser Ser
            180                 185                 190

Gly Lys Thr Ile Ser Glu Ser Asp Leu Asn His Ser Phe Ser Leu Thr
            195                 200                 205

Asp Leu Gln Asp Asp Ile Pro Thr Thr Phe Gln Gly Ala Thr Ala Ser
        210                 215                 220

Thr Ser Tyr Gly Leu Gln Asn Ser Ser Ala Ala Ser Phe His Gln Pro
225                 230                 235                 240

Thr Gln Pro Val Ala Lys Asn Thr Ser Met Ser Pro Arg Gln Arg Arg
                245                 250                 255

Ala Gln Gln Gln Ser Gln Arg Arg Leu Ser Thr Ser Pro Asp Val Ile
            260                 265                 270

Gln Gly His Gln Pro Arg Asp Asn His Thr Asp His Gly Gly Ser Ala
            275                 280                 285

Val Leu Ile Val Ile Leu Thr Leu Ala Leu Ala Ala Leu Ile Phe Arg
            290                 295                 300

Arg Ile Tyr Leu Ala Asn Glu Tyr Ile Phe Asp Phe Glu Leu
305                 310                 315

<210> SEQ ID NO 9
<211> LENGTH: 259
<212> TYPE: PRT
<213> ORGANISM: Homo sapiens

<400> SEQUENCE: 9

Met Ser Ser Thr Ser Ser Lys Arg Ala Pro Thr Thr Ala Thr Gln Arg
1               5                   10                  15

Leu Lys Gln Asp Tyr Leu Arg Ile Lys Lys Asp Pro Val Pro Tyr Ile
            20                  25                  30

Cys Ala Glu Pro Leu Pro Ser Asn Ile Leu Glu Trp His Tyr Val Val
        35                  40                  45

Arg Gly Pro Glu Met Thr Pro Tyr Glu Gly Gly Tyr Tyr His Gly Lys
50                  55                  60
```

-continued

```
Leu Ile Phe Pro Arg Glu Pro Phe Lys Pro Pro Ser Ile Tyr Met
 65                  70                  75                  80

Ile Thr Pro Asn Gly Arg Phe Lys Cys Asn Thr Arg Leu Cys Leu Ser
                 85                  90                  95

Ile Thr Asp Phe His Pro Asp Thr Trp Asn Pro Ala Trp Ser Val Ser
            100                 105                 110

Thr Ile Leu Thr Gly Leu Leu Ser Phe Met Val Glu Lys Gly Pro Thr
        115                 120                 125

Leu Gly Ser Ile Glu Thr Ser Asp Phe Thr Lys Arg Gln Leu Ala Val
    130                 135                 140

Gln Ser Leu Ala Phe Asn Leu Lys Asp Lys Val Phe Cys Glu Leu Phe
145                 150                 155                 160

Pro Glu Val Val Glu Glu Ile Lys Gln Lys Gln Lys Ala Gln Asp Glu
                165                 170                 175

Leu Ser Ser Arg Pro Gln Thr Leu Pro Leu Pro Asp Val Val Pro Asp
            180                 185                 190

Gly Glu Thr His Leu Val Gln Asn Gly Ile Gln Leu Leu Asn Gly His
        195                 200                 205

Ala Pro Gly Ala Val Pro Asn Leu Ala Gly Leu Gln Gln Ala Asn Arg
    210                 215                 220

His His Gly Leu Leu Gly Gly Ala Leu Ala Asn Leu Phe Val Ile Val
225                 230                 235                 240

Gly Phe Ala Ala Phe Ala Tyr Thr Val Lys Tyr Val Leu Arg Ser Ile
                245                 250                 255

Ala Gln Glu

<210> SEQ ID NO 10
<211> LENGTH: 183
<212> TYPE: PRT
<213> ORGANISM: Homo sapiens

<400> SEQUENCE: 10

Met Ile Lys Leu Phe Ser Leu Lys Gln Gln Lys Lys Glu Glu Glu Ser
 1               5                  10                  15

Ala Gly Gly Thr Lys Gly Ser Ser Lys Lys Ala Ser Ala Ala Gln Leu
                20                  25                  30

Arg Ile Gln Lys Asp Ile Asn Glu Leu Asn Leu Pro Lys Thr Cys Asp
            35                  40                  45

Ile Ser Phe Ser Asp Pro Asp Asp Leu Leu Asn Phe Lys Leu Val Ile
        50                  55                  60

Cys Pro Asp Glu Gly Phe Tyr Lys Ser Gly Lys Phe Val Phe Ser Phe
 65                  70                  75                  80

Lys Val Gly Gln Gly Tyr Pro His Asp Pro Pro Lys Val Lys Cys Glu
                85                  90                  95

Thr Met Val Tyr His Pro Asn Ile Asp Leu Glu Gly Asn Val Cys Leu
            100                 105                 110

Asn Ile Leu Arg Glu Asp Trp Lys Pro Val Leu Thr Ile Asn Ser Ile
        115                 120                 125

Ile Tyr Gly Leu Gln Tyr Leu Phe Leu Glu Pro Asn Pro Glu Asp Pro
    130                 135                 140

Leu Asn Lys Glu Ala Ala Glu Val Leu Gln Asn Asn Arg Arg Leu Phe
145                 150                 155                 160

Glu Gln Asn Val Gln Arg Ser Met Arg Gly Gly Tyr Ile Gly Ser Thr
                165                 170                 175
```

Tyr Phe Glu Arg Cys Leu Lys
                180

<210> SEQ ID NO 11
<211> LENGTH: 152
<212> TYPE: PRT
<213> ORGANISM: Homo sapiens

<400> SEQUENCE: 11

Met Ala Gly Leu Pro Arg Arg Ile Ile Lys Glu Thr Gln Arg Leu Leu
1               5                   10                  15

Ala Glu Pro Val Pro Gly Ile Lys Ala Glu Pro Asp Glu Ser Asn Ala
            20                  25                  30

Arg Tyr Phe His Val Val Ile Ala Gly Pro Gln Asp Ser Pro Phe Glu
        35                  40                  45

Gly Gly Thr Phe Lys Leu Glu Leu Phe Leu Pro Glu Glu Tyr Pro Met
    50                  55                  60

Ala Ala Pro Lys Val Arg Phe Met Thr Lys Ile Tyr His Pro Asn Val
65                  70                  75                  80

Asp Lys Leu Gly Arg Ile Cys Leu Asp Ile Leu Lys Asp Lys Trp Ser
                85                  90                  95

Pro Ala Leu Gln Ile Arg Thr Val Leu Leu Ser Ile Gln Ala Leu Leu
            100                 105                 110

Ser Ala Pro Asn Pro Asp Asp Pro Leu Ala Asn Asp Val Ala Glu Gln
        115                 120                 125

Trp Lys Thr Asn Glu Ala Gln Ala Ile Glu Thr Ala Arg Ala Trp Thr
    130                 135                 140

Arg Leu Tyr Ala Met Asn Asn Ile
145                 150

<210> SEQ ID NO 12
<211> LENGTH: 1292
<212> TYPE: PRT
<213> ORGANISM: Homo sapiens

<400> SEQUENCE: 12

Met Ala Asp Pro Ala Ala Pro Thr Pro Ala Ala Pro Ala Pro Ala Gln
1               5                   10                  15

Ala Pro Ala Pro Ala Pro Glu Ala Val Pro Ala Pro Ala Ala Ala Pro
            20                  25                  30

Val Pro Ala Pro Ala Pro Ala Ser Asp Ser Ala Ser Gly Pro Ser Ser
        35                  40                  45

Asp Ser Gly Pro Glu Ala Gly Ser Gln Arg Leu Leu Phe Ser His Asp
    50                  55                  60

Leu Val Ser Gly Arg Tyr Arg Gly Ser Val His Phe Gly Leu Val Arg
65                  70                  75                  80

Leu Ile His Gly Glu Asp Ser Asp Ser Glu Gly Glu Glu Gly Arg
                85                  90                  95

Gly Ser Ser Gly Cys Ser Glu Ala Gly Gly Ala Gly His Glu Glu Gly
            100                 105                 110

Arg Ala Ser Pro Leu Arg Arg Gly Tyr Val Arg Val Gln Trp Tyr Pro
        115                 120                 125

Glu Gly Val Lys Gln His Val Lys Glu Thr Lys Leu Lys Leu Glu Asp
    130                 135                 140

Arg Ser Val Val Pro Arg Asp Val Val Arg His Met Arg Ser Thr Asp
145                 150                 155                 160

```
Ser Gln Cys Gly Thr Val Ile Asp Val Asn Ile Asp Cys Ala Val Lys
                165                 170                 175

Leu Ile Gly Thr Asn Cys Ile Ile Tyr Pro Val Asn Ser Lys Asp Leu
            180                 185                 190

Gln His Ile Trp Pro Phe Met Tyr Gly Asp Tyr Ile Ala Tyr Asp Cys
        195                 200                 205

Trp Leu Gly Lys Val Tyr Asp Leu Lys Asn Gln Ile Ile Leu Lys Leu
    210                 215                 220

Ser Asn Gly Ala Arg Cys Ser Met Asn Thr Glu Asp Gly Ala Lys Leu
225                 230                 235                 240

Tyr Asp Val Cys Pro His Val Ser Asp Ser Gly Leu Phe Phe Asp Asp
                245                 250                 255

Ser Tyr Gly Phe Tyr Pro Gly Gln Val Leu Ile Gly Pro Ala Lys Ile
            260                 265                 270

Phe Ser Ser Val Gln Trp Leu Ser Gly Val Lys Pro Val Leu Ser Thr
        275                 280                 285

Lys Ser Lys Phe Arg Val Val Val Glu Glu Val Gln Val Val Glu Leu
    290                 295                 300

Lys Val Thr Trp Ile Thr Lys Ser Phe Cys Pro Gly Thr Asp Ser
305                 310                 315                 320

Val Ser Pro Pro Ser Val Ile Thr Gln Glu Asn Leu Gly Arg Val
                325                 330                 335

Lys Arg Leu Gly Cys Phe Asp His Ala Gln Arg Gln Leu Gly Glu Arg
            340                 345                 350

Cys Leu Tyr Val Phe Pro Ala Lys Val Glu Pro Ala Lys Ile Ala Trp
        355                 360                 365

Glu Cys Pro Glu Lys Asn Cys Ala Gln Gly Glu Gly Ser Met Ala Lys
    370                 375                 380

Lys Val Lys Arg Leu Leu Lys Lys Gln Val Val Arg Ile Met Ser Cys
385                 390                 395                 400

Ser Pro Asp Thr Gln Cys Ser Arg Asp His Ser Met Glu Asp Pro Asp
                405                 410                 415

Lys Lys Gly Glu Ser Lys Thr Lys Ser Glu Ala Glu Ser Ala Ser Pro
            420                 425                 430

Glu Glu Thr Pro Asp Gly Ser Ala Ser Pro Val Glu Met Gln Asp Glu
        435                 440                 445

Gly Ala Glu Glu Pro His Glu Ala Gly Glu Gln Leu Pro Pro Phe Leu
    450                 455                 460

Leu Lys Glu Gly Arg Asp Asp Arg Leu His Ser Ala Glu Gln Asp Ala
465                 470                 475                 480

Asp Asp Glu Ala Ala Asp Asp Thr Asp Thr Ser Ser Val Thr Ser
                485                 490                 495

Ser Ala Ser Ser Thr Thr Ser Ser Gln Ser Gly Ser Gly Thr Ser Arg
            500                 505                 510

Lys Lys Ser Ile Pro Leu Ser Ile Lys Asn Leu Lys Arg Lys His Lys
        515                 520                 525

Arg Lys Lys Asn Lys Ile Thr Arg Asp Phe Lys Pro Gly Asp Arg Val
    530                 535                 540

Ala Val Glu Val Val Thr Thr Met Thr Ser Ala Asp Val Met Trp Gln
545                 550                 555                 560

Asp Gly Ser Val Glu Cys Asn Ile Arg Ser Asn Asp Leu Phe Pro Val
                565                 570                 575
```

```
His His Leu Asp Asn Asn Glu Phe Cys Pro Gly Asp Phe Val Val Asp
            580                 585                 590

Lys Arg Val Gln Ser Cys Pro Asp Pro Ala Val Tyr Gly Val Val Gln
        595                 600                 605

Ser Gly Asp His Ile Gly Arg Thr Cys Met Val Lys Trp Phe Lys Leu
    610                 615                 620

Arg Pro Ser Gly Asp Asp Val Glu Leu Ile Gly Glu Glu Glu Asp Val
625                 630                 635                 640

Ser Val Tyr Asp Ile Ala Asp His Pro Asp Phe Arg Phe Arg Thr Thr
                645                 650                 655

Asp Ile Val Ile Arg Ile Gly Asn Thr Glu Asp Gly Ala Pro His Lys
            660                 665                 670

Glu Asp Glu Pro Ser Val Gly Gln Val Ala Arg Val Asp Val Ser Ser
        675                 680                 685

Lys Val Glu Val Val Trp Ala Asp Asn Ser Lys Thr Ile Ile Leu Pro
    690                 695                 700

Gln His Leu Tyr Asn Ile Glu Ser Glu Ile Glu Glu Ser Asp Tyr Asp
705                 710                 715                 720

Ser Val Glu Gly Ser Thr Ser Gly Ala Ser Ser Asp Glu Trp Glu Asp
                725                 730                 735

Asp Ser Asp Ser Trp Glu Thr Asp Asn Gly Leu Val Glu Asp Glu His
            740                 745                 750

Pro Lys Ile Glu Glu Pro Pro Ile Pro Pro Leu Glu Gln Pro Val Ala
        755                 760                 765

Pro Glu Asp Lys Gly Val Val Ile Ser Glu Ala Ala Thr Ala Ala
770                 775                 780

Val Gln Gly Ala Val Ala Met Ala Ala Pro Met Ala Gly Leu Met Glu
785                 790                 795                 800

Lys Ala Gly Lys Asp Gly Pro Pro Lys Ser Phe Arg Glu Leu Lys Glu
                805                 810                 815

Ala Ile Lys Ile Leu Glu Ser Leu Lys Asn Met Thr Val Glu Gln Leu
            820                 825                 830

Leu Thr Gly Ser Pro Thr Ser Pro Thr Val Glu Pro Glu Lys Pro Thr
        835                 840                 845

Arg Glu Lys Lys Phe Leu Asp Asp Ile Lys Lys Leu Gln Glu Asn Leu
850                 855                 860

Lys Lys Thr Leu Asp Asn Val Ala Ile Val Glu Glu Lys Met Glu
865                 870                 875                 880

Ala Val Pro Asp Val Glu Arg Lys Glu Asp Lys Pro Glu Gly Gln Ser
                885                 890                 895

Pro Val Lys Ala Glu Trp Pro Ser Glu Thr Pro Val Leu Cys Gln Gln
            900                 905                 910

Cys Gly Gly Lys Pro Gly Val Thr Phe Thr Ser Ala Lys Gly Glu Val
        915                 920                 925

Phe Ser Val Leu Glu Phe Ala Pro Ser Asn His Ser Phe Lys Lys Ile
930                 935                 940

Glu Phe Gln Pro Pro Glu Ala Lys Lys Phe Phe Ser Thr Val Arg Lys
945                 950                 955                 960

Glu Met Ala Leu Leu Ala Thr Ser Leu Pro Glu Gly Ile Met Val Lys
                965                 970                 975

Thr Phe Glu Asp Arg Met Asp Leu Phe Ser Ala Leu Ile Lys Gly Pro
            980                 985                 990

Thr Arg Thr Pro Tyr Glu Asp Gly  Leu Tyr Leu Phe Asp  Ile Gln Leu
```

```
                995                 1000                1005
Pro Asn Ile Tyr Pro Ala Val Pro Pro His Phe Cys Tyr Leu Ser
    1010                1015                1020

Gln Cys Ser Gly Arg Leu Asn Pro Asn Leu Tyr Asp Asn Gly Lys
    1025                1030                1035

Val Cys Val Ser Leu Leu Gly Thr Trp Ile Gly Lys Gly Thr Glu
    1040                1045                1050

Arg Trp Thr Ser Lys Ser Ser Leu Leu Gln Val Leu Ile Ser Ile
    1055                1060                1065

Gln Gly Leu Ile Leu Val Asn Glu Pro Tyr Tyr Asn Glu Ala Gly
    1070                1075                1080

Phe Asp Ser Asp Arg Gly Leu Gln Glu Gly Tyr Glu Asn Ser Arg
    1085                1090                1095

Cys Tyr Asn Glu Met Ala Leu Ile Arg Val Val Gln Ser Met Thr
    1100                1105                1110

Gln Leu Val Arg Arg Pro Pro Glu Val Phe Glu Gln Glu Ile Arg
    1115                1120                1125

Gln His Phe Ser Thr Gly Gly Trp Arg Leu Val Asn Arg Ile Glu
    1130                1135                1140

Ser Trp Leu Glu Thr His Ala Leu Leu Glu Lys Ala Gln Ala Leu
    1145                1150                1155

Pro Asn Gly Val Pro Lys Ala Ser Ser Ser Pro Glu Pro Pro Ala
    1160                1165                1170

Val Ala Glu Leu Ser Asp Ser Gly Gln Gln Glu Pro Glu Asp Gly
    1175                1180                1185

Gly Pro Ala Pro Gly Glu Ala Ser Gln Gly Ser Asp Ser Glu Gly
    1190                1195                1200

Gly Ala Gln Gly Leu Ala Ser Ala Ser Arg Asp His Thr Asp Gln
    1205                1210                1215

Thr Ser Glu Thr Ala Pro Asp Ala Ser Val Pro Ser Val Lys
    1220                1225                1230

Pro Lys Lys Arg Arg Lys Ser Tyr Arg Ser Phe Leu Pro Glu Lys
    1235                1240                1245

Ser Gly Tyr Pro Asp Ile Gly Phe Pro Leu Phe Pro Leu Ser Lys
    1250                1255                1260

Gly Phe Ile Lys Ser Ile Arg Gly Val Leu Thr Gln Phe Arg Ala
    1265                1270                1275

Ala Leu Leu Glu Ala Gly Met Pro Glu Cys Thr Glu Asp Lys
    1280                1285                1290

<210> SEQ ID NO 13
<211> LENGTH: 222
<212> TYPE: PRT
<213> ORGANISM: Homo sapiens

<400> SEQUENCE: 13

Met Asn Ser Asn Val Glu Asn Leu Pro Pro His Ile Ile Arg Leu Val
1               5                   10                  15

Tyr Lys Glu Val Thr Thr Leu Thr Ala Asp Pro Pro Asp Gly Ile Lys
            20                  25                  30

Val Phe Pro Asn Glu Glu Asp Leu Thr Asp Leu Gln Val Thr Ile Glu
        35                  40                  45

Gly Pro Glu Gly Thr Pro Tyr Ala Gly Gly Leu Phe Arg Met Lys Leu
    50                  55                  60
```

```
Leu Leu Gly Lys Asp Phe Pro Ala Ser Pro Lys Gly Tyr Phe Leu
 65                  70                  75                  80

Thr Lys Ile Phe His Pro Asn Val Gly Ala Asn Gly Glu Ile Cys Val
                 85                  90                  95

Asn Val Leu Lys Arg Asp Trp Thr Ala Glu Leu Gly Ile Arg His Val
            100                 105                 110

Leu Leu Thr Ile Lys Cys Leu Leu Ile His Pro Asn Pro Glu Ser Ala
            115                 120                 125

Leu Asn Glu Glu Ala Gly Arg Leu Leu Leu Glu Asn Tyr Glu Glu Tyr
130                 135                 140

Ala Ala Arg Ala Arg Leu Leu Thr Glu Ile His Gly Ala Gly Gly
145                 150                 155                 160

Pro Ser Gly Arg Ala Glu Ala Gly Arg Ala Leu Ala Ser Gly Thr Glu
                165                 170                 175

Ala Ser Ser Thr Asp Pro Gly Ala Pro Gly Gly Pro Gly Gly Ala Glu
            180                 185                 190

Gly Pro Met Ala Lys Lys His Ala Gly Glu Arg Asp Lys Lys Leu Ala
        195                 200                 205

Ala Lys Lys Lys Thr Asp Lys Lys Arg Ala Leu Arg Arg Leu
210                 215                 220
```

<210> SEQ ID NO 14
<211> LENGTH: 1215
<212> TYPE: PRT
<213> ORGANISM: Unknown
<220> FEATURE:
<223> OTHER INFORMATION: HDAC6

<400> SEQUENCE: 14

```
Met Thr Ser Thr Gly Gln Asp Ser Thr Thr Thr Arg Gln Arg Arg Ser
 1               5                  10                  15

Arg Gln Asn Pro Gln Ser Pro Pro Gln Asp Ser Ser Val Thr Ser Lys
                20                  25                  30

Arg Asn Ile Lys Lys Gly Ala Val Pro Arg Ser Ile Pro Asn Leu Ala
            35                  40                  45

Glu Val Lys Lys Lys Gly Lys Met Lys Lys Leu Gly Gln Ala Met Glu
 50                  55                  60

Glu Asp Leu Ile Val Gly Leu Gln Gly Met Asp Leu Asn Leu Glu Ala
 65                  70                  75                  80

Glu Ala Leu Ala Gly Thr Gly Leu Val Leu Asp Glu Gln Leu Asn Glu
                 85                  90                  95

Phe His Cys Leu Trp Asp Asp Ser Phe Pro Glu Gly Pro Glu Arg Leu
            100                 105                 110

His Ala Ile Lys Glu Gln Leu Ile Gln Glu Gly Leu Leu Asp Arg Cys
        115                 120                 125

Val Ser Phe Gln Ala Arg Phe Ala Glu Lys Glu Glu Leu Met Leu Val
130                 135                 140

His Ser Leu Glu Tyr Ile Asp Leu Met Glu Thr Thr Gln Tyr Met Asn
145                 150                 155                 160

Glu Gly Glu Leu Arg Val Leu Ala Asp Thr Tyr Asp Ser Val Tyr Leu
                165                 170                 175

His Pro Asn Ser Tyr Ser Cys Ala Cys Leu Ala Ser Gly Ser Val Leu
            180                 185                 190

Arg Leu Val Asp Ala Val Leu Gly Ala Glu Ile Arg Asn Gly Met Ala
        195                 200                 205
```

```
Ile Ile Arg Pro Pro Gly His His Ala Gln His Ser Leu Met Asp Gly
    210                 215                 220

Tyr Cys Met Phe Asn His Val Ala Val Ala Ala Arg Tyr Ala Gln Gln
225                 230                 235                 240

Lys His Arg Ile Arg Arg Val Leu Ile Val Asp Trp Asp Val His His
                245                 250                 255

Gly Gln Gly Thr Gln Phe Thr Phe Asp Gln Asp Pro Ser Val Leu Tyr
            260                 265                 270

Phe Ser Ile His Arg Tyr Glu Gln Gly Arg Phe Trp Pro His Leu Lys
        275                 280                 285

Ala Ser Asn Trp Ser Thr Thr Gly Phe Gly Gln Gly Gln Gly Tyr Thr
    290                 295                 300

Ile Asn Val Pro Trp Asn Gln Val Gly Met Arg Asp Ala Asp Tyr Ile
305                 310                 315                 320

Ala Ala Phe Leu His Val Leu Leu Pro Val Ala Leu Glu Phe Gln Pro
                325                 330                 335

Gln Leu Val Leu Val Ala Ala Gly Phe Asp Ala Leu Gln Gly Asp Pro
            340                 345                 350

Lys Gly Glu Met Ala Ala Thr Pro Ala Gly Phe Ala Gln Leu Thr His
        355                 360                 365

Leu Leu Met Gly Leu Ala Gly Gly Lys Leu Ile Leu Ser Leu Glu Gly
    370                 375                 380

Gly Tyr Asn Leu Arg Ala Leu Ala Glu Gly Val Ser Ala Ser Leu His
385                 390                 395                 400

Thr Leu Leu Gly Asp Pro Cys Pro Met Leu Glu Ser Pro Gly Ala Pro
                405                 410                 415

Cys Arg Ser Ala Gln Ala Ser Val Ser Cys Ala Leu Glu Ala Leu Glu
            420                 425                 430

Pro Phe Trp Glu Val Leu Val Arg Ser Thr Glu Thr Val Glu Arg Asp
        435                 440                 445

Asn Met Glu Glu Asp Asn Val Glu Glu Ser Glu Glu Glu Gly Pro Trp
    450                 455                 460

Glu Pro Pro Val Leu Pro Ile Leu Thr Trp Pro Val Leu Gln Ser Arg
465                 470                 475                 480

Thr Gly Leu Val Tyr Asp Gln Asn Met Met Asn His Cys Asn Leu Trp
                485                 490                 495

Asp Ser His His Pro Glu Val Pro Gln Arg Ile Leu Arg Ile Met Cys
            500                 505                 510

Arg Leu Glu Glu Leu Gly Leu Ala Gly Arg Cys Leu Thr Leu Thr Pro
        515                 520                 525

Arg Pro Ala Thr Glu Ala Glu Leu Leu Thr Cys His Ser Ala Glu Tyr
    530                 535                 540

Val Gly His Leu Arg Ala Thr Glu Lys Met Lys Thr Arg Glu Leu His
545                 550                 555                 560

Arg Glu Ser Ser Asn Phe Asp Ser Ile Tyr Ile Cys Pro Ser Thr Phe
                565                 570                 575

Ala Cys Ala Gln Leu Ala Thr Gly Ala Ala Cys Arg Leu Val Glu Ala
            580                 585                 590

Val Leu Ser Gly Glu Val Leu Asn Gly Ala Ala Val Val Arg Pro Pro
        595                 600                 605

Gly His His Ala Glu Gln Asp Ala Ala Cys Gly Phe Cys Phe Phe Asn
    610                 615                 620

Ser Val Ala Val Ala Ala Arg His Ala Gln Thr Ile Ser Gly His Ala
```

-continued

```
            625                 630                 635                 640
Leu Arg Ile Leu Ile Val Asp Trp Asp Val His His Gly Asn Gly Thr
                    645                 650                 655
Gln His Met Phe Glu Asp Pro Ser Val Leu Tyr Val Ser Leu His
            660                 665                 670
Arg Tyr Asp His Gly Thr Phe Phe Pro Met Gly Asp Glu Gly Ala Ser
            675                 680                 685
Ser Gln Ile Gly Arg Ala Ala Gly Thr Gly Phe Thr Val Asn Val Ala
        690                 695                 700
Trp Asn Gly Pro Arg Met Gly Asp Ala Asp Tyr Leu Ala Ala Trp His
705                 710                 715                 720
Arg Leu Val Leu Pro Ile Ala Tyr Glu Phe Asn Pro Glu Leu Val Leu
                725                 730                 735
Val Ser Ala Gly Phe Asp Ala Ala Arg Gly Asp Pro Leu Gly Gly Cys
            740                 745                 750
Gln Val Ser Pro Glu Gly Tyr Ala His Leu Thr His Leu Leu Met Gly
        755                 760                 765
Leu Ala Ser Gly Arg Ile Ile Leu Ile Leu Glu Gly Gly Tyr Asn Leu
    770                 775                 780
Thr Ser Ile Ser Glu Ser Met Ala Ala Cys Thr Arg Ser Leu Leu Gly
785                 790                 795                 800
Asp Pro Pro Leu Leu Thr Leu Pro Arg Pro Leu Ser Gly Ala
                805                 810                 815
Leu Ala Ser Ile Thr Glu Thr Ile Gln Val His Arg Arg Tyr Trp Arg
            820                 825                 830
Ser Leu Arg Val Met Lys Val Glu Asp Arg Glu Gly Pro Ser Ser Ser
        835                 840                 845
Lys Leu Val Thr Lys Ala Pro Gln Pro Ala Lys Pro Arg Leu Ala
    850                 855                 860
Glu Arg Met Thr Thr Arg Glu Lys Lys Val Leu Glu Ala Gly Met Gly
865                 870                 875                 880
Lys Val Thr Ser Ala Ser Phe Gly Glu Glu Ser Thr Pro Gly Gln Thr
                885                 890                 895
Asn Ser Glu Thr Ala Val Val Ala Leu Thr Gln Asp Gln Pro Ser Glu
            900                 905                 910
Ala Ala Thr Gly Gly Ala Thr Leu Ala Gln Thr Ile Ser Glu Ala Ala
        915                 920                 925
Ile Gly Gly Ala Met Leu Gly Gln Thr Thr Ser Glu Glu Ala Val Gly
    930                 935                 940
Gly Ala Thr Pro Asp Gln Thr Thr Ser Glu Glu Thr Val Gly Gly Ala
945                 950                 955                 960
Ile Leu Asp Gln Thr Thr Ser Glu Asp Ala Val Gly Gly Ala Thr Leu
                965                 970                 975
Gly Gln Thr Thr Ser Glu Glu Ala Val Gly Gly Ala Thr Leu Ala Gln
            980                 985                 990
Thr Thr Ser Glu Ala Ala Met Glu  Gly Ala Thr Leu Asp  Gln Thr Thr
            995                 1000                1005
Ser Glu  Glu Ala Pro Gly Gly  Thr Glu Leu Ile Gln  Thr Pro Leu
    1010                1015                1020
Ala Ser  Ser Thr Asp His Gln  Thr Pro Thr Ser  Pro Val Gln
    1025                1030                1035
Gly Thr  Thr Pro Gln Ile Ser  Pro Ser Thr Leu Ile  Gly Ser Leu
    1040                1045                1050
```

Arg Thr Leu Glu Leu Gly Ser Glu Ser Gln Gly Ala Ser Glu Ser
1055                1060                1065

Gln Ala Pro Gly Glu Glu Asn Leu Leu Gly Glu Ala Ala Gly Gly
1070                1075                1080

Gln Asp Met Ala Asp Ser Met Leu Met Gln Gly Ser Arg Gly Leu
1085                1090                1095

Thr Asp Gln Ala Ile Phe Tyr Ala Val Thr Pro Leu Pro Trp Cys
1100                1105                1110

Pro His Leu Val Ala Val Cys Pro Ile Pro Ala Ala Gly Leu Asp
1115                1120                1125

Val Thr Gln Pro Cys Gly Asp Cys Gly Thr Ile Gln Glu Asn Trp
1130                1135                1140

Val Cys Leu Ser Cys Tyr Gln Val Tyr Cys Gly Arg Tyr Ile Asn
1145                1150                1155

Gly His Met Leu Gln His His Gly Asn Ser Gly His Pro Leu Val
1160                1165                1170

Leu Ser Tyr Ile Asp Leu Ser Ala Trp Cys Tyr Tyr Cys Gln Ala
1175                1180                1185

Tyr Val His His Gln Ala Leu Leu Asp Val Lys Asn Ile Ala His
1190                1195                1200

Gln Asn Lys Phe Gly Glu Asp Met Pro His Pro His
1205                1210                1215

<210> SEQ ID NO 15
<211> LENGTH: 491
<212> TYPE: PRT
<213> ORGANISM: Unknown
<220> FEATURE:
<223> OTHER INFORMATION: RABEX5

<400> SEQUENCE: 15

Met Ser Leu Lys Ser Glu Arg Arg Gly Ile His Val Asp Gln Ser Asp
1               5                   10                  15

Leu Leu Cys Lys Lys Gly Cys Gly Tyr Tyr Gly Asn Pro Ala Trp Gln
            20                  25                  30

Gly Phe Cys Ser Lys Cys Trp Arg Glu Glu Tyr His Lys Ala Arg Gln
        35                  40                  45

Lys Gln Ile Gln Glu Asp Trp Glu Leu Ala Glu Arg Leu Gln Arg Glu
    50                  55                  60

Glu Glu Glu Ala Phe Ala Ser Ser Gln Ser Ser Gln Gly Ala Gln Ser
65                  70                  75                  80

Leu Thr Phe Ser Lys Phe Glu Glu Lys Lys Thr Asn Glu Lys Thr Arg
                85                  90                  95

Lys Val Thr Thr Val Lys Lys Phe Phe Ser Ala Ser Ser Arg Val Gly
            100                 105                 110

Ser Lys Lys Glu Ile Gln Glu Ala Lys Ala Pro Ser Pro Ser Ile Asn
        115                 120                 125

Arg Gln Thr Ser Ile Glu Thr Asp Arg Val Ser Lys Glu Phe Ile Glu
    130                 135                 140

Phe Leu Lys Thr Phe His Lys Thr Gly Gln Glu Ile Tyr Lys Gln Thr
145                 150                 155                 160

Lys Leu Phe Leu Glu Gly Met His Tyr Lys Arg Asp Leu Ser Ile Glu
                165                 170                 175

Glu Gln Ser Glu Cys Ala Gln Asp Phe Tyr His Asn Val Ala Glu Arg
            180                 185                 190

Met Gln Thr Arg Gly Lys Val Pro Pro Glu Arg Val Glu Lys Ile Met
            195                 200                 205

Asp Gln Ile Glu Lys Tyr Ile Met Thr Arg Leu Tyr Lys Tyr Val Phe
        210                 215                 220

Cys Pro Glu Thr Thr Asp Asp Glu Lys Lys Asp Leu Ala Ile Gln Lys
225                 230                 235                 240

Arg Ile Arg Ala Leu Arg Trp Val Thr Pro Gln Met Leu Cys Val Pro
                245                 250                 255

Val Asn Glu Asp Ile Pro Glu Val Ser Asp Met Val Val Lys Ala Ile
            260                 265                 270

Thr Asp Ile Ile Glu Met Asp Ser Lys Arg Val Pro Arg Asp Lys Leu
        275                 280                 285

Ala Cys Ile Thr Lys Cys Ser Lys His Ile Phe Asn Ala Ile Lys Ile
290                 295                 300

Thr Lys Asn Glu Pro Ala Ser Ala Asp Asp Phe Leu Pro Thr Leu Ile
305                 310                 315                 320

Tyr Ile Val Leu Lys Gly Asn Pro Pro Arg Leu Gln Ser Asn Ile Gln
                325                 330                 335

Tyr Ile Thr Arg Phe Cys Asn Pro Ser Arg Leu Met Thr Gly Glu Asp
            340                 345                 350

Gly Tyr Tyr Phe Thr Asn Leu Cys Cys Ala Val Ala Phe Ile Glu Lys
        355                 360                 365

Leu Asp Ala Gln Ser Leu Asn Leu Ser Gln Glu Asp Phe Asp Arg Tyr
    370                 375                 380

Met Ser Gly Gln Thr Ser Pro Arg Lys Gln Glu Ala Glu Ser Trp Ser
385                 390                 395                 400

Pro Asp Ala Cys Leu Gly Val Lys Gln Met Tyr Lys Asn Leu Asp Leu
                405                 410                 415

Leu Ser Gln Leu Asn Glu Arg Gln Glu Arg Ile Met Asn Glu Ala Lys
            420                 425                 430

Lys Leu Glu Lys Asp Leu Ile Asp Trp Thr Asp Gly Ile Ala Arg Glu
        435                 440                 445

Val Gln Asp Ile Val Glu Lys Tyr Pro Leu Glu Ile Lys Pro Pro Asn
    450                 455                 460

Gln Pro Leu Ala Ala Ile Asp Ser Glu Asn Val Glu Asn Asp Lys Leu
465                 470                 475                 480

Pro Pro Pro Leu Gln Pro Gln Val Tyr Ala Gly
                485                 490

<210> SEQ ID NO 16
<211> LENGTH: 660
<212> TYPE: PRT
<213> ORGANISM: Unknown
<220> FEATURE:
<223> OTHER INFORMATION: NPL4

<400> SEQUENCE: 16

Leu Glu Arg Arg Trp Arg Arg Arg Glu Ala Gly Ala Gly Ala Glu
1               5                   10                  15

Ala Ala Ala Gly Ser Ala Arg Pro Leu Gly Arg Gln Ala Ala Ala
            20                  25                  30

Arg Gly Ser Ser Pro Glu Ala Gly Ala Ala Met Ala Glu Ser Ile
        35                  40                  45

Ile Ile Arg Val Gln Ser Pro Asp Gly Val Lys Arg Ile Thr Ala Thr
    50                  55                  60

```
Lys Arg Glu Thr Ala Ala Thr Phe Leu Lys Lys Val Ala Lys Glu Phe
 65                  70                  75                  80

Gly Phe Gln Asn Asn Gly Phe Ser Val Tyr Ile Asn Arg Asn Lys Thr
                 85                  90                  95

Gly Glu Ile Thr Ala Ser Ser Asn Lys Ser Leu Asn Leu Leu Lys Ile
            100                 105                 110

Lys His Gly Asp Leu Leu Phe Leu Phe Pro Ser Ser Leu Ala Gly Pro
        115                 120                 125

Ser Ser Glu Met Glu Thr Ser Val Pro Pro Gly Phe Lys Val Phe Gly
130                 135                 140

Ala Pro Asn Val Val Glu Asp Glu Ile Asp Gln Tyr Leu Ser Lys Gln
145                 150                 155                 160

Asp Gly Lys Ile Tyr Arg Ser Arg Asp Pro Gln Leu Cys Arg His Gly
                165                 170                 175

Pro Leu Gly Lys Cys Val His Cys Val Pro Leu Glu Pro Phe Asp Glu
            180                 185                 190

Asp Tyr Leu Asn His Leu Glu Pro Pro Val Lys His Met Ser Phe His
        195                 200                 205

Ala Tyr Ile Arg Lys Leu Thr Gly Gly Ala Asp Lys Gly Lys Phe Val
210                 215                 220

Ala Leu Glu Asn Ile Ser Cys Lys Ile Lys Ser Gly Cys Glu Gly His
225                 230                 235                 240

Leu Pro Trp Pro Asn Gly Ile Cys Thr Lys Cys Gln Pro Ser Ala Ile
                245                 250                 255

Thr Leu Asn Arg Gln Lys Tyr Arg His Val Asp Asn Ile Met Phe Glu
                260                 265                 270

Asn His Thr Val Ala Asp Arg Phe Leu Asp Phe Trp Arg Lys Thr Gly
        275                 280                 285

Asn Gln His Phe Gly Tyr Leu Tyr Gly Arg Tyr Thr Glu His Lys Asp
290                 295                 300

Ile Pro Leu Gly Ile Arg Ala Glu Val Ala Ala Ile Tyr Glu Pro Pro
305                 310                 315                 320

Gln Ile Gly Thr Gln Asn Ser Leu Glu Leu Leu Glu Asp Pro Lys Ala
                325                 330                 335

Glu Val Val Asp Glu Ile Ala Ala Lys Leu Gly Leu Arg Lys Val Gly
                340                 345                 350

Trp Ile Phe Thr Asp Leu Val Ser Glu Asp Thr Arg Lys Gly Thr Val
        355                 360                 365

Arg Tyr Ser Arg Asn Lys Asp Thr Tyr Phe Leu Ser Ser Glu Glu Cys
370                 375                 380

Ile Thr Ala Gly Asp Phe Gln Asn Lys His Pro Asn Met Cys Arg Leu
385                 390                 395                 400

Ser Pro Asp Gly His Phe Gly Ser Lys Phe Val Thr Ala Val Ala Thr
                405                 410                 415

Gly Gly Pro Asp Asn Gln Val His Phe Glu Gly Tyr Gln Val Ser Asn
                420                 425                 430

Gln Cys Met Ala Leu Val Arg Asp Glu Cys Leu Leu Pro Cys Lys Asp
        435                 440                 445

Ala Pro Glu Leu Gly Tyr Ala Lys Glu Ser Ser Glu Gln Tyr Val
450                 455                 460

Pro Asp Val Phe Tyr Lys Asp Val Asp Lys Phe Gly Asn Glu Ile Thr
465                 470                 475                 480
```

-continued

```
Gln Leu Ala Arg Pro Leu Pro Val Glu Tyr Leu Ile Ile Asp Ile Thr
            485                 490                 495

Thr Thr Phe Pro Lys Asp Pro Val Tyr Thr Phe Ser Ile Ser Gln Asn
        500                 505                 510

Pro Phe Pro Ile Glu Asn Arg Asp Val Leu Gly Glu Thr Gln Asp Phe
        515                 520                 525

His Ser Leu Ala Thr Tyr Leu Ser Gln Asn Thr Ser Ser Val Phe Leu
    530                 535                 540

Asp Thr Ile Ser Asp Phe His Leu Leu Leu Phe Leu Val Thr Asn Glu
545                 550                 555                 560

Val Met Pro Leu Gln Asp Ser Ile Ser Leu Leu Leu Glu Ala Val Arg
                565                 570                 575

Thr Arg Asn Glu Glu Leu Ala Gln Thr Trp Lys Arg Ser Glu Gln Trp
            580                 585                 590

Ala Thr Ile Glu Gln Leu Cys Ser Glu Tyr Pro His Pro Leu Pro Arg
        595                 600                 605

His Pro Val Ala Gly Ala Gly Glu Gln Pro Thr Leu His Ser Ser Pro
        610                 615                 620

Leu Pro Val Val Pro Trp Ile Pro His Pro Ala Ala Ser Trp Gln Val
625                 630                 635                 640

Pro Ser Ala Met Gln Arg Val Glu Thr Arg Pro Pro Cys Gln Ala Arg
                645                 650                 655

Gly Arg Leu Arg
            660

<210> SEQ ID NO 17
<211> LENGTH: 693
<212> TYPE: PRT
<213> ORGANISM: Unknown
<220> FEATURE:
<223> OTHER INFORMATION: TAB2

<400> SEQUENCE: 17

Met Ala Gln Gly Ser His Gln Ile Asp Phe Gln Val Leu His Asp Leu
1               5                   10                  15

Arg Gln Lys Phe Pro Glu Val Pro Glu Val Val Val Ser Arg Cys Met
            20                  25                  30

Leu Gln Asn Asn Asn Asn Leu Asp Ala Cys Cys Ala Val Leu Ser Gln
        35                  40                  45

Glu Ser Thr Arg Tyr Leu Tyr Gly Glu Gly Asp Leu Asn Phe Ser Asp
    50                  55                  60

Asp Ser Gly Ile Ser Gly Leu Arg Asn His Met Thr Ser Leu Asn Leu
65                  70                  75                  80

Asp Leu Gln Ser Gln Asn Ile Tyr His His Gly Arg Glu Gly Ser Arg
                85                  90                  95

Met Asn Gly Ser Arg Thr Leu Thr His Ser Ile Ser Asp Gly Gln Leu
            100                 105                 110

Gln Gly Gly Gln Ser Asn Ser Glu Leu Phe Gln Gln Glu Pro Gln Thr
        115                 120                 125

Ala Pro Ala Gln Val Pro Gln Gly Phe Asn Val Phe Gly Met Ser Ser
    130                 135                 140

Ser Ser Gly Ala Ser Asn Ser Ala Pro His Leu Gly Phe His Leu Gly
145                 150                 155                 160

Ser Lys Gly Thr Ser Ser Leu Ser Gln Gln Thr Pro Arg Phe Asn Pro
                165                 170                 175
```

```
Ile Met Val Thr Leu Ala Pro Asn Ile Gln Thr Gly Arg Asn Thr Pro
                180                 185                 190

Thr Ser Leu His Ile His Gly Val Pro Pro Val Leu Asn Ser Pro
    195                 200                 205

Gln Gly Asn Ser Ile Tyr Ile Arg Pro Tyr Ile Thr Thr Pro Gly Gly
210                 215                 220

Thr Thr Arg Gln Thr Gln Gln His Ser Gly Trp Val Ser Gln Phe Asn
225                 230                 235                 240

Pro Met Asn Pro Gln Gln Val Tyr Gln Pro Ser Gln Pro Gly Pro Trp
                245                 250                 255

Thr Thr Cys Pro Ala Ser Asn Pro Leu Ser His Thr Ser Ser Gln Gln
                260                 265                 270

Pro Asn Gln Gln Gly His Gln Thr Ser His Val Tyr Met Pro Ile Ser
                275                 280                 285

Ser Pro Thr Thr Ser Gln Pro Pro Thr Ile His Ser Ser Gly Ser Ser
    290                 295                 300

Gln Ser Ser Ala His Ser Gln Tyr Asn Ile Gln Asn Ile Ser Thr Gly
305                 310                 315                 320

Pro Arg Lys Asn Gln Ile Glu Ile Lys Leu Glu Pro Pro Gln Arg Asn
                325                 330                 335

Asn Ser Ser Lys Leu Arg Ser Ser Gly Pro Arg Thr Ser Ser Thr Ser
                340                 345                 350

Ser Ser Val Asn Ser Gln Thr Leu Asn Arg Asn Gln Pro Thr Val Tyr
    355                 360                 365

Ile Ala Ala Ser Pro Pro Asn Thr Asp Glu Leu Met Ser Arg Ser Gln
370                 375                 380

Pro Lys Val Tyr Ile Ser Ala Asn Ala Ala Thr Gly Asp Glu Gln Val
385                 390                 395                 400

Met Arg Asn Gln Pro Thr Leu Phe Ile Ser Thr Asn Ser Gly Ala Ser
                405                 410                 415

Ala Ala Ser Arg Asn Met Ser Gly Gln Val Ser Met Gly Pro Ala Phe
                420                 425                 430

Ile His His His Pro Pro Lys Ser Arg Ala Ile Gly Asn Asn Ser Ala
                435                 440                 445

Thr Ser Pro Arg Val Val Thr Gln Pro Asn Thr Lys Tyr Thr Phe
450                 455                 460

Lys Ile Thr Val Ser Pro Asn Lys Pro Pro Ala Val Ser Pro Gly Val
465                 470                 475                 480

Val Ser Pro Thr Phe Glu Leu Thr Asn Leu Leu Asn His Pro Asp His
                485                 490                 495

Tyr Val Glu Thr Glu Asn Ile Gln His Leu Thr Asp Pro Thr Leu Ala
                500                 505                 510

His Val Asp Arg Ile Ser Glu Thr Arg Lys Leu Ser Met Gly Ser Asp
    515                 520                 525

Asp Ala Ala Tyr Thr Gln Ala Leu Leu Val His Gln Lys Ala Arg Met
530                 535                 540

Glu Arg Leu Gln Arg Glu Leu Glu Ile Gln Lys Lys Leu Asp Lys
545                 550                 555                 560

Leu Lys Ser Glu Val Asn Glu Met Glu Asn Asn Leu Thr Arg Arg Arg
                565                 570                 575

Leu Lys Arg Ser Asn Ser Ile Ser Gln Ile Pro Ser Leu Glu Glu Met
                580                 585                 590

Gln Gln Leu Arg Ser Cys Asn Arg Gln Leu Gln Ile Asp Ile Asp Cys
```

```
              595                 600                 605
Leu Thr Lys Glu Ile Asp Leu Phe Gln Ala Arg Gly Pro His Phe Asn
        610                 615                 620

Pro Ser Ala Ile His Asn Phe Tyr Asp Asn Ile Gly Phe Val Gly Pro
625                 630                 635                 640

Val Pro Pro Lys Pro Lys Asp Gln Arg Ser Ile Ile Lys Thr Pro Lys
                645                 650                 655

Thr Gln Asp Thr Glu Asp Asp Glu Gly Ala Gln Trp Asn Cys Thr Ala
            660                 665                 670

Cys Thr Phe Leu Asn His Pro Ala Leu Ile Arg Cys Glu Gln Cys Glu
        675                 680                 685

Met Pro Arg His Phe
        690

<210> SEQ ID NO 18
<211> LENGTH: 835
<212> TYPE: PRT
<213> ORGANISM: Unknown
<220> FEATURE:
<223> OTHER INFORMATION: Iso T

<400> SEQUENCE: 18

Met Ala Glu Leu Ser Glu Glu Ala Leu Leu Ser Val Leu Pro Thr Ile
1               5                   10                  15

Arg Val Pro Lys Ala Gly Asp Arg Val His Lys Asp Glu Cys Ala Phe
            20                  25                  30

Ser Phe Asp Thr Pro Glu Ser Glu Gly Gly Leu Tyr Ile Cys Met Asn
        35                  40                  45

Thr Phe Leu Gly Phe Gly Lys Gln Tyr Val Glu Arg His Phe Asn Lys
    50                  55                  60

Thr Gly Gln Arg Val Tyr Leu His Leu Arg Arg Thr Arg Arg Pro Lys
65                  70                  75                  80

Glu Glu Asp Pro Ala Thr Gly Thr Gly Asp Pro Pro Arg Lys Lys Pro
                85                  90                  95

Thr Arg Leu Ala Ile Gly Val Glu Gly Gly Phe Asp Leu Ser Glu Glu
            100                 105                 110

Lys Phe Glu Leu Asp Glu Asp Val Lys Ile Val Ile Leu Pro Asp Tyr
        115                 120                 125

Leu Glu Ile Ala Arg Asp Gly Leu Gly Gly Leu Pro Asp Ile Val Arg
    130                 135                 140

Asp Arg Val Thr Ser Ala Val Glu Ala Leu Leu Ser Ala Asp Ser Ala
145                 150                 155                 160

Ser Arg Lys Gln Glu Val Gln Ala Trp Asp Gly Glu Val Arg Gln Val
                165                 170                 175

Ser Lys His Ala Phe Ser Leu Lys Gln Leu Asp Asn Pro Ala Arg Ile
            180                 185                 190

Pro Pro Cys Gly Trp Lys Cys Ser Lys Cys Asp Met Arg Glu Asn Leu
        195                 200                 205

Trp Leu Asn Leu Thr Asp Gly Ser Ile Leu Cys Gly Arg Arg Tyr Phe
    210                 215                 220

Asp Gly Ser Gly Gly Asn Asn His Ala Val Glu His Tyr Arg Glu Thr
225                 230                 235                 240

Gly Tyr Pro Leu Ala Val Lys Leu Gly Thr Ile Thr Pro Asp Gly Ala
                245                 250                 255

Asp Val Tyr Ser Tyr Asp Glu Asp Asp Met Val Leu Asp Pro Ser Leu
```

-continued

```
                260                 265                 270
Ala Glu His Leu Ser His Phe Gly Ile Asp Met Leu Lys Met Gln Lys
                275                 280                 285
Thr Asp Lys Thr Met Thr Glu Leu Glu Ile Asp Met Asn Gln Arg Ile
            290                 295                 300
Gly Glu Trp Glu Leu Ile Gln Glu Ser Gly Val Pro Leu Lys Pro Leu
305                 310                 315                 320
Phe Gly Pro Gly Tyr Thr Gly Ile Arg Asn Leu Gly Asn Ser Cys Tyr
                325                 330                 335
Leu Asn Ser Val Val Gln Val Leu Phe Ser Ile Pro Asp Phe Gln Arg
            340                 345                 350
Lys Tyr Val Asp Lys Leu Glu Lys Ile Phe Gln Asn Ala Pro Thr Asp
        355                 360                 365
Pro Thr Gln Asp Phe Ser Thr Gln Val Ala Lys Leu Gly His Gly Leu
    370                 375                 380
Leu Ser Gly Glu Tyr Ser Lys Pro Val Pro Glu Ser Gly Asp Gly Glu
385                 390                 395                 400
Arg Val Pro Glu Gln Lys Glu Val Gln Asp Gly Ile Ala Pro Arg Met
                405                 410                 415
Phe Lys Ala Leu Ile Gly Lys Gly His Pro Glu Phe Ser Thr Asn Arg
            420                 425                 430
Gln Gln Asp Ala Gln Glu Phe Phe Leu His Leu Ile Asn Met Val Glu
        435                 440                 445
Arg Asn Cys Arg Ser Ser Glu Asn Pro Asn Glu Val Phe Arg Phe Leu
    450                 455                 460
Val Glu Glu Arg Ile Lys Cys Leu Ala Thr Glu Lys Val Lys Tyr Thr
465                 470                 475                 480
Gln Arg Val Asp Tyr Ile Met Gln Leu Pro Val Pro Met Asp Ala Ala
                485                 490                 495
Leu Asn Lys Glu Glu Leu Leu Gly Tyr Glu Glu Lys Lys Arg Gln Ala
            500                 505                 510
Glu Glu Glu Lys Met Ala Leu Pro Glu Leu Val Arg Ala Gln Val Pro
        515                 520                 525
Phe Ser Ser Cys Leu Glu Ala Tyr Gly Ala Pro Glu Gln Val Asp Asp
    530                 535                 540
Phe Trp Ser Thr Ala Leu Gln Ala Lys Ser Val Ala Val Lys Thr Thr
545                 550                 555                 560
Arg Phe Ala Ser Phe Pro Asp Tyr Leu Val Ile Gln Ile Lys Lys Phe
                565                 570                 575
Thr Phe Gly Leu Asp Trp Val Pro Lys Lys Leu Asp Val Ser Ile Glu
            580                 585                 590
Met Pro Glu Glu Leu Asp Ile Ser Gln Leu Arg Gly Thr Gly Leu Gln
        595                 600                 605
Pro Gly Glu Glu Glu Leu Pro Asp Ile Ala Pro Pro Leu Val Thr Pro
    610                 615                 620
Asp Glu Pro Lys Ala Pro Met Leu Asp Glu Ser Val Ile Ile Gln Leu
625                 630                 635                 640
Val Glu Met Gly Phe Pro Met Asp Ala Cys Arg Lys Ala Val Tyr Tyr
                645                 650                 655
Thr Asp Asn Ser Gly Ala Glu Ala Ala Met Asn Trp Val Met Ser His
            660                 665                 670
Met Asp Asp Pro Asp Phe Ala Asn Pro Leu Ile Leu Pro Gly Ser Ser
        675                 680                 685
```

```
Gly Pro Gly Ser Thr Ser Ala Ala Asp Pro Pro Glu Asp Cys
    690                 695                 700

Val Thr Thr Ile Val Ser Met Gly Phe Ser Arg Asp Gln Ala Leu Lys
705                 710                 715                 720

Ala Leu Arg Ala Thr Asn Asn Ser Leu Glu Arg Ala Val Asp Trp Ile
                725                 730                 735

Phe Ser His Ile Asp Asp Leu Asp Ala Glu Ala Met Asp Ile Ser
            740                 745                 750

Glu Gly Arg Ser Ala Ala Asp Ser Ile Ser Glu Ser Val Pro Val Gly
                755                 760                 765

Pro Lys Val Arg Asp Gly Pro Gly Lys Tyr Gln Leu Phe Ala Phe Ile
    770                 775                 780

Ser His Met Gly Thr Ser Thr Met Cys Gly His Tyr Val Cys His Ile
785                 790                 795                 800

Lys Lys Glu Gly Arg Trp Val Ile Tyr Asn Asp Gln Lys Val Cys Ala
                805                 810                 815

Ser Glu Lys Pro Pro Lys Asp Leu Gly Tyr Ile Tyr Phe Tyr Gln Arg
                820                 825                 830

Val Ala Ser
        835
```

<210> SEQ ID NO 19
<211> LENGTH: 142
<212> TYPE: PRT
<213> ORGANISM: Artificial sequence
<220> FEATURE:
<223> OTHER INFORMATION: Synthetic sequence: Ubc consensus

<400> SEQUENCE: 19

```
Ser Lys Arg Leu Gln Lys Glu Leu Lys Asp Leu Lys Lys Asp Pro Pro
1               5                   10                  15

Ser Gly Ile Ser Ala Glu Pro Val Glu Glu Asn Leu Leu Glu Trp His
                20                  25                  30

Gly Thr Ile Arg Gly Pro Pro Asp Thr Pro Tyr Glu Gly Gly Ile Phe
            35                  40                  45

Lys Leu Asp Ile Glu Phe Pro Glu Asp Tyr Pro Phe Lys Pro Pro Lys
    50                  55                  60

Val Arg Phe Val Thr Lys Ile Tyr His Pro Pro Asn Val Asp Glu Asn
65                  70                  75                  80

Gly Lys Ile Cys Leu Ser Ile Leu Lys Thr His Gly Trp Ser Pro Ala
                85                  90                  95

Tyr Thr Leu Arg Thr Val Leu Leu Ser Leu Gln Ser Leu Leu Asn Glu
                100                 105                 110

Pro Asn Pro Ser Asp Pro Leu Asn Ala Glu Ala Ala Lys Leu Tyr Lys
            115                 120                 125

Glu Asn Arg Glu Glu Phe Lys Lys Lys Ala Arg Glu Trp Thr
        130                 135                 140
```

<210> SEQ ID NO 20
<211> LENGTH: 16
<212> TYPE: PRT
<213> ORGANISM: Artificial sequence
<220> FEATURE:
<223> OTHER INFORMATION: Synthetic sequence: Ubc Motif Consensus
<220> FEATURE:
<221> NAME/KEY: VARIANT
<222> LOCATION: (1)..(1)
<223> OTHER INFORMATION: Xaa is Phe, Tyr, Trp, Leu, or Ser

```
<220> FEATURE:
<221> NAME/KEY: VARIANT
<222> LOCATION: (3)..(3)
<223> OTHER INFORMATION: Xaa is Pro or Cys
<220> FEATURE:
<221> NAME/KEY: VARIANT
<222> LOCATION: (4)..(4)
<223> OTHER INFORMATION: Xaa is Asn or His
<220> FEATURE:
<221> NAME/KEY: VARIANT
<222> LOCATION: (5)..(5)
<223> OTHER INFORMATION: Xaa is Leu, Ile, or Val
<220> FEATURE:
<221> NAME/KEY: VARIANT
<222> LOCATION: (6)..(9)
<223> OTHER INFORMATION: Xaa is any amino acid
<220> FEATURE:
<221> NAME/KEY: VARIANT
<222> LOCATION: (6)..(9)
<223> OTHER INFORMATION: Any one Xaa may be present or absent-
      represents either 3 or 4 amino acids
<220> FEATURE:
<221> NAME/KEY: VARIANT
<222> LOCATION: (11)..(11)
<223> OTHER INFORMATION: Xaa is any amino acid
<220> FEATURE:
<221> NAME/KEY: VARIANT
<222> LOCATION: (12)..(12)
<223> OTHER INFORMATION: Xaa is Leu, Ile, or Val
<220> FEATURE:
<221> NAME/KEY: VARIANT
<222> LOCATION: (14)..(14)
<223> OTHER INFORMATION: Xaa is Leu, Ile, or Val
<220> FEATURE:
<221> NAME/KEY: VARIANT
<222> LOCATION: (15)..(15)
<223> OTHER INFORMATION: Xaa is any amino acid
<220> FEATURE:
<221> NAME/KEY: VARIANT
<222> LOCATION: (16)..(16)
<223> OTHER INFORMATION: Xaa is Leu, Ile, or Val

<400> SEQUENCE: 20

Xaa His Xaa Xaa Xaa Xaa Xaa Xaa Xaa Gly Xaa Xaa Cys Xaa Xaa Xaa
1               5                   10                  15

<210> SEQ ID NO 21
<211> LENGTH: 37
<212> TYPE: DNA
<213> ORGANISM: Artificial sequence
<220> FEATURE:
<223> OTHER INFORMATION: Synthetic sequence: UBP-FW Primer

<400> SEQUENCE: 21
ccaaggttcc atggtacggc aggtgtctaa gcatgcc                           37

<210> SEQ ID NO 22
<211> LENGTH: 44
<212> TYPE: DNA
<213> ORGANISM: Artificial sequence
<220> FEATURE:
<223> OTHER INFORMATION: Synthetic sequence: UBP-RV Primer

<400> SEQUENCE: 22
gcctagcggc cgcttatgtc ttctgcatct tcagcatgtc gatg                   44

<210> SEQ ID NO 23
<211> LENGTH: 36
<212> TYPE: DNA
<213> ORGANISM: Artificial sequence
<220> FEATURE:
<223> OTHER INFORMATION: Synthetic sequence: NZFfus663FW Primer
```

```
<400> SEQUENCE: 23
ccaaggttcc atggatgagg gagctcagtg gaattg                                 36

<210> SEQ ID NO 24
<211> LENGTH: 37
<212> TYPE: DNA
<213> ORGANISM: Artificial sequence
<220> FEATURE:
<223> OTHER INFORMATION: Synthetic sequence: NZFfus693RV Primer

<400> SEQUENCE: 24
gcctagcggc cgcttatcag aaatgccttg gcatctc                                37

<210> SEQ ID NO 25
<211> LENGTH: 4
<212> TYPE: PRT
<213> ORGANISM: Artificial sequence
<220> FEATURE:
<223> OTHER INFORMATION: Synthetic sequence: Lysine residue addition

<400> SEQUENCE: 25

Leu Arg Gly Gly
1

<210> SEQ ID NO 26
<211> LENGTH: 783
<212> TYPE: DNA
<213> ORGANISM: Homo sapiens

<400> SEQUENCE: 26
ggcacgagcg agttcctgtc tctctgccaa cgccgcccgg atggcttccc aaaaccgcga       60
cccagccgcc actagcgtcg ccgccgcccg taaaggagct gagccgagcg ggggcgccgc      120
ccggggtccg gtgggcaaaa ggctacagca ggagctgatg accctcatga tgtctggcga      180
taaagggatt tctgccttcc ctgaatcaga caacctttc aaatgggtag ggaccatcca       240
tggagcagct ggaacagtat atgaagacct gaggtataag ctctcgctag agttccccag      300 tggctacccct acaatgcgc ccacagtgaa gttcctcacg ccctgctatc accccaacgt      360
ggacacccag ggtaacatat gcctggacat cctgaaggaa aagtggtctg ccctgtatga      420
tgtcaggacc attctgctct ccatccagag ccttctagga gaacccaaca ttgatagtcc      480
cttgaacaca catgctgccg agctctggaa aaaccccaca gcttttaaga agtacctgca      540
agaaacctac tcaaagcagg tcaccagcca ggagccctga cccaggctgc cagcctgtc       600 cttgtgtcgt ctttttaatt tttccttaga tggtctgtcc tttttgtgat ttctgtatag      660
gactctttat cttgagctgt ggtatttttg ttttgttttt gtcttttaaa ttaagcctcg      720
gttgagccct tgtatattaa ataaatgcat ttttgtcctt ttttaaaaaa aaaaaaaaaa      780
aaa                                                                     783

<210> SEQ ID NO 27
<211> LENGTH: 2669
<212> TYPE: DNA
<213> ORGANISM: Homo sapiens

<400> SEQUENCE: 27
aaaagagtct cgccggcgtc cccgcccgca cactcgcgca cactcgcgct cgggcgcaca       60
cggagcaggg accggcgccc ggagcgagcc agggagcggc taaccgggga ccaccgcgc      120 ggagccagcc tagctgccag cgagcccaac ccgcgacgac ccacgcccct gagccccgca      180
```

```
gccgacccct gccggccggt gtccccaccg ccatccctga cccatggcgc tgaagaggat    240
tcagaaagaa ttgagtgatc tacagcgcga tccacctgct cactgttcag ctggacctgt    300
gggagatgac ttgttccact ggcaagccac tattatgggg cctcctgata gcgcatatca    360
aggtggagtc ttcttctca ctgtacattt tccgacagat tatccttta aaccaccaaa    420 gattgctttc acaacaaaaa tttaccatcc aaacataaac agtaatggaa gtatttgtct    480
cgatattctg aggtcacaat ggtcaccagc tctgactgta tcaaagttt tattgtccat    540 atgttctcta ctttgtgatc ctaatccaga tgacccctta gtaccagata ttgcacaaat    600
ctataaatca gacaaagaaa aatacaacag acatgcaaga gaatggactc agaaatatgc    660
aatgtaaaaa tcaaaaacat tttcatatat accagagtac tgtaaaatct aggttttttt    720
caacattagc agtaaattga gcactgttta ctgtttcatt gtaccatgaa accatttgat    780
ttttacccat tttaaatgtg tttctgaagc aagacaaaac aaacttccaa aaataccctt    840
aagactgtga tgagagcatt tatcattttg tatgcattga gaaagacatt tattatggtt    900
tttaagatac ttggacatct gcatcttcag cttacaagat ctacatgca gctgaaaagc    960 aaccaaatta ttttttgctg aaactagatg ttttacatg agaaatactg tatgtgttgt    1020
ctaagatgtc agttttataa atctgtattc agatttcatt ctttgttagc tcactttata    1080
atttgtattt ttttactgta tagactaaat atattctatt tacatgtatg tcaactcatt    1140
acttttttcc tgtgaacagt attgaaaaac cccaacggct gataattaag tgaattaact    1200
gtgtctccct tgtcttagga tattctgtag attgattgca gatttcttaa atctgaaatg    1260
atctttacac tgtaattctc agcatactga ttatggagaa acacttgttt tgattttgtt    1320
atacttgact taactttatt gcaatgtgaa ttaattgcac tgctaagtag aagatgtgt    1380 aacttttatt tgttgctatt cacatttgaa ttttttcctg tataggcaat attatattga    1440 cacctttttac agatcttact gtagcttttt ccatataaat aaaatgcttt ttctactatt    1500
tgtcttgatt acttaaaaaa ataaaaatat aagtaaggat caaaactcta aaattttgca    1560
tgaaaattac atccaaattg tgaaaatcag atctattttg tttgccatta gtcaccatta    1620
gttatataaa ttttattgtt ttaggttagt atctctttac taaattgtca gtctataaga    1680
taatatatgt tgatcccttg ctgtagagga gaatttagag taatttgggg tttgtcttgg    1740
attatatcta aatggattat ttgttaaaag tactgaaatg agtataaggc agtatcaccc    1800
atccaaaaga aaggtcttta tagacctgca cagtcactag attaattcat taaaatgccc    1860
ccaccctgat gtaattgaca ttacatttct taacatttta aaatctagaa tttctaaaat    1920
ggaatttaat gccatcacaa tttgaaaaac ttttttttttt ttttactat agaagttaca    1980 aaggaagttc taaaattatg cctccctctg tttttataag ttgccatcga aaagtgattt    2040
aaataagcag gttatcttta tagattttaa agaaaactag aaagtttaa tgttttaact    2100 tggggaaaaa tacatctctt taatgtttag catgcttgtc aaccttgagt gagtgtcatt    2160
tttaagaaca gttgtagccc ttctgattat tgcagtagct gtagaagtat gtaagaatat    2220
gtgatgggtg tagtcattag caaagcattt aaatcacttg agtatttgt catggttcat    2280 tattattaaa gcacaaaata acctattgtt agaaatatg tgttttata aatgaatgta    2340 aaataattaa atgaattgtg aaatggatgt ttaagaaaat ataggcttaa aaagtaaatc    2400
tataaaatga tgtcttaaaa cagccatatc atgaaaaatt ctacttagct atattattat    2460
aagctacatt tgccctgaat ttgaacactc aacatcacta gatttaaata tttagtatat    2520
tttgatagta aagggttttg tttcttgaat atcttcactt taaacaaaaa aaaaaaacaa    2580
```

```
ctttcatttg tgtggcattt attttttggaa gtgtcttctt tttttctttt attaaagttt    2640
ttgaaacttg caaaaaaaaa aaaaaaaaa                                        2669

<210> SEQ ID NO 28
<211> LENGTH: 2879
<212> TYPE: DNA
<213> ORGANISM: Homo sapiens

<400> SEQUENCE: 28
gcttcgcagc gtcacgccct ccggggccgt ggcggcgacg gcggtgcgta gcttactcac      60
aggggcggcc cgtatccctc cgccgccggc gcggctcggc cctccctccc ctggcccgcc     120
aatccccgcg cctcccgacc tgcccctcgg tcgggcccac ccgtgctcc gacggcccca     180 ccccggcggc gcagcccgcc cgccgcgcg tccctcggtc cacctgcagc agggaggaag     240
acaggcaatc cctccggctg tccgaccaag agaggccggc cgagcccgag gcttgggctt     300
ttgctttctg gcggagggat ctgcggcggt ttaggaggcg gcgctgatcc tgggaggaag     360
aggcagctac ggcggcggcg gcggtggcgg ctagggcggc ggcgaataaa ggggccgccg     420
ccgggtgatg cggtgaccgc tgcggcaggc ccaggagctg agtgggcccc ggccctcagc     480
ccgtcccgcc ggaccccgctt cctcaactc tccatcttct cctgccgacc gagatcgccg     540
aggcggcctc aggctcccta gcccttccc cgtcccttcc ccgccccgt ccccgccccg      600 ggggccgccg ccaccgcct cccaccatgg ctctgaagag aatccacaag ctccctccac     660
aaaaccgcct gagctcgggc tgacagagga agccgttttg cccgatccac aagtatatcc     720
tgagttcact tacctcttgg gtggcagcac acatcggtcc accctgcttg tccagaaact     780
gttaagagtt ggaagttcag aagaaaaaaa aaaggaattg aatgatctgg cacgggaccc     840
tccagcacag tgttcagcag gtcctgttgg agatgatatg ttccattggc aagctacaat     900
aatgggccca aatgacagtc cctatcaggg tggagtattt ttcttgacaa ttcatttccc     960
aacagattac cccttcaaac cacctaaggt tgcatttaca acaagaattt atcatccaaa    1020
tattaacagt aatggcagca tttgtcttga tattctacga tcacagtggt ctccagcact    1080
aactatttca aaagtactct tgtccatctg ttctctgttg tgtgatccca atccagatga    1140
tcctttagtg cctgagattg ctcggatcta caaaacagat agagaaaagt caacagaat     1200 agctcgggaa tggactcaga agtatgcgat gtaattaaag aaattattgg ataacctcta    1260
caaataaaga taggggaact ctgaaagaga aagtccttt gatttccatt tgactgcttt     1320
ctatgagccc acgcctcatc ttcccctgtg cacatgttta cctgatacag cagtgctgcg    1380
tgttgtacat acttggaaca acaaactaga aatactgtac ttctgtacca acattgcctc    1440
ctagcagaga agtgtgtgtg tgacaagcca gttctacagg cattacctag gtgtgagact    1500
aaaagctttt cttattgact taaatttgga taacagcaag gtgtgagggg ggtggtgggt    1560
atggtgtgtg cttggatggg aaagaaaagg ctccactcac ctataggaga ttatttttaa    1620
gtggaatcca tttaaactca aaacagttat gaaaagcaag gtgaagaaca tgaagctgtg    1680
tctgtattca ttttattccg aaggagctac gtcttaggtg aaagttatga ccaaccagat    1740
taaactctac ccacatcctg catttttaagg tctaagttta actggtcaac atttaaatgg    1800
attggagcta ttagtacatc aagtgtgatg ggctttgttc ccaactcttt tacatctccc    1860 tacccccttca accttttggcc tttcagccct tctttctctc ttccatattc tttggtttgt    1920
atgtggtttc tcagttaata catagctaat agctcttatt tttcttatgt ttttaaccgc    1980
```

```
ttaggtctat ttggatgtaa gggtgaaaat tcatttgatg gaaatacttg tgtatattta    2040
aagacccaat tgctcctctg gagcttgtac tttcaagaat gattaatctg tgtaataaac    2100
tggttactac agtcattaca tataattttg tgtgaatagg cttttcatt tttaagaagt     2160 ttgtctagct gagattagtg gtggattttc tcccacttct gaaatgttca tttatactgg    2220
ttgcatttta agatcatgaa acaattccag ttacattgta aaaggatat cttacgagta     2280 atttattga acaagttaga ggcataagct taagagcatt tccatgaaac aacacatgca    2340
gcattccagg aacttgattg ttaaattcaa taagaaattt gctttattaa tgaaactaag    2400
ctgcatttca tcaaaacctt gtgacattcc cttggtacat aggacataaa acacagaggc    2460
attgctattt ggtaagttaa gcttctgtga ttgtaattat aaaagagcaa cattgaccaa    2520
acctgggaaa caagagcaca gtcttgtttg gagagtctac ataattactt tgcactaaca   2580
tttgcaggat gttcacacaa ttttaaattg tactgtatgt ggcttttga agtcttccct    2640 tgacccctagt aaaatatagc ttgaaacttg taaacaactg tgtttgccag aaacatcatt  2700
catgtgaact aggcaagtta cctttttcc ccccttcttt tcctaattgt aaactaggcc    2760
aacctgaaag ccatggctga tgctctagcc atcaggttct ttcaaatgca tctttacact   2820
cttgcacaaa agttaaggaa taaatgtcca ctgcttttgg ttttaaaaaa aaaaaaaaa    2879

<210> SEQ ID NO 29
<211> LENGTH: 2006
<212> TYPE: DNA
<213> ORGANISM: Homo sapiens

<400> SEQUENCE: 29
ggaatctcgt gtgaaggtgg ccctcctctt gggcctttaa cgtctgtaga tgctggagac     60
cagcagaaag gatactgtgt gcgatgagat aagcatgtga gaatgctttc taaccgaaag    120
tgcctttcaa aagaacttag tgatttggcc cgtgaccctc cagcacaatg ttctgcaggt    180
ccagttgggg atgatatgtt tcattggcaa gccacaatta tgggacctaa tgacagccca    240
tatcaaggcg gtgtattctt tttgacaatt cattttccta cagactaccc cttcaaacca    300
cctaaggttg catttacaac aagaatttat catccaaata ttaacagtaa tggcagcatt    360
tgtctcgata ttctaagatc acagtggtcg cctgctttaa caatttctaa agttctttta    420
tccatttgtt cactgctatg tgatccaaac ccagatgacc ccctagtgcc agagattgca    480
cggatctata aaacagacag agataagtac aacagaatat ctcgggaatg gactcagaag    540
tatgccatgt gatgctacct taagtcaga ataacctgca ttatagctgg aataaacttt      600
aaattactgt tcctttttg attttcttat ccggctgctc ccctatcaga cctcatcttt     660 tttaattttta tttttgttt acctccctcc attcattcac atgctcatct gagaagactt    720
aagttcttcc agctttggac aataactgct tttagaaact gtaaagtagt tacaagagaa    780
cagttgccca agactcagaa ttttttaaaaa aaaaaatgga gcatgtgtat tatgtggcca   840
atgtcttcac tctaacttgg ttatgagact aaaaccattc ctcactgctc taacatgctg    900
aagaaatcat ctgaggggga gggagatgga tgctcagttg tcacatcaaa ggatacagca   960
ttattctagc agcatccatt cttgtttaag ccttccactg ttagagattt gaggttacat    1020
gatatgcttt atgctcataa ctgatgtggc tggagaattg gtattgaatt tatagcatca    1080
gcagaacaga aaatgtgatg tattttatgc atgtcaataa aggaatgacc tgttcttgtt    1140
ctacagagaa tggaaattgg aagtcaaaca ccctttgtat tccaaaatag ggtctcaaac    1200
attttgtaat tttcatttaa attgttagga ggcttggagc tattagttaa tctatcttcc    1260
```

```
aatacactgt ttaatatagc actgaataaa tgatgcaagt tgtcaatgga tgagtgatca    1320
actaatagct ctgctagtaa ttgatttatt tttcttcaat aaagttgcat aaaccaatga    1380
gttagctgcc tggattaatc agtatgggaa acaatctttt gtaaatgcaa agctgttttt    1440
tgtatatact gttgggattt gcttcattgt ttgacatcaa atgatgatgt aaagttcgaa    1500
agagtgaata ttttgccatg ttcagttaaa gtgcacagtc tgttacaggt tgacacattg    1560
cttgacctga tttatgcaga attaataagc tatttggata gtgtagcttt aatgtgctgc    1620
acatgatact ggcagccota gagttcatag atggactttt gggacccagc agttttgaaa    1680
tgtgtttatg gagtttaaga aatttatttt ccaggtgcag ccctgtcta actgaaattt     1740 ctcttcacct tgtacacttg acagctgaaa aaaacaaca tgggagtaat aatgggtcaa    1800
aatttgcaaa ataaagtact gttttggtgt gggagttgtc atgaggctgt gttgaagtga    1860
cttatctatg tgggatattg agtatccatt gaaatggatt tgttcagcca tttacattaa    1920
tgagcattta aatgcaacag atatcatttc aggtgactta acatgaatga ataaaagtca    1980
atgctattgg aaaaaaaaaa aaaaaa                                         2006
```

```
<210> SEQ ID NO 30
<211> LENGTH: 1760
<212> TYPE: DNA
<213> ORGANISM: Homo sapiens

<400> SEQUENCE: 30
gacaggcgtg gtcgggtgcg tggtgcgtgg gtccggcttt cggtgactag acggtccgca     60
ggggacatcc cgtccctggg gcctccccag tctccctccc cctcgcgcct gggcagctct    120
ctcccagggc ttcggctcga gcctgcgacc tgcacggaca cccccccctc aggatctaaa    180
atgtccactg aggcacaaag agttgatgac agtccaagca ctagtggagg aagttccgat    240
ggagatcaac gtgaaagtgt tcagcaagaa ccagaaagag aacaagttca gcccaagaaa    300
aaggagggaa aaatatccag caaaaccgct gctaaattgt caactagtgc taaaagaatt    360
cagaaggaac ttgcagaaat cacattggac cctcctccca actgtagtgc tggacccaaa    420
ggagacaaca tttatgaatg gaggtcaact atattgggac cccoaggatc tgtctatgaa    480 ggagggggtgt tctttcttga cattaccttt tcaccagact atccgtttaa acccccctaag    540 gttaccttcc gaacaagaat ctatcactgt aatattaaca gccaaggtgt gatctgtctg    600
gacatcttaa aggacaactg gagtccggct ttaactattt ctaaagttct cctctccatc    660
tgctcacttc ttacagattg caaccctgct gaccctctgg tgggcagcat cgccacacag    720
tacatgacca acagagcaga gcatgaccgg atggccagac agtggaccaa gcggtacgcc    780
acataggggc ctgctgcctg ccgccccgcg ggacctgtgc aagcacattc accaagtgca    840
tcggtagccc tgcccacccc tccagacctc ggttcttatt ttcctatttt tattaaattt    900
ggaaccattt tgtgatggta tgttgtccat cttcccatcc cagttcttcc tgcccccctt    960
cctctctccc acgctctctt ttatctctca ttttattccc ttgttgattt ctgttaactt   1020
gaaagatttg ggattttttc ccacctcatc atagatggga actttgtttt tcagtgcaaa   1080
caatgttgga gctgtaatag taagagcttt cttacaaagc tttgtattac tgtgtggttt   1140 tgttttttttt gttgttgttt atttgattt gattttttt tcttttatgt gatctttggg    1200
aaaacacatt cagaattata tctcgtttct acttaaatgt agtgcttagg gttaattttt   1260
tgtactgaag tctttattgg tgggtgcatg ctactgggaa caagttttg tacaaaagct   1320
```

```
tcaatcagaa tcactgtgca ttactgagac tctgtttatc actagccttc tgtccctccc      1380
gcagaagact gttggattga acaaaataat atgtattttg atttacttaa agtgcttgta      1440
aatttcttag ggacctgcca cttttgactg tggatcagtt gatgtacact tgtattatta      1500
aagcactcaa taaatcactg tggctgataa ctgcacttct ggtaacccga catttgcttt      1560
gtgtcctggt gaccgctgta gccctacgtg cagtgaggct tgtctaattc aattacaggt      1620
tcaagtgtat ttttcatctc aaacctctaa tatttctttg gagttgagtt gcttagcatg      1680
tggaatttct ccagctgtca gtagcctgat gattttatgg ttgttatagt aaattgctat      1740
cattttacat attgactggg                                                  1760

<210> SEQ ID NO 31
<211> LENGTH: 1559
<212> TYPE: DNA
<213> ORGANISM: Homo sapiens

<400> SEQUENCE: 31
gactgcgcgg ccgggaggag ccgagccggg cggcggcggc gggaggctac agcgcgcggg        60
ggtctcccgc gtcccctccg cctcgccggg agctcgcgcc ctcgcccagc cgagctccca       120
cccccgcttt tttccgaagg cgctgggcgg cgccacccte cggccggagc ccggcactgc       180
acaaccccct ccgactttca atgttccaca ctcccccggcc agagcctcct cggcttcttt     240 tttccctcc cccccttcc cccccccaca gctgcctcca tttccttaag gaagggtttt        300
tttctctctc cctcccccac accgtagcgg cgcgcgagcg ggccgggcgg gcggccgagt      360
tttccaagag ataacttcac caagatgtcc agtgataggc aaaggtccga tgatgagagc      420
cccagcacca gcagtggcag ttcagatgcg gaccagcgag acccagccgc tccagagcct      480
gaagaacaag aggaaagaaa accttctgcc acccagcaga gaaaaacac caaactctct       540 agcaaaacca ctgctaagtt atccactagt gctaaaagaa ttcagaagga gctagctgaa       600
ataacccttg atcctcctcc taattgcagt gctgggccta aaggagataa catttatgaa       660
tggagatcaa ctatacttgg tccaccgggt tctgtatatg aaggtggtgt gttttttctg       720
gatatcacat tttcatcaga ttatccattt aagccaccaa aggttacttt ccgcaccaga      780
atctatcact gcaacatcaa cagtcaggga gtcatctgtc tggacatcct taaagacaac      840
tggagtcccg ctttgactat tcaaaggtt ttgctgtcta tttgttccct tttgacagac       900
tgcaaccctg cggatcctct ggttggaagc atagccactc agtatttgac caacagagca     960
gaacacgaca ggatagccag acagtggacc aagagatacg caacataatt cacataattt      1020
gtatgcagtg tgaaggagca gaaggcatct tctcactgtg ctgcaaatct ttatagcctt      1080
tacaatacgg acttctgtgt atatgttata ctgattctac tctgcttta tcctttggag     1140 cctgggagac tccccaaaaa ggtaaatgct atcaagagta gaactttgta gctgtagatt     1200
agttatgttt aaaacgccta cttgcaagtc ttgcttcttt gggatatcaa aatgtattt     1260 gtgatgtact aaggatactg gtcctgaagt ctaccaaata ttatagtgca ttttagccta     1320
attcattatc tgtatgaagt tataaaagta gctgtagatg gctaggaatt atgtcatttg     1380
tattaaaccc agatctattt ctgagtatgt ggttcatgct gttgtgaaaa atgttttacc     1440
ttttaccttt gtcagtttgt aatgagagga tttcctttta ccctttgtag ctcagagagc     1500
acctgatgta tcatctcaaa cacaataaac atgctcctga aggaaaaaaa aaaaaaaaa     1559

<210> SEQ ID NO 32
<211> LENGTH: 1366
```

```
<212> TYPE: DNA
<213> ORGANISM: Homo sapiens

<400> SEQUENCE: 32
gcgtctcgca gcagccgccc ggaccgggca tggtgttggg cgccgggccc gcctcgcctg      60
tctcggggag cccagggtaa aggcagcagt aatgctaacg ctagcaagta aactgaagcg     120
tgacgatggt ctcaaagggt cccggacggc agccacagcg tccgactcga ctcggagggt     180
ttctgtgaga gacaaattgc ttgttaaaga ggttgcagaa cttgaagcta atttaccttg     240
tacatgtaaa gtgcattttc ctgatccaaa caagcttcat tgttttcagc taacagtaac     300
cccagatgag ggttactacc agggtggaaa atttcagttt gaaactgaag ttcccgatgc     360
gtacaacatg gtgcctccca agtgaaatg cctgaccaag atctggcacc ccaacatcac      420
agagacaggg gaaatatgtc tgagtttatt gagagaacat tcaattgatg gcactggctg     480
ggctcccaca agaacattaa aggatgtcgt ttggggatta aactctttgt ttactgatct     540
tttgaatttt gatgatccac tgaatattga agctgcagaa catcatttgc gggacaagga     600
ggacttccgg aataaagtgg atgactacat caaacgttat gccagatgat aaaggggac      660
gattgcaggc ccatggactg tgttacagtt tgtctctaac atgaaacagc aagaggtagc     720
cccctctccc gtcctcatgc tccctctcag tcccctggat tgccccagtc ctgtgaccat     780
gttgccctga agaaccat cttcatgact gctcattgta gatggagaat tcaacataaa        840
tacagcaaga aaatgtgttt gggcttctga agagttgtct gcttaccta acatgtttac      900
tttttgaac ttgtactgta taggctgttg gtgaaattct taagaagttg taatgaactc      960
aaaattgagg ccagagcttg ctttcccttt tcccaaacaa aattggtttt ctgcacaagc    1020
gatgctaatg atgtgttcag tgtaactcgc agattggcaa taagataccc gctacaaact    1080
gtgattggat gcaaaatctc ttagcttctt tcacgaatgt tggccctgcc tagatgttgt    1140
gaagcctccc agaatgcata gagtcattca ctgtagatct cttattgaaa tgcgtatttt    1200
atttaatgta agtatatttt ggaacagatt tgtaatttgt acaattcaat gctttaatta    1260
tttttctat tctcatttag tttgtatttt cattgtatag agcagacaga aagatgttgg     1320
gtcaagcaac tattgaagag aaatacaaag aaaaaaaaaa aaaaaa                    1366

<210> SEQ ID NO 33
<211> LENGTH: 4360
<212> TYPE: DNA
<213> ORGANISM: Homo sapiens

<400> SEQUENCE: 33
gcggccgcgg cagggctggg cctgcgacta cccgaggagg ctgacctcca gcccgggcgc      60
ccggttcagc gccgcccgg ccggcgccgg tgcctgccag gcactcaggg aggcggggc       120
gcagtggagg aggcggcgcc atcgcgaagc gagcgcctcg cccgcactca gccttgccac    180
cccgcccgca gtccaggctg gactgggcgg catttgccga ggctcctcgg ccaggccccg    240
tccgcccgag ccgcgctgag acccgggcag cggccgcgtg gagaggaggt ggcagcggcc    300
cgggaggccg gagccaagcc agcgaccac catggagacc cgctacaacc tgaagagtcc    360
ggctgttaaa cgtttaatga aagaagcggc agaattgaaa gatccaacag atcattacca    420
tgcgcagcct ttagaggata acctttttga atggcacttc acggttagag ggccccaga    480
ctccgatttt gatggaggag tttatcacg gcggatagta ctgccaccag agtatcccat     540
gaaaccacca agcattattc tcctaacggc taatggtcga tttgaagtgg gcaagaaaat    600
```

```
ctgtttgagc atctcaggcc atcatcctga aacttggcag ccttcgtgga gtataaggac    660
agcattatta gccatcattg ggtttatgcc aacaaaagga gagggagcca taggttctct    720
agattacact cctgaggaaa gaagagcact tgccaaaaaa tcacaagatt tctgttgtga    780
aggatgtggc tctgccatga aggatgtcct gttgccttta aaatctggaa gcgattcaag    840
ccaagctgac caagaagcca agaactggc taggcaaata gctttaagg cagaagtcaa    900 ttcatctgga aagactatct ctgagtcaga cttaaaccac tcttttttcac taactgattt    960 acaagatgat atacctacaa cattccaggg tgctacggcc agtacatcgt acggactcca   1020
gaattcctca gcagcatcct ttcatcaacc tacccaacct gtagctaaga atacctccat   1080
gagccctcga cagcgccggg cccagcagca gagtcagaga aggttgtcta cttcaccaga   1140
tgtaatccag ggccaccagc caagagacaa ccacactgat catggtgggt cagctgtact   1200
gattgtcatc ctgactttgg cattggcagc tcttatattc cgacgaatat atctggcaaa   1260
cgaatacata tttgactttg agttataata tggttttgtg acttatgagc tgtgactcaa   1320
ctgcttcatt aaacattctg cattgggtat aatctaagaa ttgtttacaa aaagattatt   1380
ttgtatttac ccttcattcc ttttttttgat ccttgtaagt ttagtataaa tatatctaga   1440
cattcagact gtgtctagca gttacgtcct gcttaaaggg actagaagtc aaagttcctt   1500
gtctcactat ttgatctgct ttgcagggaa ataacttgtt ttttctcatg tttcatcttc   1560
tttttatgta aatttgtaat actttcctat attgcccttt gaaattttg gataaaagat   1620 gatgttttaa gttccaatga gtattactag ttactcaata ccacttattg agtactctgt   1680
ttctacgtat gtagaatgta tagggataga agagttgaaa agggaaagca aaactcctca   1740
agtagcttcc ttaaaatgtc attcatagga gatgtactgg aattgctcat tctgtgactt   1800
tatttgtgtc ctaaacattc ttcagtgaaa ataattttat ttcagtcaaa catttatgag   1860
gaaatgagat cacatctttg tcactggatg ctacttgaag agggagtact ttgtaaccac   1920
tttgatatgc tgttatcacc accccctgcc ctctgctgcc ataatcacac aaatttaaaa   1980
agaaagaaaa cagtcttcca tagattttta aggaagaaag ggcccaagcc aggagatcgc   2040
ttggttttct tccagaagtt aaatgggggg atctgaagat ttgaatgttt ggtctgcttt   2100
gaaatgtatg tcttttggga tgtattatat gcctagcttt ataatcagta taaattttaa   2160
ttattccagg aatatgcata atattgaaat atttcatgtc ctattttaat agaaaacctc   2220
agggcccaag taacagtgat agaagttaga aaaacctta cttagaattg tccacctagt   2280
cagagcccaa gaaagaattt tcagtggaaa aatcaatata aacttagtg ctagctagcg   2340 ccacagactc tagtagataa tattatcatc ataatggctg gtgaaaccat ataatcacag   2400
aaaaacattg ccttcagcat gttcagttcg cagcactgag ggcactcttg agggtgttgt   2460
taatgaagat ttaattttta aatacaggtg gttccaagct ttcaaatagg ttatgctcca   2520
aaagtgttat ttgtaagtta attttttttac aagtcaaaca atgttggaag tggtatttag   2580
gttctagatc ggtccacgaa agttagccca tatgtatatc ttgaatagta taggggaggg   2640
tattcataaa gtccttatgt ggttttaact aagtgaaatt atggacaaga gaaataattg   2700
taaaatcgtc ttaaggaaa atttaatttt tactcctgtt tatgggacat tcgttctatt   2760
aactgtcaga cacaatttct gttttcatct gagagccagt tttcctttat ttctacatct   2820
aaaataagaa catattgtac actattatat aatacagaat tgtcttaaac tttaataaat   2880
tcgcatttta aaggtgttta cagatttattt tttatctg tagctgaatt tgttaaagtc   2940
taaaaagctc aaggactta tgaagatctc attatatgag gaaaatcata ggttaccatt   3000
```

```
ttataactct attgccataa gaaaatacac tctaaaatct tgatttgaaa catattagaa    3060
accttgattc agtgctcagt ggtctcctag taagaagtca ccgacggtag cgtcatatga    3120
gaagaaagaa atccccacca cctcaacctc tgctgagatt gtgtgctagg aacagccttc    3180
cctccgtttc ccctcagtca aacttgagcc agcctctgga tcgatgtgat cttattgcat    3240
gtttccatgg ggtgtaccta tactttaagc caatcctgct gcattcactg ctaagttaaa    3300 taaaagcca agaagatttt gcactgtgca gatcctttgc tatctgactt gcatctcttc    3360
ccccacctgt cagctagcca cctgcttgtt tgtgttggga tatttttag cacctgaagc    3420 accatctgaa aggggcacca ttttcttctt ccctttgatc tcacatatgc tccctaaaaa    3480
tccttaagtt gtcaatctga tccccagtgt gaggttaatg agcaaaattg gtctttgggg    3540
ccctttttgt ccaagcccca ctgaaaggcc tcttcagaaa actattatct ttaaagccct    3600
actttaactc cttaattcca gcatacagct aaaactggat gtatattctg gcaagtaaag    3660
gctgaggact cctctttaat cctcagatct agataactca tgacattta tttgaccaac    3720 atagcacatg atgagatatc aaggtaatta aaatagcatg cttgaaaaaa aaatacgtaa    3780
tctgtttcac ctgtaactgt ttaagccaat aaactttca aaatttatgt aatgtggggc    3840
ttttatgtag cactttacgt tttcatgctg cttattgttt tattctactg aaaaaaatga    3900
atttcaagat tctcaacttt tttaatttca aaaattgttt attgtttga ctataggaat    3960 acaaaatttc ctattttggg agaataagaa ctctttttgt catttttggc tatgaataaa    4020
ctttctggtc ttttgagacc acccattttt atagatcaga atcagaaaac aggtaaacct    4080
cactcacaca tttggactca tttgaacaaa aatctaggcc aaaatactga aaagcctatg    4140
tgttttttta attggaagta tatgtaaggt taatgcattt agtgaacgtg actaacaaag    4200
actaatgtgc acattaacag atgtacttt taaggttta tgggaggctg tgcattgctc    4260
aaaagctgtt gggaacgcct tctgaacagt tgccttcaga actagtttga gctgctcaat    4320
aaaaccagtg actttactca taaaaaaaaa aaaaaaaaa                          4360
```

<210> SEQ ID NO 34
<211> LENGTH: 2267
<212> TYPE: DNA
<213> ORGANISM: Homo sapiens

<400> SEQUENCE: 34

```
ggttccgccc cgcgagcggc catcttggag gctgaggcgg cggcggcggc gctgcggcgg     60
gttcggtggg cccaatcccg gggcggtgcg gctgtttcgg gcgcgggccc cgcttttccg    120
caccctgctc cggcctcgac tacggcgagc ctgagcgcgg cggcggccca cgcgcagcga    180
cagggagaga tgagcagcac cagcagtaag agggctccga ccacggcaac ccagaggctg    240
aagcaggact accttcgcat taagaaagac ccggtgcctt acatctgtgc cgagcccctc    300
ccttcgaata ttctcgagtg gcactatgtc gtccgaggcc cagagatgac cccttatgaa    360
ggtggctatt atcatggaaa actaattttt cccagagaat ttccttttcaa acctcccagt    420 atctatatga tcactcccaa cgggagggtt aagtgcaaca ccaggctgtg tctttctatc    480
acggatttcc acccggacac gtggaacccg gcctggtctg tctccaccat cctgactggg    540
ctcctgagct tcatggtgga aagggccccc accctgggca gtatagagac gtcggacttc    600
acgaaaagac aactggcagt gcagagttta gcatttaatt tgaaagataa agtcttttgt    660
gaattatttc ctgaagtcgt ggaggagatt aaacaaaaac agaaagcaca agacgaactc    720
```

| | |
|---|---:|
| agtagcagac cccagactct ccccttgcca gacgtggttc cagacgggga gacgcacctc | 780 |
| gtccagaacg ggattcagct gctcaacggg catgcgccgg gggccgtccc aaacctcgca | 840 |
| gggctccagc aggccaaccg gcaccacgga ctcctgggtg gcgccctggc gaacttgttt | 900 |
| gtgatagttg ggtttgcagc ctttgcttac acggtcaagt acgtgctgag gagcatcgcg | 960 |
| caggagtgag gcccaggcgc cgagacccaa ggcgccactg agggcaccgc gcaccagagc | 1020 |
| gtgacctcgg caggctggac acactgccca gcacaggcag acccaccagg ctcctaggtt | 1080 |
| tagcttttaa aaacctgaaa ggggaagcaa aaaccaaaat gtgtgactgg gctttggagg | 1140 |
| agactggagc ctcagccctg tcctggccac gggccgctgg ggctggtgtg ggtgggcctt | 1200 |
| gtgtgctgga tttgtagctt atcttccgtg ttgtctttgg acctgtttta gtaaacccgt | 1260 |
| ttttcatttt attagatgtg gtcacttaga aatgcaaact tgctgccgac cgcgggctgc | 1320 |
| tcctgcgttc ttggagctcc tggcgcgttt ctcggagctc ccggctcctc agcgggtggg | 1380 |
| aacctcgggg cccaggggtg gagctggcgt ccgcgggtgc tggtctggcc tggccgtgtg | 1440 |
| gtgatgaggc ttagcggggc cagtgacggc cgtggctcag gatccataag tcggggtttg | 1500 |
| gtctcagcat ttacaaatgt gtttacagtc agaatgaaac acattccttc tagaaagtgc | 1560 |
| ttgggggttt ttgctgccct ggaagccagg agcctgctca ctccaaccac aagtcgccct | 1620 |
| tgactgcggc ggccgcgagc ggggcggggg ctgccggtgc cctccgcagg ccgggcctcc | 1680 |
| tgggcgcccc tcggtgctgc aggctggggg ccttgggta cctgcagagc ctttctctg | 1740 |
| aattccttat gtccggtggg ccagaagccc gtcctcctat gctggtggaa ggcggaggac | 1800 |
| cggagtccct gcagaaggcc ccgtgcactc ggggcctcc ctcacatccc gtgcccctg | 1860 |
| cgctggcctt cacagtaggt aatggctccg gcccgggtgt tcgctgtcca cggaacatgg | 1920 |
| cagaggggca ccccggcccg gaaagacgcc agagccagca ggggctgttt cgggccgcgt | 1980 |
| ggctccccgg gtctcggccg tctcccctct tctgcgtctg ttccgtgact tcgcctgggt | 2040 |
| gggatgtacc gcaggtgcat cgcgtcgagg tggggcacgg ccgccggcaa gaaacccacc | 2100 |
| ctgtccggag gcgggcgtga gacaagccca gcccgcacgc gctcatcttt cttcgttttt | 2160 |
| tgatcagttt attcagaatt gctctataat ttaccaattg tatgtattta acctattctt | 2220 |
| gtggaaaaaa aaggtctttc attatatctt tatttctgaa aaaaaaa | 2267 |

<210> SEQ ID NO 35
<211> LENGTH: 1540
<212> TYPE: DNA
<213> ORGANISM: Homo sapiens

<400> SEQUENCE: 35

| | |
|---|---:|
| aggcgcacaa cgcaggccgg gcgggaagag ccaaagcggg caggcggcgg aaatatccga | 60 |
| agcggcgggg cgcccgaggc cgttgccgac ctccgcgcta aagccgctgc tgccgcggaa | 120 |
| gacgatcctc cagtacccgc ccgccgtcac cgcagctgcc gtgtcctcct cccaccccta | 180 |
| gccgcacccc ctcgcggagg gatcagctga gcggccaaac ggcacggtcg ggggagcccc | 240 |
| gagtccgcag ctgcagcggg gcctgagacc agagttggcg agggcaagga aggagcggcc | 300 |
| ccgggcagtg ggggcggggc cggcggggcc cgagaacagc cgaatttggc cgagcgctgc | 360 |
| cgagcgagtc cgaggcgctg gccaggccg agccggact acgggagccg aggcgggccg | 420 |
| cgcggtgggc gcgagagga gcggagcggc cggcaggcc gggcgggtgg cggcagcagc | 480 |
| ggaggaggcc gcagctgcgg gtccgaggag cggaggcgac gcggcggcg gcgggggcc | 540 |
| gggtggccgg ggtcccgggc cccgcggcgg cggcagcggc ggcggcggcg gcaggatgat | 600 |

```
caagctgttc tcgctgaagc agcagaagaa ggaggaggag tcggcgggcg gcaccaaggg      660
cagcagcaag aaggcgtcgg cggcgcagct gcggatccag aaggacataa acagagctgaa     720 cctgcccaag acgtgtgata tcagcttctc agatccagac gacctcctca acttcaagct     780
ggtcatctgt cctgatgagg gcttctacaa gagtgggaag tttgtgttca gttttaaggt     840
gggccagggt tacccgcatg atccccccaa ggtgaagtgt gagacaatgg tctatcaccc     900
caacattgac ctcgagggca acgtctgcct caacatcctc agagaggact ggaagccagt     960
ccttacgata aactccataa tttatggcct gcagtatctc ttcttggagc ccaaccccga    1020
ggacccactg aacaaggagg ccgcagaggt cctgcagaac aaccggcggc tgtttgagca    1080
gaacgtgcag cgctccatgc ggggtggcta catcggctcc acctactttg agcgctgcct    1140
gaaatagggt tggcgcatac ccaccccgc cacggccaca agccctggca tccctgcaa     1200 atatttattg ggggccatgg gtaggggttt gggggcggc cggtggggga atccctgcc     1260 ttggccttgc ctcccttcc tgccacgtgc cctagttat ttttttttt taacaccat     1320 gtgattaagg tcggcgctgc ctcccccgac ccactcagcg atgggaaatg aattggcttg    1380
tctagccccc ctgctgggtg cttgttcagc ccccactctg gctgtggag tgggtgggca    1440 acgggcctgg gtagctgggc ccaggcaacc caccccctcca cctctggagg tcccaccagg    1500
ctattaaagg ggaatgttac tgcaaaaaaa aaaaaaaaa                           1540

<210> SEQ ID NO 36
<211> LENGTH: 2568
<212> TYPE: DNA
<213> ORGANISM: Homo sapiens

<400> SEQUENCE: 36
cgcgcgcgca gtcgcgcgcg ggtcgtgccg taccaccgtc gcgggcaggc tcggccacga      60
gcgccagagc cccgcgcctc ccctcgcggc ctgtcccaag tccctgcccc gcaacagagc     120
gtcacttccg ccatccccgg cagcggttgg ggcggggcgc acggggagg gggccaggtc     180 ggagggaagc ccgcccgtgc ccgagcccgc gcccgagcag ggactacatt tcccgagggg    240
cctcggcggc ggctgcggcg acgggcgcgg caacgtcccc cggaagtgga gcccgggact    300
tccactcgtg cgtgaggcga gaggagccgg agacgagacc agaggccgaa ctcgggttct    360
gacaagatgg ccgggctgcc ccgcaggatc atcaaggaaa cccagcgttt gctggcagaa    420
ccagttcctg gcatcaaagc cgaaccagat gagagcaacg cccgttattt tcatgtggtc    480
attgctggcc tcaggattc cccctttgag ggagggactt taaacttga actattcctt    540 ccagaagaat acccaatggc agcccctaaa gtacgtttca tgaccaaaat ttatcatcct    600
aatgtagaca agttgggaag aatatgttta gatattttga agataagtg gtccccagca    660 ctgcagatcc gcacagttct gctatcgatc caggccttgt taagtgctcc caatccagat    720
gatccattag caaatgatgt agcggagcag tggaagacca cgaagccca agccatagaa    780 acagctagag catggactag gctatatgcc atgaataata tttaaattga tacgatcatc    840
aagtgtgcat cacttctcct gttctgccaa gacttcctcc tctttgtttg catttaatgg    900
acacagtctt agaaacatta cagaataaaa aagcccagac atcttcagtc ctttggtgat    960
taaatgcaca ttagcaaatc tatgtcttgt cctgattcac tgtcataaag catgagcaga   1020
ggctagaagt atcatctgga ttgttgtgaa acgtttaaaa gcagtggccc ctccctgctt    1080
ttattcattt cccccatcct ggtttaagta taaagcactg tgaatgaagg tagttgtcag    1140
```

```
gttagctgca ggggtgtggg tgttttatt ttatttatt ttatttatt tttgaggggg     1200
gaggtagttt aattttatgg gctccttttcc ccctttttttg gtgatctaat tgcattggtt     1260
aaaagcagct aaccaggtct ttagaatatg ctctagccaa gtctaacttt atttagacgc     1320
tgtagatgga caagcttgat tgttggaacc aaaatgggaa cattaaacaa acatcacagc     1380
cctcactaat aacattgctg tcaagtgtag attccccccct tcaaaaaaag cttgtgacca     1440
ttttgtatgg cttgtctgga aacttctgta aatcttatgt tttagtaaaa tatttttttgt     1500
tattctactt tgcctttgta cagtttattt tactgtgttt atttcattt cccaatttga       1560
caatcgtatt ttaaaattga aactgatgga acattctttc ttggtcttca ccatctgaca     1620
aattgaatgg caagaggtgg attttgccag tttcttttca ctgatgcaga tttgtgttaa     1680
gatagtactg aatggagtat ttataaactg gccctgagca tgcataaagc atcagtatct     1740
gaccttttt taaccttcta ggaatttgaa ataaatgtgt ttgtgttgtc tgattagatg      1800
atcattggtg tcttgccaca atgttaaaa attactgtac aggaaagtca cagcaaagat      1860
agcagttgtg actgacatgt aggactttca cagttgtgcc acattttgc ctaaaatttg      1920
ggttatgaca ttttcttgg ttcttatctg aaaatttcat ctgtaacctt tcatgtgtgt      1980
taagaaacac tgatctgatc atttgggatt tgctgaggca tttgtgagtc ttccttataa     2040
acctgatgag cagatctcaa ctatctagct tgtgtgtcat cagaaaggtt tatcccttg     2100
agagtatcaa gtcctcagtt aatgattctt gctttcatcc ctccagtatt tgctgtggga     2160
gctcgtttta ttcttaatt tggaattcag taattttct tctttattga cgaattcctc       2220
ccctcacaaa actgttcttt cccacctctc tccatatcta attcctgatt cttgttattt     2280
ttaagtcata aatgtagcca gtcataaata cataaatgtt aaccttcggg ttgcaacctt     2340
gtctcttgca gtttaaggta atggatattg tagcccatttt gaattttctt cactcttatt    2400
ctcgtaattc tggagttct tcagattgtg gtgtatttta ttgtgctcct atgtaagatg      2460
aagaattaac tattaaaatt acattttcaa catacaaaag cttttgatga ctggtaactg    2520
gtatccttcc aaataaatgc attgcttggt aaaaaaaaaa aaaaaaaa                  2568
```

<210> SEQ ID NO 37
<211> LENGTH: 5395
<212> TYPE: DNA
<213> ORGANISM: Homo sapiens

<400> SEQUENCE: 37

```
cgcctccccg cgcctcgttc gccgccgctg tcgccgccgc cgcccgagac tcgcgcagag       60
cagttatggc ggatcccgca gcccccacgc ccgcagctcc cgctccagcc caggccccgg      120
ctccagcccc ggaggcagtc ccggcccag ccgcagcccc cgtcccggcg ccggcgcccg       180
cctcggactc ggcctccggg ccgtcctcgg actccggccc agaagccggc tcgcagcgcc      240
tgctgttttc tcacgacctg gtgtcgggcc gttaccgtgg ctccgtgcac ttcgggctgg      300
tgcgcctcat ccacggcgag gactcggact cggaggcga ggaggagggc cgcgggagct       360
cggggtgctc cgaggccggg ggcgcgggcc acgaggaggg ccgggccagc cccctgcgcc      420
gcggctacgt gcgcgtccag tggtacccgg agggcgtcaa gcagcatgtg aaggagacca      480
agctgaaact agaggaccgt tctgtggtgc cccgagatgt ggtccggcac atgcgatcca     540
ccgacagtca gtgtggcacg gtgatcgacg tcaacatcga ctgtgccgtc aagctcatcg     600
gcaccaactg catcatctat cccgtcaaca gcaaggacct gcagcacatc tggcccttca    660
tgtatgggga ctacattgcc tatgactgct ggctggggaa ggtctacgac ttgaagaacc    720
```

```
agatcatcct gaagctatcc aacggcgcca ggtgctccat gaacacgaaa gatggcgcca      780
agctctacga cgtctgcccg cacgtcagcg actcgggtct cttcttcgat gattcctatg      840
gcttctaccc aggccaggtg ctcattggcc ctgccaagat cttctccagc gtccagtggc      900
tgtcaggtgt caagcccgtg ctcagcacca agagcaagtt ccgagtggtg gtggaagagg      960
tgcaggttgt agagttgaaa gttacatgga ttaccaagag tttctgtcca gggggcacgg     1020
acagcgtcag ccccccaccc tctgtcatca cccaggaaaa cctaggcagg gtgaagcgtc     1080
tcggatgctt tgaccatgct cagcggcagc ttggggagcg ctgtctgtat gtcttcccag     1140
ccaaggtaga gccagccaag attgcctggg aatgtccaga aaaaaactgc gcccagggga     1200
agggctctat ggccaagaag gtgaagcgcc tgttgaagaa gcaggttgtg cggatcatgt     1260
catgctcccc agacacccag tgttcccggg accattccat ggaagaccca gacaagaagg     1320
gggaatccaa aaccaagagc gaagcggagt ctgccagccc tgaggagacg cccgatggct     1380
ctgccagtcc agtggagatg caggacgagg gtgcagagga gccccacgag gcaggagagc     1440
agctgccccc attcctgcta aaagaaggca gagatgacag gctgcactcg gcagagcagg     1500
acgcagatga tgaggctgct gatgacacgg acgacaccag ttcggtgacc tcctctgcca     1560
gctccaccac ttcctcccag agcggcagcg gcacgagtcg caaaaagagc atcccctttgt     1620 ccatcaagaa cttaaagcgc aaacacaaga ggaagaagaa taaatcact cgagacttca      1680 agccagggga cagggtggca gtggaggtgg tgaccacgat gacctcagcc gacgtgatgt     1740
ggcaggatgg ctccgtggaa tgcaacatcc gctccaacga cctcttccct gtgcaccacc     1800
tggacaacaa cgagttctgc cctggagact tcgtggtaga taagcgagtc cagagctgtc     1860
cagaccctgc tgtctacggt gtggtacagt ctggggacca catcggccgt acctgcatgg     1920
tgaagtggtt caagctgagg ccgagtgggg acgacgtgga gctgattgga gaagaggaag     1980
atgtgagtgt ttacgacatt gctgaccacc ctgactttag gttccgtaca actgacatcg     2040
tcatccgcat cggcaatact gaggatgggg ctcctcacaa ggaggatgag ccatcggtgg     2100
gccaggtggc ccgtgtggac gtcagcagca aggtggaggt ggtgtgggct gacaactcaa     2160
agaccatcat cctgccccag cacttgtaca acatagagtc tgagattgag gagtcagact     2220
acgattcggt agaaggcagc accagcgggg catcctcgga tgaatgggaa gatgatagtg     2280
acagctggga cacggacaat gggctggtgg aggacgagca ccccaagata gaggagcccc     2340
ccatcccacc cctggagcag ccggtggccc ctgaggacaa gggagtggtg atcagtgaag     2400
aggcagccac agctgccgtc caggggggctg tggccatggc tgcccccatg gccgggctga     2460
tggagaaggc tggcaaggac gggccaccca agagcttccg ggagttgaaa gaggccatca     2520
agatcctgga gagcctcaag aacatgactg tggagcagct gctgacgggc tcgcccacct     2580
ctccgactgt ggagcctgag aagccaactc gggagaagaa gtttctggat gacatcaaga     2640
agctacagga aaacctcaag aagaccctgg acaatgtggc cattgtagag gaggagaaga     2700
tggaagcagt gcccgacgta gagcgcaagg aggacaagcc cgaggggcag tcacctgtga     2760
aggctgagtg gccccagcgaa accccggtgc tgtgccagca gtgtggcggc aagcctggcg     2820
tcaccttcac cagcgccaag ggcgaggtct tctccgtact ggagtttgca ccctcaaatc     2880 attctttttaa gaaaattgag ttccagcctc cagaagccaa gaagttcttc agcacagtgc     2940
ggaaggagat ggcgctgctg gctacctcac tgcctgaggg catcatggtc aagactttg      3000 aagatagaat ggacctcttc tcagctctca tcaagggccc cactcgaacc ccctacgagg     3060
```

```
atggcctcta cttgtttgac atccagctcc ccaacatcta cccagccgtg cccccccact     3120
tctgctacct ctcccaatgc agtggccgcc tgaaccccaa cctgtatgac aatgggaagg     3180
tgtgtgtcag cctcctgggc acctggattg gaaaggggac agagaggtgg acaagcaagt     3240
ccagccttct ccaggtgctc atctccatcc aaggtctgat cctggtaaat gaaccatact     3300
acaacgaagc cggcttcgac agtgaccgag gcctgcagga aggctatgaa acagtcgct     3360
gttacaatga gatggcgctg atccgcgtgg tgcagtccat gacccagctg gtgcggcggc     3420
cccccgaggt ctttgagcag gagatcaggc aacactttag cactggtggc tggcggctgg     3480
tgaaccgtat cgagtcctgg ctggaaaccc atgccctgct ggagaaggcc caggcactgc     3540
ccaacggggt gcccaaggcc agcagctcgc cagagccccc agctgtagcc gagctgtcag     3600
actccggcca acaagaacct gaggatggag ggccagcccc aggagaggcc tcccagggct     3660
cagactcaga gggcggtgcc cagggcctgg cctcagctag cagggaccac acagaccaga     3720
cttcggagac cgcaccagac gcatcggtgc cacccagtgt gaaaccaaag aagcggagaa     3780
agagctaccg gagcttctta cctgagaaga gtggctaccc tgacatcggc ttcccctct     3840
tcccactttc caagggtttc atcaagagca tccggggtgt cctgacgcag ttccgggctg     3900
ccctgctaga ggcaggcatg ccggagtgca cagaggacaa gtagctgcca ggcacagagg     3960
aaagagcatc accgtgggag aggccagccg ccgcctgctc actcccccc ggaatcaccc     4020
ctcttcccat gcccctctgt ccccactgca aacccactgc cctcttctcc caaggtgag     4080
tttgatgctg aagtgcaaga agtgtgttga gatgctgccg tttctatttt gaagcgagct     4140
ttcaacaggc gggtccctg tggcaaagaa atcggaacc ctgttgccga ttttccattt     4200
gtcacccag cagaatgtcc ggcacttgct cccttgctgc cccttctcag gtcagaggcg     4260
ggtgttccag ggcctgccgc ggggctctct gggccggttc cctgcagacc cgcaggagag     4320
cacatgtgcc ttgcatgaag tgtgggttgc gccaacaatt cccctggtcc ctttcaacct     4380
gtttagttca actcaagcct ccctgtgtcc cagaccctcc tgctgccacc accacccagg     4440
tcctccctag tcctccagcg tcaacactat cccttgggag ttgtagctgc tgtcactgac     4500
tcccggctat acatggcctg tcgaccacgt tatagccctc aggcctgttg aacttgctct     4560
ctaagagagg ttgggaccag gctaggttcc gggtgacgcc caggagaggt ggtggccttc     4620
acacatgcac atggagttga ggaccaggga gctgcaggga aagcaacagc tataggtgcc     4680
ttgctcttct gtcggaggct gctggggca agagcagctg cacaaggcca gggcaagtgc     4740
tagggcccct cccccatcac atggtcacac tgggacaggc gtgcagctca ctgaactcca     4800
agcgagccag ccctctcttg gactagaagg cctactgtca gcccttcgct tacaaactgc     4860
aggctcaatc cgaaggggac ggccggcggg ggctctccta gtgccagag acaggcccag     4920
aggtttacaa gttttctaag cttttgataa tgtgaagctc caggccgaga ggatgctgtt     4980
gagcacattg cagctatgta attttggtg tatgtatgta atatttaagg ttggaaaaaa     5040
aactcaaaag caaagatatt aactcttatt agaaaaaaag acaaaaaaaa agccaaagca     5100
tgatgcgtct tgtcagcctt aagtgggctc cacacctgtg ctgtgctgtg accgccagc     5160
cagcagagct gcgggaggat ggagccggac cacacaccgt ggcatttgga accgagtcgg     5220
tatcttgttt gagaaacacc cggagtgact ggtgggctg tgcttcccag tgcattgtac     5280
atgtggagat gtgaatgcct actgcttacg atatctgtat aaagtgctgt gtgattaaac     5340
tttttttac ttgcaaaaaa aaaaaaaaaa aaaaaaaaaa aaaaaaaaaa aaaaa         5395
```

```
<210> SEQ ID NO 38
<211> LENGTH: 1207
<212> TYPE: DNA
<213> ORGANISM: Homo sapiens

<400> SEQUENCE: 38
cctctccgcc acttccctcg cttctgacca tagtttgcgg ggaagggagc gagcgcgtcg      60
aaaaccaagg aacgtgcgcg ctgacgtcac ggttgaggct cggagctgag gggccgcgga     120
gggcgtggcc tgcgggcggt tataaagagg cagtggtgcg cgcgcggccg gctcagtgct     180
gccgggcacc ggggcggcgg gttggtctac gctgtgcgcg gcggacgtcg gaggcagcgg     240
ggagcggagc ggggccgccg gggcctctcc agggccgcag cggcagcagt tgggcccccc     300
gccccggccg gcggaccgaa gaacgcagga aggggccgg ggggacccgc ccccggccgg      360
ccgcagccat gaactccaac gtggagaacc tacccccgca catcatccgc ctggtgtaca     420
aggaggtgac gacactgacc gcagacccac ccgatggcat caaggtcttt cccaacgagg     480
aggacctcac cgacctccag gtcaccatcg agggccctga ggggacccca tatgctggag     540
gtctgttccg catgaaactc ctgctgggga aggacttccc tgcctcccca cccaagggct     600
acttcctgac caagatcttc caccogaacg tgggcgccaa tggcgagatc tgcgtcaacg     660
tgctcaagag ggactggacg gctgagctgg gcatccgaca cgtactgctg accatcaagt     720
gcctgctgat ccaccctaac cccgagtctg cactcaacga ggaggcgggc cgcctgctct     780
tggagaacta cgaggagtat gcggctcggg cccgtctgct cacagagatc cacggggcg      840 ccggcgggcc cagcggcagg gccgaagccg gtcgggccct ggccagtggc actgaagctt     900
cctccaccga ccctggggcc ccaggggcc cgggaggggc tgagggtccc atggccaaga     960
agcatgctgg cgagcgcgat aagaagctgg cggccaagaa aaagacggac aagaagcggg    1020
cgctgcggcg gctgtagtgg gctctcttcc tccttccacc gtgacccaa cctctcctgt     1080 cccctccctc caactctgtc tctaagttat ttaaattatg gctggggtcg gggagggtac    1140 aggggggcact gggacctgga tttgttttc taaataaagt tggaaaagca gaaaaaaaaa    1200
aaaaaaa                                                                    1207
```